(12) United States Patent
Chen et al.

(10) Patent No.: US 8,744,571 B2
(45) Date of Patent: Jun. 3, 2014

(54) METHOD AND SYSTEM FOR THE PREDICTION OF CARDIAC ARRHYTHMIAS, MYOCARDIAL ISCHEMIA, AND OTHER DISEASED CONDITION OF THE HEART ASSOCIATED WITH ELEVATED SYMPATHETIC NEURAL DISCHARGES

(75) Inventors: Peng-Sheng Chen, Indianapolis, IN (US); Shengmei Zhou, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 1062 days.

(21) Appl. No.: 12/755,139

(22) Filed: Apr. 6, 2010

(65) Prior Publication Data

US 2010/0268289 A1    Oct. 21, 2010

Related U.S. Application Data

(63) Continuation of application No. 11/205,923, filed on Aug. 16, 2005, now Pat. No. 7,725,178, which is a continuation-in-part of application No. 11/069,753, filed on Feb. 28, 2005, now Pat. No. 7,266,410, which is a continuation-in-part of application No. 10/882,645, filed on Jun. 30, 2004, now abandoned.

(51) Int. Cl.
*A61N 1/00* (2006.01)
*A61B 5/04* (2006.01)

(52) U.S. Cl.
USPC .................. 607/3; 600/509; 600/515; 607/11

(58) Field of Classification Search
USPC .................................. 600/509, 515; 607/3, 11
See application file for complete search history.

(56) References Cited

U.S. PATENT DOCUMENTS 4,026,300 A    5/1977    DeLuca et al.
(Continued)

FOREIGN PATENT DOCUMENTS

EP    0882452    12/1998
(Continued)

OTHER PUBLICATIONS

Adrian, et al.: Discharges in mammalian sympathetic nerves, J Physiol 1932;74:115-133.
(Continued)

*Primary Examiner* — Nicole F Lavert
(74) *Attorney, Agent, or Firm* — Linda B. Huber; Nixon Peabody LLP

(57) ABSTRACT

Methods and systems are provided for determining an increased likelihood of the occurrence of a cardiac arrhythmia, myocardial ischemia, congestive heart failure and other diseased conditions of the heart associated with elevated sympathetic neural discharges in a patient. The methods and systems comprise monitoring the sympathetic neural discharges of a patient from the stellate ganglia, the thoracic ganglia, or both, and detecting increases in the sympathetic neural discharges. The methods and systems may further comprise delivering therapy to the patient in response to a detected increase in the sympathetic neural discharge, such as delivering one or more pharmacological agents; stimulating myocardial hyperinnervation in the sinus node and right ventricle of the heart of the patient; and applying cardiac pacing, cardioversion or defibrillation shocks. Pharmacologic agents which may be used in connection with the delivery of include those which are known to exert anti-arrhythmic effect and anti-convulsant agents, such as phenytoin, carbamazepine, valproate, and phenobarbitone. Other pharmacologic agents may be used to treat impending myocardial ischemia and other diseased conditions of the heart associated with elevated sympathetic neural discharges.

30 Claims, 27 Drawing Sheets

(56) References Cited

U.S. PATENT DOCUMENTS

| | | | |
|---|---|---|---|
| 4,573,481 A | 3/1986 | Bullara | |
| 4,774,967 A | 10/1988 | Zanakis et al. | |
| 4,919,140 A | 4/1990 | Borgens et al. | |
| 5,147,294 A | 9/1992 | Smith et al. | |
| 5,199,428 A | 4/1993 | Obel et al. | 607/44 |
| 5,203,326 A | 4/1993 | Collins | 607/4 |
| 5,224,477 A | 7/1993 | Itoh | |
| 5,251,621 A | 10/1993 | Collins | 607/4 |
| 5,578,061 A | 11/1996 | Stroetmann et al. | 607/4 |
| 5,658,318 A | 8/1997 | Stroetmann et al. | 607/6 |
| 5,700,282 A | 12/1997 | Zabara | 607/9 |
| 5,921,940 A | 7/1999 | Verrier et al. | |
| 6,272,377 B1 | 8/2001 | Sweeney et al. | 600/515 |
| 6,351,668 B1 | 2/2002 | Chen | |
| 6,353,757 B2 | 3/2002 | Chen | |
| 6,398,800 B2 | 6/2002 | Chen | |
| 6,487,450 B1 | 11/2002 | Chen | |
| 6,521,462 B1 | 2/2003 | Tanouye et al. | 436/149 |
| 6,824,538 B2 | 11/2004 | Chen | |
| 6,885,888 B2 | 4/2005 | Rezai | 607/9 |
| 6,950,752 B1 | 9/2005 | Friend et al. | 702/19 |
| 7,142,911 B2 | 11/2006 | Boileau et al. | 607/3 |
| 7,257,439 B2 | 8/2007 | Llinas | 600/544 |
| 7,266,410 B2 | 9/2007 | Chen | 607/3 |
| 7,725,178 B2 | 5/2010 | Chen et al. | |
| 2004/0006264 A1 | 1/2004 | Mojarradi et al. | 600/378 |
| 2005/0074821 A1 | 4/2005 | Wild, Jr. et al. | |
| 2006/0004413 A1 | 1/2006 | Chen | |
| 2006/0004414 A1 | 1/2006 | Chen | |
| 2006/0074451 A1 | 4/2006 | Chen et al. | |

FOREIGN PATENT DOCUMENTS

| | | |
|---|---|---|
| WO | WO 99/39624 | 8/1999 |
| WO | WO 01/62334 | 8/2001 |
| WO | 2006004850 A2 | 1/2006 |
| WO | 2006094022 A2 | 9/2006 |

OTHER PUBLICATIONS

Akingba, et al.: Application of nanoelectrodes in recording biopotentials. Nanotoechnology, 2003, IEEE-NANO 2003;2:870-874.

Akira, et al: Induction of artrial fibrillation and nerve sprouting by prolonged left artrial pacing in dogs, PACE 2003;26:2247-2252.

Anthonio et al., "β-Andrenoceptor density in chronic infarcted myocardium: a subtype specific decrease of $β_1$-adrenoceptor density," International Journal of Cardiology, 2000, pp. 137-141, vol. 72, Elsevier Science Ireland Ltd., Ireland.

Antzelevitch, "Tpeak-Tend interval as an index of transmural dispersion of repolarization," European Journal of Clinical Investigation, 2001, pp. 555-557, vol. 31, Blackwell Science Ltd.

Armour JA: Activity of in situ middle cervical ganglion neurons in dogs, using extracellular recording techniques. Can J Physiol Pharmacol. 1985;63:704-716.

Armour, et al.: Activity of canine in situ left atrial ganglion neurons. Am.J Physiol 1990:259:H1207-H1215.

Armour, et al.: Activity of in vivo canine ventricular neurons. Am.J Physiol 1990:258:H326-H336.

Arntz, et al.: Circadian variation of sudden cardiac death reflects age-related variability in ventricular fibrillation. Circulation 1993;88:2284-89.

Aronow, et al.: Circadian variation of primary cardiac arrest or sudden cardiac death in patient aged 62 to 100 years (mean 82). Am J Cardiol 1993;71:1455-1456.

Aronow, et al.: Circadian variation of sudden cardiac death or fatal myocardial infarction is abolished by propranolol in patients with heart disease and complex ventricular arrhythmias. Am J Cardiol 1994;74:819-821.

Athill, et al.: Influence of wavefront dynamics on transmembrane potential characteristics during atrial fibrillation, J Casrdiovasc Electrophysiol 2000; 11:913-921.

Barbacid M: Nerve growth factor: a tale of two receptors. Oncogene 1993:8:2033-2042.

Barber, et al.: Interruption of sympathetic and vagal-mediated afferent responses by transmural myocardial infarction. Ciculation 1985;72:623-631.

Barhanin, et al: K(V)LQTI and IsK (minK) proteins associate to form the 1(Ks) cardiac potassium current. Nature 1996;384:78-80.

Barrett, et al.: What sets the long-term level of renal sympathetic nerve activity: a role for angiotensin II and baroreflexes? Circ.Res. 2003;92:1330-1336.

Bartels et al., "Influence of Myocardial Ischemia and Reperfusion on β-Adrenoceptor Subtype Expression," Journal of Cardiovascular Pharmacology, 1998, pp. 484-487, vol. 31, Lippincott-Raven Publishers, Philadelphia, PA, USA.

Bengel, et al.: Myocardial efficiency and sympathetic reinnervation after orthotopic heart transplantation: a noninvasive study with positron emission tomography. Circulation 2001;103:1881-1886.

Benjamin, et al.: Impact of atrial fibrillation on the risk of death: the Framingham Heart Study [see comments]. Circulation 1998;98:946-952.

Bers, "Calcium and Cardiac Rhythms: Physiological and Pathophysiological," Circulation Research, 2002, pp. 14-17, vol. 90, American Heart Association, USA.

Blakey, et al.: Sudden, unexpected death in cardiac transpant recipients: an autopsy study. J Heart Lung Transplant. 2001;20:229 (abstract).

Boczek-Funcke, et al.: Classification of preganglionic neurones projecting into the cat cervical sympathetic trunk. J Physiol 1992;453:319-339.

Bonnemeier, et al.: Course and prognostic implications of QT interval and QT interval variability after primary coronary angioplasty in acuate myocardial infarction. J Am Coll Cardiol 2001;37:44-50.

Bosch et al., "$β_3$-Adrenergic regulation of an ion channel in the heart-inhibition of the slow delayed rectifier potassium current $1_{ks}$ in guinea pig ventricular myocytes," Cardiovascular Research, 2002, pp. 393-403, vol. 56, Elsevier science B.V.

Bristow et al., "Decreased Catecholamine Sensitivity and β-Adrenergic-Receptor Density in Failing Human Hearts," The New England Journal of Medicine, Jul. 22, 1982, pp. 205-211, vol. 307, No. 4, Massachusetts Medical Society, Boston, MA, USA.

Bristow et al., "Reduced $β_1$ Receptor Messenger RNA Abundance in the Failing Human Heart," The Journal of Clinical Investigation, Dec. 1993, pp. 2737-2745, vol. 92, The American Society for Clinical Investigation, Inc., USA.

Bristow et al., "$β_1$—and $β_2$-Adrenergic-Receptor Subpopulations in Nonfailing and Failing Human Ventricular Myocardium: Coupling of Both Receptor Subtypes to Muscle Contraction and Selective $β_1$-Receptor Down-Regulation in Heart Failure," Circulation Research, Sep. 1986, pp. 297-309, vol. 59, No. 3, American Heart Association, USA.

Bristow et al., "$β_1$-and $β_2$-Adrenergic-Receptor-Mediated Adenylate Cyclase Stimulation in Nonfailing and Failing Human Ventricular Myocardium," Molecular Pharmacology, Mar. 1989, pp. 295-303, vol. 35, No. 3, American Society for Pharmacology and Experimental Therapeutics, William & Wilkins, USA.

Brodde et al., "Adrenergic and Muscarinic Receptors in the Human Heart," Pharmacological Review, 1999, pp. 651-689, 0031-6997/99/5104-0651, The American Society for Pharmacology and Experimental Therapeutics, USA.

Brodde et al., "β-Adrenoceptors in the transplanted human heart: unaltered β-adrenoceptor density, but increased proporation $β_2$-adrenoceptor with increasing posttransplant time," Naunyn-Schmiedeberg's Arch. Pharmacol., 1991, pp. 430-436, vol. 344, Springer-Verlag.

Burke, et al.: Evidence for functional sympathetic reinnervation of left ventricle and coronary arteries after orthotopic cardiac transplantation in humans, Circulation 1995;91:72-78.

Cao JM, et al.: Nerve Sprouting and sudden cardiac death. Circ Res 2000 86: 816-821.

Cao JM, et al: Relationship between regional cardiac hyperinnervation and ventricular arrhythmia, Circulation 2000;101:1960-1969.

(56) References Cited

OTHER PUBLICATIONS

Centers for Disease Control and Prevention: State-specific mortality from sudden cardiac death—United States, 1999, MMWR Morb. Mortal.Wkly.Rep, 2002;51:123-126.

Cesario, eet al.: Electrophysioloogical characterization of cardiac veins in humans. J Interventional Cardiac Electrophysiol 2004; 10:241-7.

Chang, et al.: Nerve sprouting and sympathetic hyperinnervation in a canine model of atrial fibrillation produced by prolonged right atrial pacing. Circulation 2001;103:22-25.

Chaudhry et al., "Differential Interaction of $\beta_1$- and $\beta_3$—Adrenergic Receptors with $G_1$ in Rat Adipocytes," Cellular Signalling, 1994, pp. 457-465, vol. 6, No. 4, Elsevier Science Ltd., Great Britain.

Chen, et al.: Sympathetic nerve sprouting, electrical remodeling and the mechanisms of sudden cardiac death, Cardiovasc Res 2001;50:409-416.

Cheng, et al.: Upregulation of functional beta(3)—adrenergic receptor in the failing canine myocardium. Circ Res 2001;89:599-606.

Chou, et al.: Effects of procainamide on electrical activity to the thoracic veins and the atria in canine model of sustained atrial fibrillation. Am J Physiol 2004;286:H1936-H1945.

Chou, et al.: Marshall bundle and the valve of Vieussens, J Cardiovasc Electrophysiol 2003;14:1254.

Chudin et al., "Intracellular $Ca^{2+}$ Dynamics and the Stability of Ventricular Tachycardia," Biophysical Journal, Dec. 1999, pp. 2930-2941, vol. 77, Biophysical Society.

Creamer et al., "Acute and Chronic Effects of Sotalol and Propranolol on Ventricular Repolarization Using Constant-Rate Pacing," Am. J. Cardiol., May 1, 1986, pp. 1092-1096, vol. 57.

Dae et al., "Heterogeneous Sympathetic Innervation in German Shepherd Dogs With Inherited Ventricular Arrhythmia and Sudden Cardiac Death", Circulation, Aug. 19, 1997, pp. 1337-1342, vol. 96, No. 4, American Heart Association, USA.

Dae, et al.: Scintigraphic assessment of MIBG uptake in globally denervated human and canine hearts—implications for clinical studies. J Nucl Med 1992;33:1444-1450.

Davey P: QT interval and mortality from coronary artery disease. Prog Cardiovasc Dis 2000;42:359-384.

Dinçer et al., "The Effect of Diabetes on Expression of $\beta_1$-, $\beta_2$-, and $\beta_3$-Adrenoreceptors in Rat Hearts," Diabetes, Feb. 2001, pp. 455-461, vol. 50.

Donckier et al., "Cardiovascular effects of beta 3-adrenoceptor stimulation in perinephritic hypertension," European Journal of Clinical Investigation, 2001, pp. 681-689, vol. 31, Blackwell Science Ltd.

Doshi, et al.: Initial experience with an active-fixation defibrillation electrode and the presence of nonphysiologicai sensing. PACE 2001;24:1713-16.

Duff et al., "Electrophysiologic Actions of High Plasma Concentrations of Propranolol in Human Subjects,"Journal of the American College of Cardiology, Dec. 1983, pp. 1134-1140, vol. 2, No. 6, American College of Cardiology, Elsevier Biomedical, USA.

Eckardt et al., "Arrhythmias in Heart Failure: Current Concepts of Mechanisms and Therapy," Journal of Cardiovascular Electrophysiology, Jan. 2000, pp. 106-117, vol. 11, No. 1, Futura Publishing Company Inc., Armonk, NY, USA.

Edvardsson et al., "Effects of acute and chronic beta-receptor blockade on ventricular repolarisation in man," British Heart Journal, Jun. 1981, pp. 628-636, vol. 45, No. 6, British Medical Association, UK.

Eldar, et al.: Significance of paroxysmal atrial fibrillation complicating acute myocardial infarction in the thrombolytic era. SPRINT and Thrombolytic Survey Groups, Circulation 1998;97:965-970.

Farrukh et al., "Up-Regulation of Beta$_2$-Adrenergic Receptors in Previously Transplanted, Denervated Nonfailing Human Hearts," Journal of the American College of Cardiology, Dec. 1993, pp. 1902-1908, vol, 22, No. 7, Elsevier, USA.

Fozzard, "Afterdepolarizations and triggered activity," Supplement to Basic Research in Cardiology, 1992, pp. 105-113, vol, 87, Suppl. 2, Steinkopff Verlag Darmstadt Springer-Verlag, New York, NY, USA.

Franklin et al., "Control of Neuronal Size Homeostasis by Trophic Factor-mediated Coupling of Protein Degradation to Protein Synthesis," The Journal of Cell Biology, Sep. 7, 1998, pp. 1313-1324, vol. 142, No. 5, The Rockefeller University Press, USA.

Freemantle et al., "β Blockade after mycardial infarction: systemtic review and meta regression analysis," BMJ, Jun. 26, 1999, pp. 1730-1737, vol. 318, UK.

Fu Sy, Gordon T: The cellular and molecular basis of peripheral nerve regeneration. Mol.Neurobiol. 1997;14:67-116.

Gang, et al.: Short coupled premature ventricular contraction initiating ventricular fibrillation in a patient with Brugada syndrome. J Cardiovasc Electrophysiol 2004;15:837.

Garfinkel, et al.: Preventing ventricular fibrillation by flattening cardiac restitution. Proc Natl Acad Sci U S A 2000;97-6061-66.

Gauthier et al., "Interspecies Differences in the Cardiac Negative Inotropic Effects of $\beta_3$-Adrenoceptor Agonists," The Journal of Pharmacology and Experimental Therapeutics, 1999, pp. 687-693, vol. 290, The American Society for Pharmacology and Experimental Therapeutics, USA.

Gauthier, et al.: Functional beta3-adrenoceptor in the human heart. J Clin Invest 1996;98:556-562.

Ginty DD, Segal RA: Retrograde neurotrophin signaling: Trk-ing along the axon, Curr.Opin.Neurobiol. 2002;12:268-274.

Goldberg, et al.: Impact of atrial fibrillation on the in-hospital and long term survival of patients with acute myocardial infarction: A community-wide perspective. Am Heart J 1990;119:996-1001.

Gottlieb et al., "Effect of Beta-Blockade on Mortality Among High-Risk and Low-Risk Patients After Mycocardial Infarction," The New England Journal of Medicine, Aug. 20, 1998, pp. 489-497, vol. 339, No. 8, Massachusetts Medical Society, Boston, MA, USA.

Guth L.: Regeneration in the mammalian peripheral nervous system, Physiol Rev 1956;36:441-478.

Hamabe, et al.: Correlation between anatomy and electrical activation in canine pulmonary veins. Circulation 2003;107:1550-1555.

Hamzel, et al.: The role of approximate entropy in predicting ventricular defibrillation threshold. J Cardiovasc Pharmacol Ther 2002;7:45-52.

Harding et al., "Lack of evidence for β3-adrenoceptor modulation of contractile function in human ventricular myocytes," Supplement to Circulation, Abstracts from the 70th Scientific Sesssions, Nov. 9-12, 1997, p. 284, vol. 96, No. 8, American Heart Association USA.

Hartikainen, et al.: Sympathetic reinnervation after acute myocardial infarction. Am J Cardiol 1996;77:5-9.

Hassankhani, et al: Overexpression of NGF within the heart of transgenic mice causes hyperinnervation, cardiac enlargement, and hyperplasia of ectopic cells. Dev Biol 1995:169:309-321.

Hayashi H, et al.: Effects of cytochalasin D on electrical restitution and the dynamics of ventricular fibrillation in isolated rabbit heart. J Cardiovasc Electrophysiol 2003;14:1077-1084.

Hayashi, et al.: Aging-related increase to inducible atrial fibrillation in the Rat Model. J Cardiovasc Electrophysiol 2002;13:801-808.

Heath et al., "Overexpression of nerve growth factor in the heart alters ion channel activity and β-adrenergic signalling in an adult transgenic mouse," Journal of Physiology, 1998, pp. 779-791, vol. 512.3.

Heid et al., "Genome Methods: Real Time Quantitative PCR," Genome Research, 1996, pp. 986-994, vol. 6, Cold Spring Harbor Laboratory Press.

Hjalmarson, "Effects of Beta Blockade on sudden Cardiac Death During Acute Myocardial Infarction and the Postinfarction Period," The American Journal of Cardiology, Nov. 13, 1997, pp. 35J-39J, vol. 80(9B), Excerpta Medica, Inc., USA.

Hom et al., "$\beta_3$-Adrenoceptor Agonist-Induced Increases in Lipolysis, Metabolic Rate, Facial Flushing, and Reflex Tachycardia in Anesthetized Resus Monkeys," The Journal of Pharmacology and Experimental Therapeutics, 2001, pp. 299-307, vol. 297, American Society for Pharmacology and Experimental Therapeutics.

Hume, et al.: Chloride conductance pathways in heart. Am J Physiol 1991;261:C399-C412.

Hwang, et al.: Radiofrequency ablation of accessory pathways guided by the location of the ligament of Marshall. J Cardiovasc Electrophysiol 2003;14:616-620.

(56) References Cited

OTHER PUBLICATIONS

Hwang, et al.: Vein of Marshall cannulation for the analysis of electrical activity in patients with focal atrial fibrillation. Circulation 2000;101:1503-1505.

Ieda, et al.: Endothelin-1 regulates cardiac sympathetic innervation in the rodent heart by controlling nerve growth factor expression. J.Clin. Invest 2004; 113:876-884.

Ihl-Vahl et al., "Differential Regulation of mRNA Specific for $\beta_1$- and $\beta_2$-adrenergic Receptor in Human Failing Hearts. Evaluation of the Absolute Cardiac mRNA Levels by Two Independent Methods,"J. Mol. Cell. Cardiol., 1966, pp. 1-10, vol. 28, Academic Press Limited.

Ihl-Vahl, et al., "Regulation of $\beta$-Adrenergic Receptors in Acute Myocardial Ischemia: Subtype-selective increase of mRNA Specific for $\beta_1$-Adrenergic Receptors," J. Mol. Cell. Cardiol., 1995, pp. 437-452, vol. 27, Academic Press Limited.

Janse, et al: Effects of unilateral stellate ganglion stimulation and ablation on electrophysiologic changes induced by acute myocardial ischemia in dogs. Circulation 1985;72:585-595.

Jardine, et al.: A neural mechanism for sudden death after myocardial infarction. Clin.Auton.Res. 2003;13:339-341.

Josephson, et al.: The beta subunit increases Ca2+ currents and gating charge movement of human cardiac L-type Ca2+ channels. Biophys J 1996;70:1285-1293

Kadish, et al.: Paradoxical effects of exercise on the QT interval in patients with polymorphic ventricular tachycardia receiving type la antiarrhythmic agents. Circulation 1990;81:14-19.

Kaplan DR,: Neurotrophin signal transduction in the nervous system. Curr Opin Neurobiol 2000;10:381-391.

Kathofer, et al.: Functional coupling of human beta 3-adrenoreceptors to the KvLQT1/MinK potassium channel, J Biol Chem 2000;275:26743-26747.

Kaumann et al., "Modulation of human cardiac function through 4 $\beta$-adrenoceptor populations," Naunyn-Schmiedeberg's Arch Pharmacol., Jan. 22, 1997, pp. 667-681, 355, Springer-Verlag.

Kawashima et al., "Contrasting Effects of Dopamine and Dobutamine on Myocardial Release of Norepinephrine during Acute Myocardial Infarction," Japanese Heart Journal, Nov. 1985, pp. 975-984, vol. 26, No. 6, Japanese Heart Journal Association, Tokyo, Japan.

Kaye, et al.: Reduced myocardial nerve growth factor expression in human and experimental heart failure. Circ Res 2000;86-E80-E84.

Kihara et al., "Intracellular Calcium and Ventricular Fibrillation," Circulation Research, May 1991, pp. 1378-1389, vol. 68, No. 5, American Heart Association, USA.

Kim, et al.: Sympathetic nerve sprouting after orthotopic heart transplantation. J Heart Lung Transplantation 2004;23:1349-1358.

Kim, et al.: The Ligament of Marshall: A structural analysis in human hearts with implications for trial arrhythmias. J Am Coil Cardiol. 2000;36:1324-7.

Kirkness et al., "The Dog Genome: Survey Sequencing and Comparative Analysis," Science, Sep. 26, 2003, pp. 1898-1903, vol. 301.

Kitamura et al., "The Negative Inotropic Effect of $\beta_3$-Adrenoceptor Stimulation in the Beating Guinea Pig Heart," Journal of Cardiovascular Pharmacology, May 2000, pp. 786-790, vol. 35, Lippincott Williams & Wilkins, Inc., Philadelphia, PA, USA.

Kleiger et al.: Decreased heart rate variability and its association with increased mortality after acute myocardial infarction. Am J Cardiol 1987;59:256-262.

Kohout et al., "Augmentation of Cardiac Contractility Mediated by the Human $\beta_3$-Adrenergic Receptor Overexpressed in the Hearts of Transgenic Mice," Circulation, Nov. 13, 2001, pp. 2485-2491, vol. 104, The American Heart Association, USA.

Kong Jr, et al.: Circadian variation in human ventricular refractoriness. Circulation 1995;92:1507-1516.

Korsching S: The neurotrophic factor concept: a reexamination, J.Neurosci. 1993;13:2739-2748.

Korsching, et al.: Nerve growth factor in sympathetic ganglia and corresponding target organs of the rat: correlation with density of sympathetic innervation. Proc Natl Acad Sci 1983;80:3513-3516.

Korsching, et al: Developmental changes of nerve growth factor levels in sympathetic ganglia and their target organs. Dev Biol 1988;126:40-46.

Kotzbauer, et al.: Postnatal development of survival responsiveness in rat sympathetic neurons to leukemia inhibitory factor and ciliary neurotrophic factor. Neuron 1994; 12:763-773.

La Rovere, et al.: Baroreflex sensitivity and heart rate varibility in the indentification of patients at risk for life-threatening arrhythmias: implications for clinical trials. Circulation 2001;103-2072-2077.

Lai, et al.: Co-localization of tenascin and sympathetic nerves in a canine model of nerve sprouting and sudden cardiac death. J Cardiovasc Electrophysiol 2000;11:1345-51.

Lampert, et al.; Circadian variation of sustained ventricular tachycardia in patients with coronary artery disease and implantable cardioverter-defibrillators, Circulation 1994;90:241-247.

Lavian, et al: In vivo extracelluler recording of sympatheic ganglion activity in a chronic animal model. Clin.Auton.Res. 2003;13 Suppl 1:183-188.

Leblais et al., "$\beta_3$-Adrenoceptor Control the Cystic Fibrosis Transmembrane Conductance Regulator through a cAMP/Protein Kinase A-independent Pathway," The Journal of Biological Chemistry, Mar. 5, 1999, pp. 6107-6113, vol. 274, No. 10, The American Society for Biochemistry and Molecular Biology, Inc., USA.

Lee, et al.: Effects of diacetyl monoxime and cytochalasin D on ventricular fibrillation in swine right ventricles. Am J Physiol 2001;280:H2689-96.

Lee, et al.: Patterns of wave break during ventricular fibrillation in isolated swine right ventricle. Am J Physiol 2001;281:H253-265.

Levi-Montalcini R: Growth control of nerve cells by a protein factor and its antiserum, Science 1964;143:105-110.

Li W. et al.; Infarction alters both the distribution and noradrenergic properties of cardiac sympathetic neurons. Am.J Physiol Heart Circ. Physiol 2004;286:H2229-36.

Lin, et al.; Slowing of intestinal transit by fat or peptide YY depends on a. beta-adrenergic pathway. Am J Physiol 2003;285(6):G1310-6.

Lindholm, et al.: Interleukin-1 regulates synthesis of nerve gowth factor in non-neuronal cells of rat sciatic nerve. Nature 1987;330:658-659.

Liu, et al.: Coexistenoe of two types of ventricular fibrillation during acute regional ischemia in rabbit ventricle. J Cardiovasc Electrophysiol 2004;15:1433-1440.

Liu et al.: Spatiotemporal correlation between phase singularities and wavebreaks during ventricular fibrillation. J Cardiovasc Electrophysiol 2003;14:1103-1109.

Liu, et al.: Sympathetic nerve sprouting, electrical remodeling and increased vulnerability to ventricular fibrillation in hypercholesterolemic rabbits. Circ Res 2003;92; 1145-1152.

Lowell et al., "The Potential Siglificance of $\beta_3$ Adrenergic Receptors," The Journal of Clinical Investigation, Mar. 1995, p. 923, vol. 95, No. 3, American Society for Clinical Investigation, Inc., The Rockefeller University Press, USA.

Lucchesi, et al.: Pharmacological modification of arrhythmias after experimentally induced acute myocardial infarction. Drugs acting on the nervous system. Circulation 1975;52:III241-III247.

Maisel, et al.: Externalization of beta-adrenergic receptors promoted by myocardial ischemia. Science 1985;230:183-186.

Malik, et al.: Depressed heart rate variability identifies postinfarction patients who might benefit from prophylactic treatment with amiodarone: a substudy of EMIAT (The European Myocardial Infarct Amiodarone Trial). J Am Coil Cardiol 2000;35:1263-1275.

Malkin, et al.: The effect of inducing ventricular fibrilation with 50-hz pacing versus T wave simulation on the ability to defibrillate. PACE, 21:1093-1097 (May 1998).

Mallavarapu, et al.: Circadian variation of ventricular arrhythmia recurrences after cardioverter-defibrillator implantation in patients with healed myocardiol infarcts. Am J Cardiol 1995;75:1140-1144.

Malpas SC: The rhythmicity of-sympathetic nerve activity. Prog. Neurobiol. 1998;56:65-96.

Marks, "Cardiac Intracellular Calcium Release Channels: Role in Heart Failure," Circulation Research, 2000, pp. 8-11, vol. 87, American Heart Association, USA.

(56) References Cited

OTHER PUBLICATIONS

Marron et al., "Distribution, Morphology, and Neurochemistry of Endocardial and Epicardial Nerve Terminal Arborizations in the Human Heart," Oct. 15, 1995, pp. 2343-2351, vol. 92, No. 8, American Heart Association, USA.

Menasche, et al.: Autologous skeletal myoblast transplantation for severe postinfarction left ventricular dysfunction. J Am Coll Cardiol 2003;41:1078-1083.

Merillat et al., "Robe of Calcium and the Calcium Channel in the Initiation and Maintenance of Ventricular Fibrillation," Circulation Research, Nov. 1990, pp. 1115-1123, vol 67, No. 5, American Heart Association, USA.

Merit-HF Study Group, "Effect of metoprolol CR/XL in chronic heart failure: Metoprolol CR/XL Randomised Intervention Trial in Congestive Heart Failure (MERIT-HF)," The Lancet, Jun. 12, 1999, pp. 2001-2007, vol. 353, UK.

Middlekauff, et al.: Morning sympathetic nerve activity is not increased in humans: Implications for mechanisms underlying the circadian pattern of cardiac risk. Circulation 1995;91:2549-2555.

Miknyoczki et al., "The Neurotrophin-Trk Receptor Axes are Critical for the Growth and Progression of Human Prostatic Carcinoma and Pancreatic Ductal Adenocarcinoma Xenografts in Nude Mice," Clinical Cancer Research, Jun. 2002, pp. 1924-1931, vol. 8.

Minardo, et al.: Scintigraphic and electrophysiological evidence of canine myocardial sympathetic denervation and reinnervation produced by myocardial infarction or phenol application. Circulation 1988;78:1008-1019.

Miyauchi, et al.: Altered atrial electrical restitution and heterogeneous sympathetic hyperinnervation in hearts with chronic left ventricular myocardial infarction: implications to atrial fibrillation. Circulation 2003;18:360-366.

Moïse et al., "An Animal Model of Spontaneous Arrhythmic Death," Journal of Cardiovascular Electrophysiology, Jan. 1997, pp. 98-103, vol. 8.

Moniotte et al., "Upregulation of $\beta_3$-Adrenoceptors and Altered Contractile Response to Inotropic Amines in Human Failing Myocardium," Circulation, 2001, pp. 1649-1655, vol. 103, American Heart Association, USA.

Mukherjee, et al.: Beta adrenergic and muscarinic cholinergic receptors in canine myocardium. Effects of ischemia. J.Clin.Invest 1979;64:1423-1428.

Mukherjee, et al.: Relationship between beta-adrenergic receptor numbers and physiological responses during experimental canine myocardial ischemia. Cir.Res. 1982;50:735-741.

Muller, et al.: Circadian variation in the frequency of sudden cardiac death. Circulation 1987;75:131-138.

Myerburg et al., "Frequency of Sudden Cardiac Death and Profiles of Risk," The American Journal of Cardiology, Sep. 11, 1997, pp. 10F-19F, vol. 80 (5B), Excerpts Medica, Inc., USA.

Nademanee, et al: Treating electrical storm: sympathetic blockade versus advanced cardiac life support-guided therapy. Circulation 2000;102:742-747.

Nitta, et al.: Propentofylline prevents neuronal dysfunction induced by infusion of anti-nerve growth factor antibody into the rat septum. Eur.J Pharmacol. 1996;307:1-6.

Nori, et al.: Immunohistochemical evidence for sympathetic denervation and reinnervation after necrotic injury in rat myocardium. Cell Mol Biol 1995;41:799-807.

Oh et al., "Relationship between nerve sprouting and neurotrophic gene expression in a mouse model of myocardial infarction," Heart Rhythm, May Supp. 2004, p. S191, Abstract No. 608, vol. 1, No. 1.

Oh, et al.: Scar formation after ischemic myocardial injury in MRL mice. Cardiovasc Pathol 2004;13:203-6.

Ohara, et al.: Downregulation of Immunodetectable Atrial Connexin40 in a Canine Model of Chronic Left Ventricular Myocardial Infarction: Implications to Atrial Fibrillation. J. Cardiovasc Pharmacol Ther 2002;7:89-94.

Ohara et al.: Increased vulnerability to inducible atrial fibrillation caused by partial cellular uncoupling with heptanol. Am J Physiol 2002;283:H1116-1122.

Ohara, et al.: Increased wave break during ventricular fibrillation in the epicardial border zone of hearts with healed myocardial infarction. Circulation 2001;103 1465-1472.

Ohyanagi, et al: Beta-adrenergic receptors in ischemic and nonischemic canine myocardium: relation to ventricular fibrillation and effects of pretreatment with propranolol and hexamethonium. J.Cardiovasc.Pharmacol. 1988;11:107-114.

Okin, et al; Assessment of QT Interval and QT Dispersion for Prediction of All-Cause and Cardiovascular Mortality in American Indians: The Strong Heart Study. Circulation 2000;101:61-66.

Okuyama, et al.: High resolution mapping of the pulmonary vein and the vein of marshall during induced atrial fibrillation and atrial tachycardia in a canine model of pacing-induced congestive heart failure. J Am Coll Cardiol 2003;42:348-60.

Okuyama, et al.: Nerve sprouting induced by radiofrquency catheter ablation in dogs. Heart Rhythm 2004;1;712-7.

Omichi et al., "Transmembrane $Ca^{2+}$ Transients and Action Potential During Restitution are Two Independent but Coupled Phenomena in Ventricular Fibrillation," Supplement to Circulation, Abstracts from Scientific Sessions 2000, Oct. 31, 2000, p. 1672, vol. 102, No. 18, American Heart Association, USA.

Omichi, et al.: Comparing cardiac action potentials recorded with metal and glass microelectrodes. Am J Physiol 2000 279;H3113-3117.

Omichi, et al.: Demonstration of electrical and anatomical connections between Marshall bundles and left atrium in dogs: implications on the generation of P waves on surface electrocardiogram. J Cardiovasc Electrophysiol 2002;13:1283-1291.

Omichi, et al.; Effects opf amiodarone on wave front dynamics during ventricular fibrillation in isolated swine right ventricle. Am J Physiol 2002;282:H1063-1070.

Omichi, et al.: Intracellular Ca dynamics in ventricular fibrillation. Am J Physiol 2004;286:H1836-H1844.

Packer et al.,"The Effect of Carvedilol on Morbidity and Mortality in Patients with chronic Heart Failure," The New England Journal of Medicine, May 23, 1996, pp. 1349-1355, vol. 334, No. 21, Massachusetts Medical Society, Boston, MA, USA.

Pak, et al.: Catheter ablation of ventricular fibrillation in rabbit ventricles treated with beta-blockers, Circulation 2003;108:3149-56.

Pak, et al.: Improvement of ventricular defibrillation efficacy with pre-shock synchronized pacing. J Cardiovasc Electrophysiol 2004; 2004;15:581-587.

Pak, et al.: Mesenchymal stem cell injection induces cardiac nerve sprouting and increased tenascin expression in swine model of myocardial infarction. J Cardiovasc Electrophysiol. 2003;14:841-48.

Pak, et al.: Synchronization of ventricular fibrillation with real-time feedback pacing: Implication to low-energy defibrillation. Am J Physiol 2003;285:H2704-2711.

Park, et al.: Distribution of cardiac nerves in patients with diabetes mellitus: an immunohistochemical postmortem study of human hearts. Cardiovasc Path 2002;11:326-331.

Park, et al.: Thoracic vein ablation terminates chronic atrial fibrillation in dogs. Am J Physiol Heart Circ Physiol. 2004;286(6):H2072-7.

Parry, et al.: Incidence and functional significance of sympathetic reinnervation after cardiac transplantation. Transplant Proc 1997;29:569-570.

PCT International Search Report re PCT/US00/12367, mailed Aug. 11, 2000.

Peckova, et al.: Weekly and seasonal variation in the incidence of cardiac arrests. Am.Heart J. 1999;137:512-515.

Pedersen, et al.: The occurrence and prognostic significance of atrial fibrillation/-flutter following acute myocardial infarction. TRACE Study group. TRAndolapril Cardiac Evaluation. Eur Heart J 1999;20;748-754.

Perry, et al.: Later ventricular arrhythmia and sudden death following direct-current catheter ablation of the atrioventricular junction. Am.J.Cardiol. 1992;70-765-768.

Peters RW: Propranolol and the morning increase in sudden cardiac death: (the beta-blocker heart attack trial experience). Am.J.Cardiol. 1990;66:57G-59G.

Podio et al.: Regional Sympathetic denervation after myocardial infarction: a follow-up study using [123I]MIBG. Q J Nucl Med 1995;39:40-43.

(56) References Cited

OTHER PUBLICATIONS

Postma et al., "Absence of Calsequestrin 2 Causes Severe Forms of Catecholaminergic Polymorphic Ventricular Tachycardia," Circulation Research, 2002, pp. e21-e26, vol. 91, American Heart Association, USA.
Priori et al., "Clinical and Molecular Characteriation of Patients with Catecholaminergic Polymorphic Ventricular Tachycardia," Circulation, Jul. 2, 2002, pp. 69-74, vol. 106, American Heart Association, USA.
Qin, et al.: Loss of cardiac sympathetic neurotransmitters in heart failure and NE infusion is associated with reduced NGF. Am J Physiol Heart Circ Physiol 2002;282:H363-H371.
Qu, et al.: Mechanisms of discordant alternans and induction of reentry in a simulated cardiac tissue. Circulation 2000;102:1664-70.
Rathore, et al.: Acute myocardial infarction complicated by atrial fibrillation in the elderly: prevalence and outcomes. Circulation 2000;101:969-974.
Reiken et al., "β-Blockers Restore Calcium Release Channel Function and Improve Cardiac Muscle Performance in Human Heart Failure," Circulation, 2003, pp. 2459-2466, vol. 107, American Heart Association, Inc., USA.
Reiter, "β-Adrenergic Blocking Drugs as Antifibrillatory Agents," Current Cardiology Reports, 2002, pp. 426-433, vol. 4, Current Sciences, Inc.
Robinson, et al.: "Immunocytochemistry," Theory and Practice of Histological Techniques. Third Edition. Churchill Livingstone, Edinburgh London, Melbourne and New York, 1990, pp. 413-436.
Rodenbaugh et al., "Increased Susceptibility to Ventricular Arrhythmias in Hypertensive Paraplegic Rats," Clinical and Experimental Hypertension, 2003, pp. 349-358, vol. 25, Marcel Dekker, Inc., New York, NY, USA.
Rosenbaum, et al.: Predicting sudden cardiac death from T wave alternans of the surface electrocardiogram: promise and pitfalls. J.Cardiovasc.Electrophysiol. 1996;7:1095-1111.
Rush RA: Immunohistochemical localization endogenous nerve growth factor. Nature 1984;312:364-367.
Sanguinetti, et al.: Coassembly of K(V)LQT1 and minK (IsK) proteins to form cardiac 1(Ks) potassium channel. Nature 1996;384;80-83.
Schwartz PJ: QT prolongation, sudden death, and sympathetic imbalance: the pendulum swings. J Cardiovasc Electrophysiol 2001;12:1074-1077.
Schwartz, et al.: Autonomic mechanisms in ventricular fibrillation induced by myocardial ischemia during exercise in dogs with healed myocardial infarction. An experimental preparation for sudden cardiac death. PubMed Abstract of Circulation Apr;69(4):790-800 (1984).
Schwartz, et al.: Autonomic mechanisms and sudden death. New insights from analysis of baroreceptor reflexes in conscious dogs with and without a myocardial infarction. Circulation 1988;78:969-979.
Schwartz, et al.: Autonomic nervous system and sudden cardiac death: Experimental basis and clinical observations for post-myocardial infarction risk stratification. Circulation 1992;85:I-77-I-91.
Schwartz, et al.: Effects of unilateral stellate ganglion blockade on the arrhythmias associated with coronary occlusion. Am Heart J 1976;92:589-599.
Schwartz, et al.: Left cardiac sympathetic denervation in the management of high-risk patients affected by the long-QT syndrome, Circulation 2004;109:1826-1833.
Schwartz, et al.: Left cardiac sympathetic denervation in the therapy of congenital long QT syndrome, A worldwide report. Circulation 1991;84:503-511.
Schwartz, et al.: Prevention of sudden cardiac death after a first myocardial infarction by pharmacologic or surgical antiadrenergic interventions. J Cardiovasc Electrophysiol 1992;3:2-16.
Schwartz, et al.: Sympathetic nervous system and cardiac arrhythmias, in Zipes DP, Jalife J (eds): Cardiac Electrophysiology: From Cell to Bedside. Philadelphia, PA, W. B. Saunders Company, 1990, pp. 330-343.
Schwartz, et al.: The long QT syndrome, in Zipes DP, Jalife J (eds): Cardiac Electrophysiology: From Cell to Bedside, Philadelphia, W. B. Saunders Company, 1994, pp. 788-811.
Scoote et al., "The cardiac ryanodine receptor (calcium release channel): Emerging role in heart failure and arrhythmia pathogenesis," Cardiovascular Research, 2002, pp. 359-372, vol. 56, Elsevier Science B.V.
Shen et al., "Differences in $β_3$-Adrenergic Receptor Cardiovascular Regulation in Conscious Primates, Rats and Dogs," The Journal of Pharmacology and Experimental Therapeutics, 1996, pp. 1435-1443, vol. 278, No. 3, The American Society for Pharmacology and Experimental Therapeutics, USA.
Shimizu, et al.: Cellular basis for the ECG features of the LQT1 form of the long-QT syndrome: effects of beta-adrenergic agonists and antagonists and sodium channel blockers on transmural dispersion of repolarization and torsade de pointes. Circulation 1998;98:2314-2322.
Shimizu, et al.: Differential effects of beta-adrenergic agonists and antagonists in LQT1, LQT2 and LQT3 models of the long QT syndrome. J Am Coll Cardiol 2000;35:778-786.
Shimizu, et al.: Sympathetic modulation of the long QT syndrome, Eur.Heart J. 2002;23:1246-1252.
Shivkumar, et al.: Sudden death after heart transplantation; the major mode of death. J Heart Lung Transplant 2001;20:180(abstract).
Sjoberg, et al.: The initial period of peripheral nerve regeneration and the importance of the local environment for the conditioning leison effect. Brain Res 1990;529:79-84.
Sosunov et al., "Abnormal cardiac repolarization and impulse initiation in German shepherd dogs with inherited ventricular arrhythmias and sudden death," Cardiovascular Research, 1999, pp. 65-79, vol. 42, Elsevier Science B.V.
Stanton, et al.: Regional sympathetic denervation after myocardial infarction in humans detected noninvasively using I-123-metaiodobenzylguanidine. J Am Coll Cardiol 1989;14:1519-1526.
Strasser, et al.: Sensitization of the beta-adrenergic system in acute myocardial ischaemia by a protein kinase C-dependent mechanism. Eur.Heart J. 1991;12 Suppl F:48-53.
Strohmer, et al.: Radiofrequency ablation of focal atrial tachycardia and atrioatrial conduction from recipient to donor after orthotopic heart transplantation. J Cardiovasc Electrophysiol 2000;11:1165-9.
Strohmer, et al.: Selective atrionodal input ablation for induction of proximal complete heart block with stable junctional escape rhythm in patients with uncontrolled atrial fibrillation. J Interv Card Electrophysiol 2003;8:49-57.
Sutula, et al.: Mossy fiber synaptic reorganization in the epileptic human temporal lobe. Ann Neurol 1989;26:321-330.
Sutula, et al.: Synaptic reorganization in the hippocampus induced by abnormal functional activity. Science 1988;239-1147-1150.
Swan, et al.: Sinus node function and ventricular repolarization during exercise stress test in long QT syndrome patients with KvLQT1 and HERG potassium channel defects. J Am Coll Cardiol 1999;34:823-829.
Swissa et al., "Long-Term Subthreshold Electrical Stimulation of the Left Stellate Ganglion and Canine Model of Sudden Cardiac Death," Journal of the American College of Cardiology, Mar. 3, 2004, pp. 858-864, vol. 43, No. 5, Elsevier Inc., USA.
Swissa, et al.: Sildenafil-nitric oxide donor combination promotes ventricular tachyarrhythmias in the swine right ventricle. Am J Physiol 2002;282:H1787-1792.
Swissa, et al.: Action potential duration restitution and ventricular fibrillation due to rapid focal excitation. Am J Physiol 2002;282:H1915-1923.
Takei, et al.: The autonomic control of the transmural dispersion of ventricular repolarization in anesthetized dogs. J Cardiovasc Electrophysiol 1999;10:981-989.
Task Force, et al.: Heart rate variability—standards of measurement, physiological interpretation, and clinical use. Circulation 1996;93:1043-1065.
Tato, et al.: Effects of right stellate ganglion stimulation on regional myocardial blood flow and ischemic injury in dogs. Eur.J Pharmacol. 1981;71:223-232.
Tavernier et al., "The Positive Chronotropic Effect Induced by BRL 37344 and CGP 12177, Two Beta-3 Adrenergic Agonists, Does Not

(56) References Cited

OTHER PUBLICATIONS

Involve Cardiac Beta Adrenoceptors but Baroreflex Mechanisms," The Journal of Pharmacology and Experimental Therapeutics, Dec. 1992, pp. 1083-1090, vol. 263, No. 3, The American Society for Pharmacology and Experimental Therapeutics, Williams & Wilkins, USA.
Tavernier et al., "$\beta_3$-Adrenergic stimulation produces a decrease of cardiac contractility ex vivo in mice overexpressing the human $\beta_3$-adrenergic receptor," Cardiovascular Research, 2003, pp. 288-296, vol. 59, European Society of Cardiology, Elsevier B.V.
Thandroyen, et al.: Alterations in beta-adrenergic receptors, adenylate cyclase, and cyclic AMP concentrations during acute myocardial ischemia and reperfusion. Circulation 1990;82:II30-II37.
Tsai, et al.; T-wave alternans as a predictor of spontaneous ventricular tachycardia in a canine model of sudden cardiac death. J Cardiovasc Electrophsiol 2002;13:51-55.
Uchida, et al.: Sustained decrease in coronary blood flow and excitation of cardiac sensory fibers following sympathetic stimulation. Jpn.Heart J 1975;16:265-279.
Ure: Retrograde transport and steady-state distribution of 125I-nerve growth factor in rat sympathetic neurons in compartmented cultures. J.Neurosci. 1997;17:1282-1290.
Ursell et al., "Anatomic Distribution of Autonomic Neural Tissue in the Developing Dog Heart: I. Sympathetic Innervation," The Anatomical Record, Jan. 1990, pp. 71-80, vol. 226, No. 1, American Association of Anatomists, Wiley-Liss, USA.
Valderrábano et al., "Dynamics of Intramural and Transmural Reentry During Ventricular Fibrillation in Isolated Swine Ventricles," Circulation Research, Apr. 27, 2001, pp. 839-848, vol. 88, American Heart Association, Inc., USA.
Valderrá bano, et al.: Obstacle-Induced transition from ventricular fibrillation to tachycardia in isolated swine right ventricles: Insights into the transition dynamics and implications for the critical mass. J Am Coll Cardiol 2000;36:2000-8.
Valderrábano, et al.: Spatial distribution of phase singularities in ventricular fibrillation, Circulation 2003;108:354-359.
Valderrábano, et al: Frequency analysis of ventricular fibrillation in swine ventricles Cir Res 2002;90:213-222.
Varghese et al., "$\beta_3$-adrenoceptor deficiency blocks nitric oxide-dependent inhibition of myocardial contractility," The Journal of Clinical Investigation, Sep. 2000, pp. 697-703, vol. 106, No. 5, American Society for Clinical Investigation, USA.
Vassalle, et al.: The effect of adrenergic enhancement on overdrive excitation. J.Electrocardiol. 1976;9:335-343.
Verrier, et al.: Ventricular vulnerability during sympathetic stimulation: role of heart rate and blood pressure. Cardiovasc Res 1974;8:602-610.
Viskin, et al.: Circadian variation of symptomatic paroxysmal atrial fibrillation, Data from almost 10 000 episodes. Eur Heart J 1999;20:1429-1434.
Vleeming et al., "Density of β adrenoceptors in rat heart and lymphocytes 48 hours and 7 days after acute myocardial infarction," Cardiovascular Research, 1989, pp. 859-866, vol. 23.
Voroshilovsky, et al.: Mechanisms of ventricular fibrillation induction by 60 Hz alternating current in isolated swine right ventricle. Circulation 2000;102:1569-1574.
Vracko, et al.: Fate of nerve fibers in necrotic, healing, and healed rat myocardium, Lab Invest 1990;63:490-501.
Vracko, et al.: Nerve fibers in human myocardial scars, Hum Pathol 1991;22:138-146.
Wang, et al.: Optical mapping of ventricular defibrillation in isolated swine right ventricles: demonstration of postshock isoelectric window after near-threshold defibrillation shocks, Circulation 2001;104 227-233.
Willich, et al.: Circadian variation in the incidence of sudden cardiac death in the Framingham Heart Study Population. Am J Cardiol 1987;60:801-806.
Wisser, et al.: Circadian changes of clinical chemical endocrinological parameters. J.Clin.Chem.Clin.Biochem. 1981;19:323-337.
Wood, et al.: Circadian pattern of ventricular tachyarrhythmias in patients implantable cardioverter-defibrillators. J Am Coll Cardiol 1995;25:901-907.
Wu TJ, et al.: Mother rotors and the mechanisms of D600-induced type 2 ventricular fibrillation. Circulation, 2004;110:2110-2118.
Wu TJ, et al.: Progressive action potential duration shortening and the conversion from atrial flutter to atrial fibrillation in isolated canine right atrium, J Am Coll Cardiol 2001:38:1757-1765.
Wu TJ, et al.: Simultaneous biatrial computerized mapping during permanent atrial fibrillation in patients with organic heart diseases. J Cardiovasc Electrophsiol 2002;13:571-577.
Wu, et al.: Pulmonary veins and ligament of Marshall as sources of rapid activations in a canine model of sustained atrial fibrillation. Circulation 2001:103:1157-1163.
Wu, et al.: Two types of ventricular fibrillation in isolated rabbit hearts: importance of excitability and action potential duration restitution. Circulation 2002;106:1859-1866.
Yamashita, et al.: Circadian variation of cardiac K+ channel gene expression. Circulation 2003;107:1917-1922.
Yambe, et al.: Vagal nerve activity and the high frequency peak of the heart rate variability. Int.J.Artif.Organs 1999;22:324-328.
Yambe, et al.: Vegal nerve activity recording in the awake condition for the control of an artificial heart system. Artif.Organs 1999;23:529-531.
Yanowitz, et al.; Functional distribution of right and left stellate innervation to the ventricles. Production of neurogenic electrocardiographic changes by unilateral alteration of sympathetic tone. Cir Res 1966;18:416-428.
Yashima, et al.; Nicotine increases ventricular vulnerability to fibrillation in hearts with healed myocardial infarction. Am J Physiol (Heart and Circulatory Physiology) 2000; 278:H2124-33.
Yashima, et al.; On the Mechanism of the Probabilistic Nature of Ventricular Defibrillation Threshold, Am J Physiol 2003;284:H249-255.
Yip, et al.: Retrograde transport of nerve growth factor in lesioned goldfish retinal ganglion cells. J Neurosci. 1983;3:2172-2182.
Zhou, et al.: Low-affinity NGF receptor p75NTR immunoreactivity in the myocardium with sympathetic hyperinnervation. J Cardiovasc Electrophysiol 2004;15:430-7.
Zhou, et al.: Mechanisms of cardiac nerve sprouting after myocardial infarction in dogs. Circ Res 2004;95:76-83.
Zhou, et al.: Modulation of QT interval by cardiac sympathetic nerve sprouting and the mechanisms of ventricular arrhythmia in canine model of sudden cardiac death. J Cardiovasc Electrophsiol 2001;12:1068-73.
Zhou, et al.: Nonreentrant focal activations in pulmonary veins in canine model of sustained atrial fibrillation. Am J Physiol 2002;283:H1244-1252.
Zhou, et al.: Satellite-cell-derived nerve growoth factor and neurotrophin-3 are involved in norandrenergic sprouting in the dorsal root ganglia following peripheral nerve injury in the rat. Eur J Neurosci. 1999;11:1711-1722.
Zhou, et al.: Torsade de pointes and sudden death induced by thiopental and isoflurance anesthesia in dogs with cardiac electrical remodeling. J Cardiovasc Pharmacol Ther 2002;7:39-43.
Zipes et al., "Sudden Cardiac Death," Circulation, Nov. 24, 1998, pp. 2334-2351, vol. 98, No. 21, American Heart Association, USA.
Adrian, et al.: Discharges in mammalian sympathetic nerves. J Physiol 1932;74:115-133.
Akingba, et al.: Application of nanoelectrodes in recording biopotentials. Nanotechnology, 2003, IEEE-NANO 2003;2:870-874.
Akira, et al: Induction of atrial fibrillation and nerve sprouting by prolonged left atrial pacing in dogs. PACE 2003;26:2247-2252.
Anthonio et al., "β-Adrenoceptor density in chronic infarcted myocardium: a subtype specific decrease of $\beta_1$-adrenoceptor density," International Journal of Cardiology, 2000, pp. 137-141, vol. 72, Elsevier Science Ireland Ltd., Ireland.
Armour JA: Activity of in situ middle cervical ganglion neurons in dogs, using extracellular recording techniques. Can.J Physiol Pharmacol. 1985;63:704-716.
Armour, et al.: Activity of canine in situ left atrial ganglion neurons. Am.J Physiol 1990;259:H1207-H1215.

(56) References Cited

OTHER PUBLICATIONS

Armour, et al.: Activity of in vivo canine ventricular neurons. Am.J Physiol 1990;258:H326-H336.
Aronow, et al.: Circadian variation of primary cardiac arrest or sudden cardiac death in patients aged 62 to 100 years (mean 82). Am J Cardiol 1993;71:1455-1456.
Athill, et al.: Influence of wavefront dynamics on transmembrane potential characaterstics during atrial fibrillation. J Cardiovasc Electrophysiol 2000;11:913-921.
Barbacid M: Nerve growth factor: a tale of two receptors, Oncogene 1993;8:2033-2042.
Barber, et al.: Interruption of sympathetic and vagal-mediated afferent responses by transmural myocardial infarction. Circulation 1985;72:623-631.
Barhanin, et al.: K(V)LQTI and IsK (minK) proteins associate to form the I(Ks) cardiac potassium current. Nature 1996;384:78-80.
Barrett, et al.: What sets the long-term level of renal sympathetic nerve activity: a role for angiotensin II and baroreflexes? Cir.Res. 2003;92:1330-1336.
Bartels et al., "Influences of Myocardial Ischemia and Reperfusion on β-Adrenoceptor Subtype Expression," Journal of Cardiovascular Pharmacology, 1998, pp. 484-487, vol. 31, Lippincott-Raven Publishers, Philadelphia, PA, USA.
Blakey, et al.: Sudden, unexpected death in cardiac transplant recipients: an autopsy study. J Heart Lung Transplant 2001;20:229(abstract).
Bonnemeier, et al.: Course and prognostic implications of QT interval and QT interval variability after primary coronary angioplasty in acute myocardial infarction. J Am Coll Cardiol 2001;37:44-50.
Bosch et al., "$β_3$-Adrenergic regulation of an ion channel in the heart-inhibition of the slow delayed rectifier potassium current $I_{Ka}$ in guinea pig ventricular myocytes," Cardiovascular Research, 2000, pp. 393-403, vol. 56, Elsevier Science B.V.
Bristow et al., "$β_1$- and $β_2$-Adrenergic-Receptor Subpopulations in Nonfailing and Failing Human Ventricular Myocardium: Coupling of Both Receptor Subtypes to Muscle Contraction and Selective $β_1$-Receptor Down-Regulation in Heart Failure," Circulation Research, Sep. 1986, pp. 297-309, vol. 59, No. 3, American Heart Association, USA.
Bristow et al., "$β_1$- and $β_2$-Adrenergic-Receptor-Mediated Adenylate Cyclase Stimulation in Nonfailing and Failing Human Ventricular Myocardium," Molecular Pharmacology, Mar. 1989, pp. 295-303, vol. 35, No. 3, American Society for Pharmacology and Experimental Therapeutics, Williams & Wilkins, USA.
Brodde et al., "Adrenergic and Muscarinic Rceptors in the Human Heart," Pharmacological Reviews, 1999, pp. 651-689, 0031-6997/99/5104-0651, The American Society for Pharmacology and Experimental Therapeutics, USA.
Brodde et al., "β-Adrenoceptors in the transplanted human heart: unaltered β-adrenoceptor density, but increased proporation of $β_2$-adrenoceptors with increasing posttransplant time," Naunyn-Schmiedeberg's Arch. Pharmacol., 1991, pp. 430-436, vol. 344, Springer-Verlag.
Cao JM, et al.: Nerve sprouting and sudden cardiac death, Circ Res 2000 86: 816-821.
Cao JM, et al: Relationship between regional cardiac hyperinnervation and ventricular arrhythmia. Circulation 200;101:1960-1969.
Centers for Disease Control and Prevention: State-specific mortality from sudden cardiac death—United States, 1999, MMWR Morb. Mortal.Wkly.Rep. 2002;51:123-126.
Cesario, et al.: Electrophysiological characterization of cardiac veins in humans. J Interventional Cardiac Electrophysiol 2004;10:241-7.
Chaudhry et al., "Differential Interaction of $β_1$-and $β_3$-Adrenergic Receptors with $G_1$ in Rat Adipocytes," Cellular Signalling, 1994, pp. 457-465, vol. 6, No. 4, Elsevier Science Ltd., Great Britain.
Chen, et al.: Sympathetic nerve sprouting, electrical remodeling and the mechanisms of sudden cardiac death. Cardiovasc Res 2001;50:409-416.
Cheng, et al.: Upregulation of functional beta(3)-adrenergic receptor in the failing canine myocardium. Circ Res 2001;89:599-606.
Chou, et al.: Effects of procainamide on electrical activity in the thoracic veins and the atria in canine model of sustained atrial fibrillation. Am J Physiol 2004;286:H1936-H1945.
Chou, et al.: Marshall bundle and the valve of Vieussens. J Cardiovasc Electrophysiol 2003;14:1254.
Dae et al., "Heterogeneous Sympathetic Innervation in German Shepherd Dogs With Inherited Ventricular Arrhythmia and Sudden Cardiac Death," Circulation, Aug. 19, 1997, pp. 1337-1342, vol. 96, No. 4, American Heart Association, USA.
Dae, et al.: Scintigraphic assessment of MIBG uptake in globally denervated human and canine hearts—implications for clinical studies, J Nucl Med 1992;33:1444-1450.
Doshi, et al.: Initial experience with an active-fixation defibrillation electrode and the presence of nonphysiological sensing. PACE 2001;24:1713-20.
Duff et al., "Electrophysiologic Actions of High Plasma Concentrations of Propranolol in Human Subjects," Journal of the American College of Cardiology, Dec. 1983, pp. 1134-1140, vol. 2, No. 6, American College of Cardiology, Elsevier Biomedical, USA.
Eckardt et al., "Arrhythmiasin Heart Failure: Current Concepts ofr Mechnisms and Therapy," Joujrnal of Cardiovascular Electrophysiology, Jan. 2000, pp. 106-117, vol. 11, No. 1, Futura Publishing Company Inc., Armonk, NY, USA.
Edvardsson et al., "Effects of acute and chronic beta-receptor biockade on ventricular repolarisation man," British Heart Journal, Jun. 1981, pp. 628-636, vol. 45, No. 6, British Medical Association, UK.
Eldar, et al.: Significance of paroxysmal atrial fibrillation complicating acute myocardial infarction in the thromobolytic era. SPRINT and thrombolytic Survey Groups, Circulation 1998;97:965-970.
Farrukah et al., "Up-Regulation of $Beta_2$-Adrenergic Receptor in Previously Transplanted, Denervated Nonfailing Human Hearts," Journal of the American College of Cardiology, Dec. 1993, pp. 1902-1908, vol. 22, No. 7, Elsevier, USA.
Fozzard, "Afterdepolarizations and triggered activity," Supplement to Basic Research in Cardiology, 1992, pp. 105-113, vol. 87, Suppl. 2, Steinkopff Verlag Darmstadt Springer-Verlag, New York, NY, USA.
Freemantle et al., "β Blockade after myocardial infarction: systematic review and meta regression analysis," BMJ, Jun. 26, 1999, pp. 1730-1737, vol. 318, UK.
Garfinkel, et al.: Preventing ventricular fibrillation by flattening cardiac restitution. Proc Natl Acad Sci U S A 2000;97:6061-66.
Gauthier, et al.: Functional beta3-adrenoceptor in the human heart. J Clin Invest 1996;98-556-562.
Ginty DD, Segal RA: Retrograde neurotrophin signaling: Trk-ing along the axon. Curr.Opin.Neurobiol. 2002:12:268-274.
Goldberg, et al.: Impact of atrial fibrillation on the in-hospital and long-term survival of patients with acute myocardial infarction: A community-wide perspective. Am Heart J 1990;119:996-1001.
Gottlieb et al., "Effect of Beta-Blockade on Mortality Among High-Risk and Low-Risk Patients After Myocardial Infarction." The New England Journal of Medicine, Aug. 20, 1998, pp. 489-497, vol. 339, No. 8, Massachusetts Medical Society, Boston, MA, USA.
Guth L: Regeneration in the mammalian peripheral nervous system. Physiol Rev 1956;36:441-478.
Hamabe, et al.: Correlation between anatomy and electrical activation in canine pulmonary veins, Circulation 2003;107:1550-1555.
Hamzei, et al.: The role of approximate entropy in predicting ventricular defibrillation threshold. J Cardiovasc Pharmacol Ther 2002;7:45-52.
Harding et al., "Lack of evidence for β3-adrenoceptor modulation of contractile function in human ventricular myocytes," Supplement to Circulation, Abstracts from the $70^{th}$ Scientific Sessions, Nov. 9-12, 1997, p. 284, vol. 96, No. 8, American Heart Association, USA.
Hassankhani, et al: Overexpression of NGF within the heart of transgenic mice causes hyperinnervation, cardiac enlargement, and hyperplasia of ectopic cells. Dev Biol 1995:169-309-321.
Hayashi H, et al.: Effects of cytochalasin D on electrical, restitution and the dynamics of ventricular fibrillation in isolated rabbit heart. J Cardiovasc Electrophysiol 2003:14:1077-1084.
Hom et al., "$β_3$-Adrenoceptor Agonist-Induced Increases in Lipolysis, Metabolic Rate, Facial Flushing, and Reflex Tachycardia

(56) References Cited

OTHER PUBLICATIONS in Anesthetized Rhesus Monkeys," The Journal of Pharmacology and Experimental Therapeutics, 2001, pp. 299-307, vol. 297, American Society for Pharmacology and Experimental Therapeutics.

Hume, et al.: Chloride conductance pathways in heart. Am J Physiol 1991;261:C399-C412.

Ieda, et al.: Endothelin-1 regulates cardiac sympathetic innervation in the rodent heart by controlling nerve growth factor expression. J.Clin. Invest 2004;113:876-884.

Ihl-Vahl et al., "Differential Regulation of mRNA Specific for $\beta_1$- and $\beta_2$-adrenergic Receptors in Human Failing Hearts. Evaluation of the Absolute Cardiac mRNA Levels by Two Independent Methods," J. Mol. Cell. Cardiol., 1996, pp. 1-10, vol. 28, Academic Press Limited.

Ihl-Vahl et al., "Regulation of β-Adrenergic Receptors in Acute Myocardial Ischemia: Subtype-selective increase of mRNA Specific for $\beta_1$-Adrenergic Receptors," J. Mol. Cell. Cardiol., 1995, pp. 437-452, vol. 27, Academic Press Limited.

Janse, et al: Effect of unilateral stellate ganglion stimulation and ablation on electrophysiologic changes induced by acute myocardial ischemia in dogs. Circulation 1985;72:585-595.

Josephson, et al.: The beta subunit increases Ca2+ currents and gating charge movements of human cardiac L-type Ca2+ channels. Biophys J 1996:70:1285-1293.

Kathofer, et al.: Functional coupling of human beta 3-adrenoreceptors to the KvLQT1/MinK potassium channel. J Biol Chem 2000;275:26743-26747.

Kaye, et al.: Reduced myocardial nerve growth factor expression in human and experimental heart failure. Cir Res 2000;86:E80-E84.

Kim, et al.: Sympathetic nerve sprouting after orthotopic heart transplantation. J. Heart Lung Transplantation 2004,23:1349-1358.

Kim, et al.: The Ligament of Marshall: A structural analysis in human hearts with implications for atrial arrhythmias. J Am Coll Cardiol. 2000;36:1324-7.

Kleiger, et al.: Decreased heart rate variability and its association with increased mortality after acute myocardial infarction. Am J Cardiol 1987;59:256-262.

Kohout et al., "Augmentation Cardiac Contractility Mediated by the Human $\beta_3$-Adrenergic Receptor Overexpressed in the Hearts of Transgenic Mice," Circulation, Nov. 13, 2011, pp. 2485-2491, vol. 104, The American Heart Association, USA.

Korsching S: The neurotrophic factor concept: a reexamination. J.Neurosci. 1993;13:2739-2748.

Kotzbauer, et al.: Postnatal development of survival responsiveness in rat sympathetic neurons to leukemia inhibitory factor and ciliary neurotrophic factor. Neuron 1994;12:763-773.

La Rovere, et al.: Baroreflex sensitivity and heart rate variability in the identification of patients at risk for life-threatening arrhythmias: implications for clinical trials. Circulation 2001;103:2072-2077.

Lai, et al.: Co-localization of tenascin and sympathetic nerves in canine model of nerve sprouting and sudden cardiac death. J Cardiovasc Electrophysiol 2000:11:1345-51.

Lampert, et al.: Circadian variation of sustained ventricular tachycardia in patients with coronary artery disease and implantable cardioverter-defibrillators. Circulation 1994;90:241-247.

Lavian, et al: In vivo extracellular recording of a sympathetic ganglion activity in a chronic animal model. Clin.Auton.Res. 2003;13 Suppl 1:183-188.

Leblais et al., "$\beta_3$-Adrenoceptor Control the Cyctic Fibrosis Transmembrane Conductance Regulator through a cAMP/Protein Kinase A-independent Pathway," The Journal of Biological Chemistry, Mar. 5, 1999, pp. 6107-6113, vol. 274, No. 10, The American Society for Biochemistry and Molecular Biology, Inc., USA.

Lee, et al.: Patterns of wave break during ventricular fibrillation in isolated swine right ventricle, Am J Physiol 2001;281:H253-265.

Li W, et al.: Infarction alters both the distribution and noradrenergic properties of cardiac sympathetic neurons. Am.J Physiol Heart Circ. Physiol 2004;286:H2229-36.

Lin, et al.: Slowing of intestinal transit by fat or peptide YY depends on a beta -adrenergic pathway. Am J Physiol 2003;285(6):G1310-6.

Lindholm, et al.: Interleukin-1 regulates synthesis of nerve growth factor in non-neuronal cells of rat sciatic nerve. Nature 1987;330:658-659.

Liu, et al.: Coexistence of two types of ventricular fibrillation during acute regional ischemia in rabbit ventricle. J Cardiovasc Electrophysiol 2004;15:1433-1440.

Liu, et al.: Spatiotemporal correlation between phase singularities and wavebreaks during ventricular fibrillation. J Cardiovasc Electrophysiol 2003;14:1103-1109.

Liu, et al.: Sympathetic nerve sprouting electrical remodeling and increased vulnerability to ventricular fibrillation in hypercholesterolemic rabbits. Circ Res 2003;92: 1145-1152.

Lowell et al., "The Potential Significance of $\beta_3$ Adrenergic Receptors," The Journal of Clinical Investigation, Mar. 1995, p. 923, vol. 95, No. 3, American Society for Clinical Investigation, Inc., The Rockefeller University Press, USA.

Lucchesi, et al.: Pharmacocogical modification of arrhythmias after experimentally induced acute myocardial infarction. Drugs acting on the nervous system. Circulation 1975;52:III241-III1247.

Maisel, et al.; Externalization of beta-adrenergic receptors promoted by myocardial ischemia. Science 1985;230:183-186.

Malik, et al.: Depressed heart rate variability identifies postinfarction patients who might benefit from prophylactic treatment with amiodarone: a substudy of EMIAT (The European Myocardial Infarct Amiodarone Trial). J Am Coll Cardiol 2000;35:1263-1275.

Malkin et al.: The effect of inducing ventricular fibrilation with 50-hz pacing versus T wave simulation on the ability to defibrillate. PACE, 21:1093-1097 (May 1998).

Mallavarapu, et al.: Circadian variation ventricular arrhythmia recurrences after cardioverter-defibrillator implantation in patients with healed myocardiol infarcts. Am J Cardiol 1995;75:1140-1144.

Malpas SC: The rhythmicity of sympathetic nerve activity. Prog. Neurobiol. 1998;56:65-96.

Merillat et al., "Role of Calcium and the Calcium Channel in the Initiation and Maintenance of Ventricular Fibrillation," Circulation Research, Nov. 1990, pp. 1115-1123, vol. 67, No. 5, American Heart Association, USA.

Miyauchi, et al.: altered atrial electrical restitution and heterogeneous sympathetic hyperinnervation in hearts with chronic left ventricular myocardial infarction: implications to atrial fibrillation. Circulation 2003;108:360-366.

Moise et al., "An Animal Model of Spontaneous Arrhythmic Death," Journal of Cardiovascular Electrophysiology, Jan. 1997, pp. 98-103, vol. 8.

Moniotte et al., "Upregulation of $\beta_3$-Adrenoceptors and Altered Contractile Respose to Inotropic Amines in Human Failing Myocardium." Circulation, 2001, pp. 1649-1655, vol. 103, American Heart Association, USA.

Mukherjee, et al.; Beta adrenergic and muscarinic cholinergic receptors in canine myocardium. Effects of ischemia. J.Clin.Invest 1979;64:1423-1428.

Mukherjee, et al.: Relationship between beta-adrenergic receptor numbers and physiological responses during experimental canine myocardial ischemia. Cir.Res. 1982;50:735-741.

Myerburg et al., "Frequency of Sudden Cardiac Death and Profiles of Risk," The American Journal of Cardiology, Sep. 11, 1997, pp. 10F-19F, vol. 80 (5B), Excerpta Medica, Inc., USA.

Oh et al., "Relationship between nerve sprouting and neurotrophic gene expression in a mouse model of myocardial infarction," Heart Rhythm, May Supp. 2004, p. S191, Abstract No. 608, vol. 1, No. I.

Oh, et al.: Scar formation after ischemic myocardial injury in MRL. mice. Cardiovasc Pathol 2004;13:203-6.

Ohara, et al.: Downregulation of Immunodetectable Atrial Connexin40 in a Canine Model of Chronic Left Ventricular Myocardial Infarction: Implications to Atrial Fibrillation. J Cardiovasc Pharmacol Ther 2002;7:89-94.

Ohara, et al.; Increased vulnerability to inducible atrial fibrillation caused by partial cellular uncoupling with heptanol. Am J Physiol 2002;283:H1116-1122.

Okin, et al: Assessment of QT Interval and QT Dispersion for Prediction of All-Cause and Cardiovascular Nortality in American Indians: The Strong Heart Study. Circulation 2000;101:61-66.

(56) References Cited

OTHER PUBLICATIONS

Okuyama, et al.: High resolution mapping of the pulmonary vein and the vein of marshall during induced atrial fibrillation and atrial tachycardia in a canine model of pacing-induced congestive heart failur. J Am Coll Cardiol 2003;42:348-60.

Okuyama, et al.: Nerve sprouting induced by radiofrequency catheter ablation in dogs. Heart Rhythm 2004;1:712-7.

Omichi et al., "Transmembrane $Ca^{2+}$ Transients and Action Potential Duration Restitution are Two Independent but Coupled Phenomena in Ventricular Fibrillation," Supplement to Circulation, Abstracts from Scientific Sessions 2000, Oct. 31, 2000, p. 1672, vol. 102, No. 18, American Heart Association, USA.

Omichi, et al.: Comparing cardiac action potentials recorded with metal and glass microelectrodes. Am J Physiol 2000 279:H3113-3117.

Omichi, et al.: Demonstration of electrical and anatomical connections between Marshall bundles and left atrium in dogs: implications on the generation of P waves on surface electrocardiogram. J Cardiovasc Electrophysiol 2002; 13:1283-1291.

Omichi, et al.: Effects of amiodarone on wave front dynamics during ventricular fibrillation in isolated swine right ventricle. Am J Physiol 2002:282:H1063-1070.

Oichi, et al.: Intracellular Ca dynamics in ventricular fibrillation. Am J Physiol 2004;286:H1836-H1844.

Packer et al., "The Effect of Carvediol on Morbidity and Mortality in Patients with Chronic Heart Failure," The New England Journal of Medicine, May 23, 1996, pp. 1349-1355, vol. 334, No. 21, Massachusetts Medical Society, Boston, MA, USA.

Pak, et al.: Catheter ablation of ventricular fibrillation in rabbit ventricles treated with beta-blockers. Circulation 2003:108:3149-56.

Pak, et al.: Improvement of ventricular defibrillation efficacy with pre-shock synchronized pacing. J Cardiovasc Electrophysiol 2004: 2004;15:581-587.

Pak, et al.: Mesenchymal stem cell injection induces-cardiac nerve sprouting and increased tenascin expression in a swine model of myocardial infarction. J Cardiovasc Electrophysiol. 2003;14:841-48.

Paki, et al.: Synchronization of ventricular fibrillation with real-time feedback pacing: Implication to low-energy defibrillation. Am J Physiol 2003;285:H2704-2711.

Park, et al.: Thoracic vein ablation terminants chronic atrial fibrillation in dogs. Am J Physiol Heart Circ Physiol. 2004:286(6):H2072-7.

Parry, et al.: Incidence and functional significance of sympathetic reinnervation after cardiac transplantation. Transplant Proc 1997:29:569-570.

Peckova, et al.: Weekly and seasonal variation in the incidence of cardiac arrest. Am.Heart J. 1999;137:512-515.

Pedersen, et al.: The occurrence and prognostic significance of atrial fibrillation/-lutter following acute myocardial infarction. TRACE Study group. TRAndolapril Cardiac Evaluation. Eur Heart J 1999;20:748-754.

Perry, et al.: Late ventricular arrhythmia and sudden death following direct-current catheter ablation of the atrioventricular junction. Am.J. Cardiol. 1992;70:765-768.

Peters RW: Propranolol and the morning increase in sudden cardiac death; (the beta-blocker heart attack trial experience). Am.J.Cardiol. 1990;66:57G-59G.

Podio et al.: Regional sympathetic denervation after myocardial infarction: a follow-up study using [1231]MIBG. Q J Nucl Med 1995;39;40-43.

Priori et al., "Clinical and Molecular Characterization of Patients with Catecholaminergic Polymorphic Ventricular Tachycardia," Circulation, Jul. 2, 2002, pp. 69-74, vol. 106, American Heart Association, USA.

Reitter, "β-Adrenergic Blocking Drugs as Antifibrillatory Agents," Current Cardiology Report, 2002, pp. 426-433, vol. 4, Current Science, Inc.

Rosenbaum, et al.: Predicting sudden cardiac death from T wave alternans of the surface electrocardiogram: promise and pitfalls. J.Cardiovasc.Electrophysiol. 1996;74:1095-1111.

Rush RA: Immunohistochemical localization of endogenous nerve gowth factor. Nature 1984;312:364-367.

Sanguinetti, et al.: Coassembly K(V)LQT1 and minK )IsK) protens to form cardiac I(Ks) potassium channel. Nature 1996;384:80-83.

Schwartz, et al.: Autonomic nervous system and sudden cardiac death: Experimental basis and clinic observations for post-myocardial infarction risk stratification. Circulation 1992;85:I-77-I-91.

Schwartz, et al.: Left cardiac sympathetic denervation in the management of high-risk patients affected by the long-QT syndrome. Circulation 2004;109:1826-1833.

Schwartz, et al: Left cardiac sympathetic denervation in the therapy of congenital long QT syndrome. A worldwide report. Circulation 1991;84:503-511.

Schwartz, et al.: Prevention of sudden cardiac death after a first myocardial infarction by pharmacologic or surgical antiadrenergic interventions. J Cardiovasc Electrophysiol 1992:3:2-16.

Schwartz, et al.: Sympathetic nervous system and cardiac arrhythmias, in Zipes, DP, Jalife J (eds): Cardiac Electrophysiology: From Cell to Bedside. Philadelphia, PA, W. B. Saunders Company, 1990, pp. 330-343.

Schwartz, et al.: The long QT syndrome, in Zipes DP, Jalife J (eds): Cardiac Electrophysiology: From Cell to Bedside. Philadelphia, W. B. Saunders Company, 1994, pp. 788-811.

Shen et al., "Differences in $β_3$-Adrenergic Receptor Cardiovascular Regulation in Conscious Primates, Rates and Dogs," The Journal of Pharmacology and Experimental Therapeutics, 1996, pp. 1435-1443, vol. 278, No. 3, The American Society for Pharmacology and Experimental Therapeutics, USA.

Shimizu, et al.: Cellular basis for the ECG features of the LQT1 form of the long-QT syndrome: efforst of beta-adrenergic agonists and antagonists and sodium channel blockers on transmural dispersion of repolarization and torsade de pointes. Circulation 1998;98:2314-2322.

Shimzu, et al.: Differential effects of beta-adreneregic agonists and antagonists in LQT1, LQT2 and LQT3 models of the long QT syndrome. J Am Coll Cardiol 2000;35:778-786.

Shimizu, et al.: Sympathetic modulation of the long QT syndrome. Eur.HeartJ. 2002;23:1246-1252.

Shivkumar, et al.: Sudden death after heart transplantation: the major mode of death. J Heart Lung Transplant 2001:20:180(abstract).

Sjoberg, et al.: The initial period of peripheral nerve regeneration and the importance of the local environment for the conditioning lesion effect. Brain Res 1990;529:79-84.

Stanton, et al.: Regional sympathetic denervation after myocardial infarction in humans detected noninvasively using I-123-metaiodobenzylguanidine. J Am Coll Cardiol 198:14:1519-1526.

Strohmer, et al.; Radiofrequency ablation of focal atrial tachycardia and atrioatrial conduction from recipient to donor after orthotopic heart tansplantation, J Cardiovasc Eiectrophysiol 2000;11:1165-9.

Sutula, et al.: Mossy fiber synaptic reorganization in the epileptic human temporal lobe, Ann Neural 1989;26:321-330.

Sutula, et al.: Synaptic reorganization in the hippocampus induced by abnormal functional activity. Science 1988;239:1147-1150.

Swan, et al.: Sinus node function and ventricular repolarization during exercise stress test in long QT syndrome patients with KvLQT1 and HERG potassium channel defects, J Am Coll Cardiol 1999;34:823-829.

Swissa et al., "Long-Term Subthreshold Electrical Stimulation of the Left Stellate Ganglion and a Canine Model of Sudden Cardiac Death," Journal of the American College of Cardiology, Mar. 3, 2004, pp. 858-864, vol. 43, No. 5, Elsevier Inc., USA.

Swissa, et al.: Action potential duration restitution and ventricular fibrillation due to rapid focal excitation. Am J Physioi 2002;282:H1915-1923.

Takei, et al: The autonomic controlof the transmittal dispersion of ventricular repolarization in anesthetized dogs. J Cardiovasc Electrophysiol 1999;10:981-989.

Tavernier et al., "The Positive Chronotropic Effect Induced by BRL 37344 and CGP 12177, Two *Beta*-3, Adrenergic Agonists, Does Not Involve Cardiac *Beta* Adrenoceptors but Baroreflex Mechanisms," The Journal of Pharmacology and Experimental Therapeutics, Dec.

(56) References Cited

OTHER PUBLICATIONS 1992, pp. 1083-1090, vol. 263, No. 3, The American Society for Pharmacology and Experimental Therapeutics, William & Wilkins, USA.
Thandroyen, et al.: Alterations in beta-adrenergic receptors, adenylate cyclase, and cyclic AMP concentrations during acute myocardial ischemia and reperfusion, Circulation 1990;82:1130-1137.
Tsai, et al.: T-wave alternans as predictor of spontaneous ventricular tachycardia in a canine model of sudden cardiac death. J Cardiovasc Electrophsiol 2002;13:51-55.
Ursell, et al., "Anatomic Distribution of Autonomic Neural Tissue in the Developing Dog Heart: I Sympathetic Innervation," The Anatomical Record, Jan. 1990, pp. 71-80, vol. 226, No. 1, American Association of Anatomists, Wiley-Liss, USA.
Valderrábano, et al.: Obstacle-Induced transition from ventricular fibrillation to tachycardia in Isolated swine right Ventricles: Insights into the transition dynamics and implications for the critical mass. J Am Coll Cardiol 2000;36:2000-8.
Valderrábano, et al: Frequency analysis of ventricular fibrillation in swine ventricles. Circ Res 2002;90: 213-222.
Varghese et al., "$\beta_3$- adrenoceptor deficiency blocks nitric oxide-dependent inhibition of myocardial contractility," The Journal of Clinical Investigation, Sep. 2000, pp. 697-703, vol. 106, No. 5, American Society for Clinical Investigation, USA.
Vassalle, et al.: The effect of adrenergic enhancement on overdrive excitation. J.Electrocardiol. 1976;9:353-343.
Verrier, et al.; Ventricular vulnerability during sympathetic stimulation: role of heart rate and blood pressure. Cardiovasc Res 1974;8:602-610.
Viskin, et al.: Circadian variation of symptomatic paroxysmal atrial fibrillation. Data from almost 10 000 episodes. Eur Heart J 1999;20:1429-1434.
Vleeming et al., "Density of $\beta$ adrenoceptors in rat heart and lymphocytes 48 hours and 7 days after acute myocardial infarction." Cardiovascular Research, 1989, pp. 859-866, vol. 23.
Voroshilovsky, et al.: Mechnisms of ventricular fibrillation induction by 60 Hz alternating current in isolated swine right ventricle. Circulation 2000;102:1569-1574.
Vracko, et al.: Fate of nerve fibers in necrotic, healing, and healed rat myocardium. Lab Invest 1990;63:490-501.
Vracko, et al.: Nerve Fibers in human myocardeial scars. Hum Pathol 1991;22:138-146.
Wang, et al.: Optical mapping of ventricular defibrillation in isolated swine right ventricles: demonstration of a postshock isoelectric window after ner-threshold defibrillation shocks. Circulation 2001;104 227-233.
Wisser, et al.: Circadian changes of clinical chemical and endocrinological parameters. J. Clin.Chem.Clin.Biochem. 1981;19:323-337.
Wu TJ, et al.: Mother rotors and the mechanisms of D600-induced type 2 ventricular fibrillation. Circulation, 2004;110;2110-2118.
Wu TJ, et al.: Progressive action potential duration shortening and the conversion from atrial flutter to atrial fibrillation in isolated canine right atrium. J Am Coll Cardiol 2001;38:1754-1765.
Wu TJ, et al.: Simultaneous biatrial computerized mapping during permanent atrial fibrillation patients with organic heart diseases. J Cardiovasc Electrophysiol 2002;13:571-577.
Wu, et al.: Pulmonary veins and ligament of Marshall as sources of rapid activations in a canine model of sustained atrial fibrillation. Circulation 2001;103:1157-1163.
Yambe, et al.: Vagal nerve activity and the high frequency peak of the heart rate varibility. Int.J.Artif.Organs 1999;22:324-328.
Yambe, et al.: Vagal nerve activity recording in the awake condition for the control of an artificial heart system. Artif.Organs 1999;23:529-531.
Yanowitz, et al.: Functional distribution of right and left stellate innervation to the ventricles. Production of neurogenic electrocardiographic changes by unilateral alteration of sympathetic tone. Circ Res 1966;18:416-428.
Yashima, et al.: Nicotine increases ventricular vulnerability to fibrillation in hearts with healed myocardial infarction. Am J Physiol (Heart and Circulatory Physiology) 2000;278:H2124-33.
Yashima, et al.: On the Mechanismm of the Probabilistic Nature of Ventricular Defibrillation Threshold. Am J Physiol 2003;284:H249-255.
Zhou, et al.: Modulation of QT interval by cardiac sympathetic nerve sprouting and the mechanisms of ventricular arrhythmia in a canine model of sudden cardiac death. J Cardiovasc Electrophysiol 2001;12:1068-73.
Zhou, et al.: Satellite-cell-derived nerve growth factor and neurotrophin-3 are involved in the noradenergic sprouting in the dorsal root ganglia following peripheral nerve injury in the rat. Eur.J Neurosci. 1999;11:1711-1722.
PCT/US2005/23142 International Search Report dated Aug. 17, 2006.
PCT/US2005/23142 Written Opinion dated Aug. 17, 2006.
PCT/US2005/23142 International Preliminary Report on Patentability dated Jan. 9, 2007.
PCT/US2006/07197 International Search Report dated Sep. 18, 2006.
PCT/US2006/07197 Written Opinion dated Sep. 18, 2006.
PCT/US2006/07197 International Preliminary Report on Patentability dated Sep. 11, 2007.
Sutherland Stephani P. et al., "Acid-sensing ion channel 3 matches the acid-gated current in cardiac ischemia-sensing neurons," The Vollum Institute, Oregon Health Sciences University, Portland, OR 97201-3098, pp. 1-10. http://www.pnas.org/content/98/2/711.full.
Swissa et al., Long-Term Subthreshold Electrical Stimulation of the Left Stellate Ganglion and a Canine Model of Sudden Cardiac Death. J. Am. Coll. Cardiol, 2004: 43:858-64.
Akingba A G, Wang D. Chen P-S, Neves H, Montemagno C: Application of nanoelectrodes in recording biopotentials. Nanotechnology, 2003. IEEE-NANO 2003; 2:870-874.
Akingba A G, Wang D. Chen P-S, Neves H, Montemagno C: Application of nanoelectrodes recording biopotentials. Nanotechnology, IEEE-NANO 2003; 2:870-874.

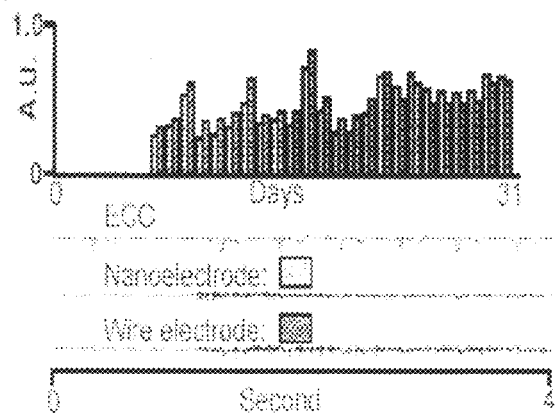
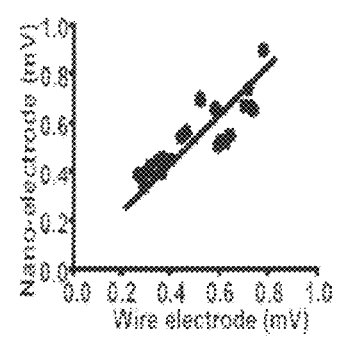
Fig. 8A
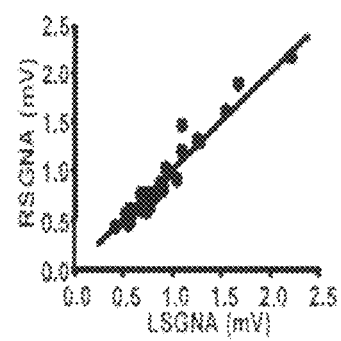
Fig. 8B
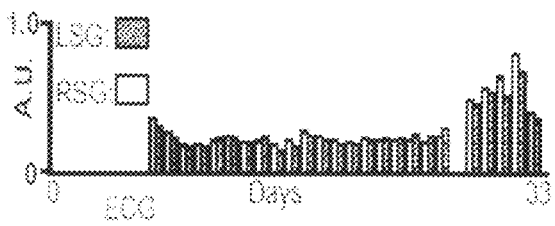
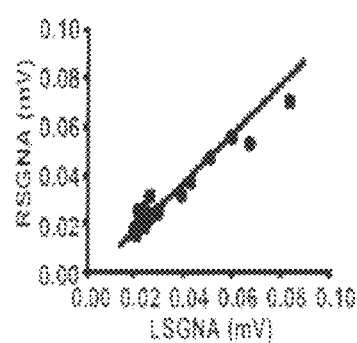
Fig. 8C

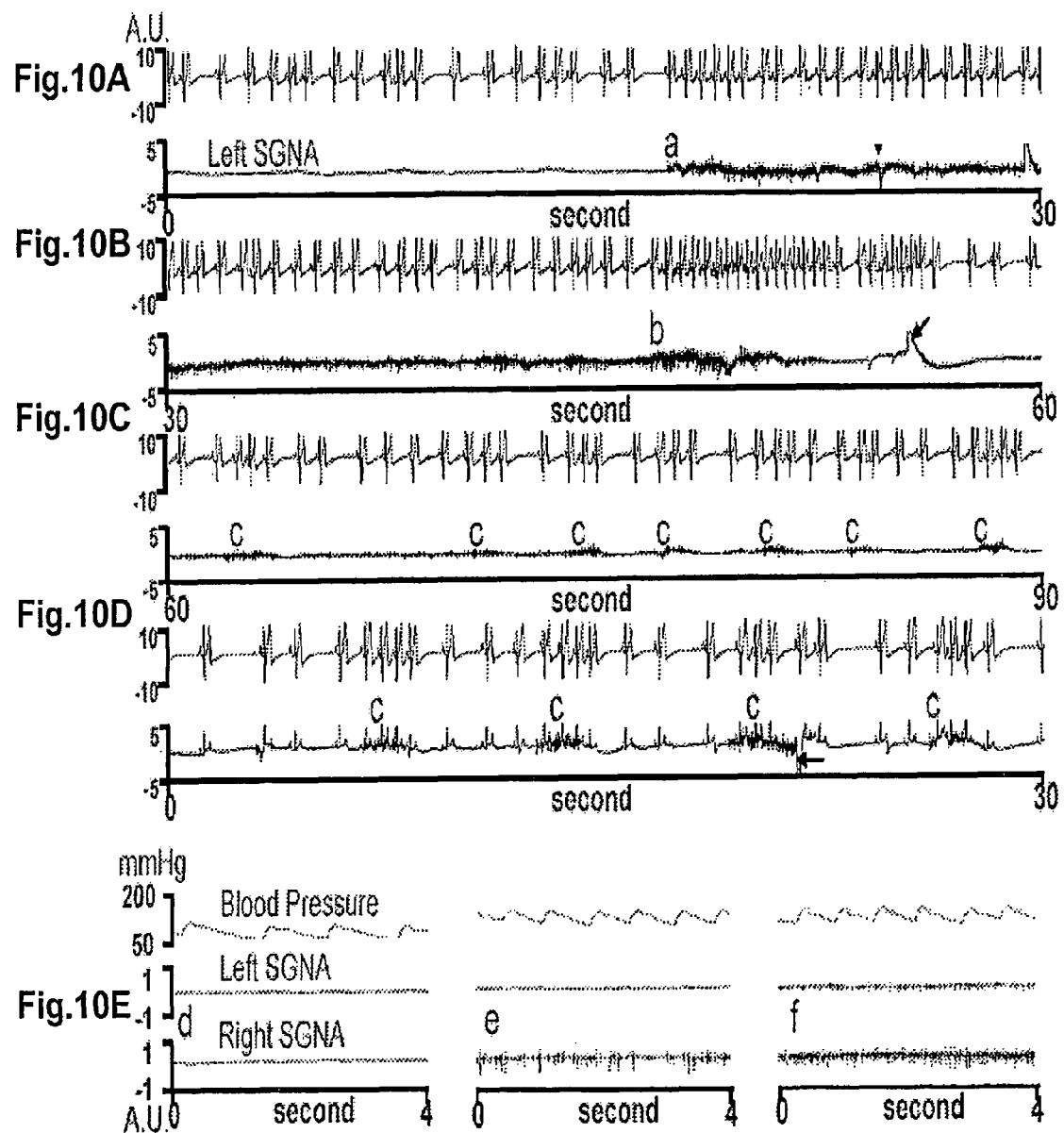

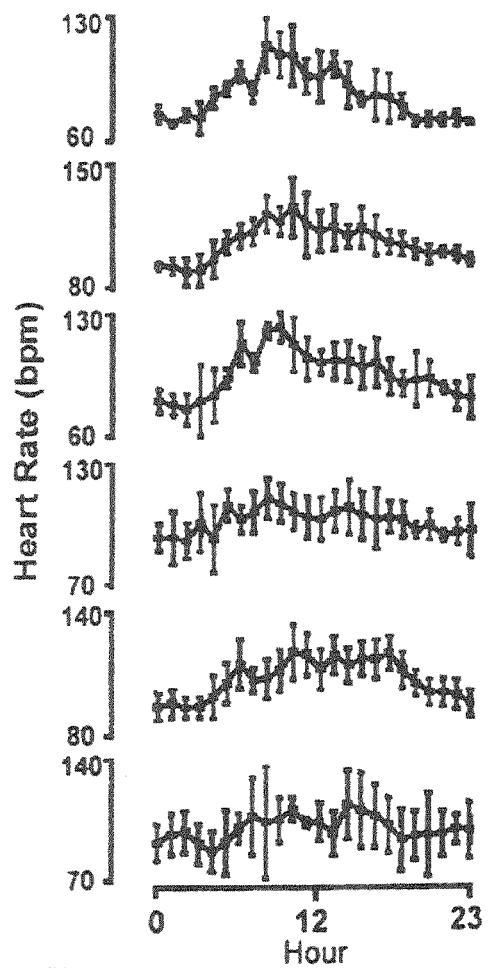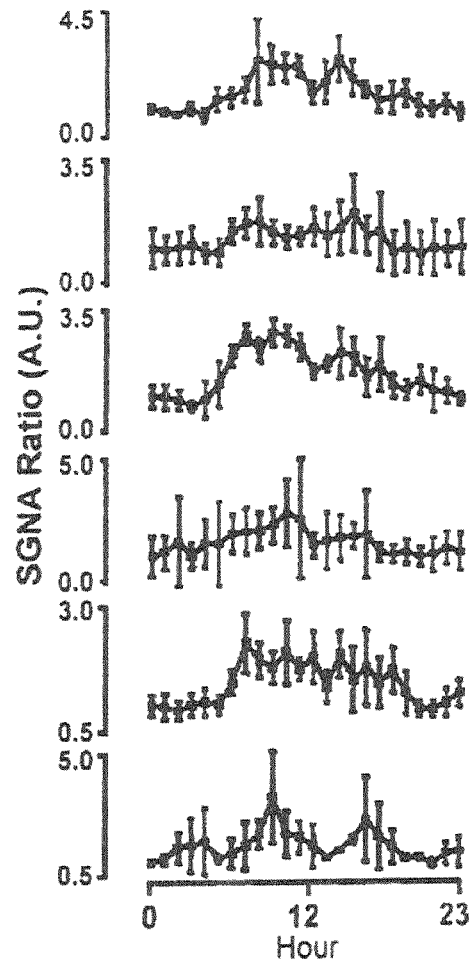
FIG. 11A
FIG. 11B
FIGURE 11

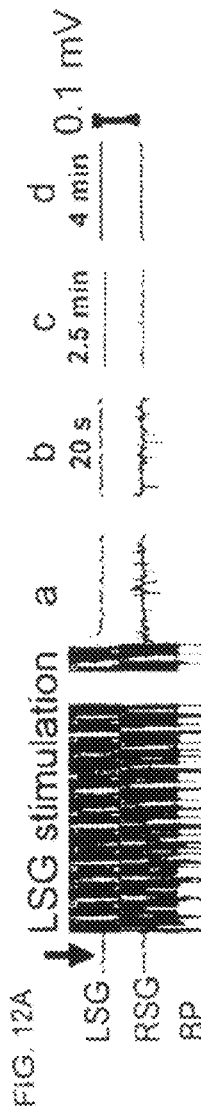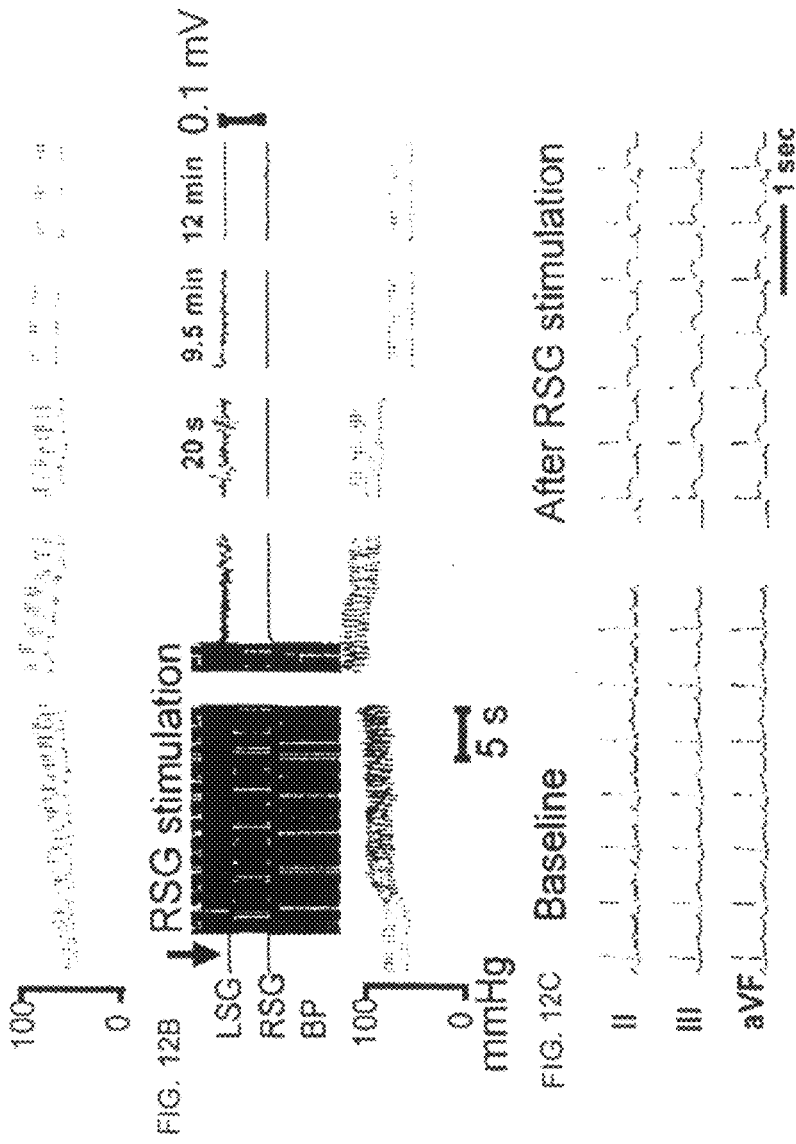

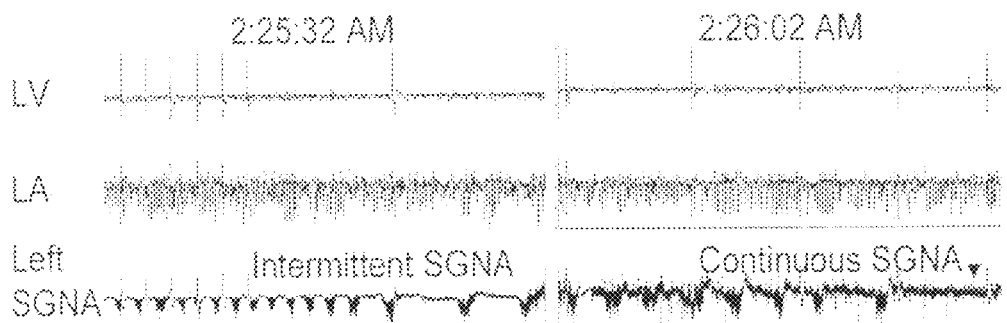
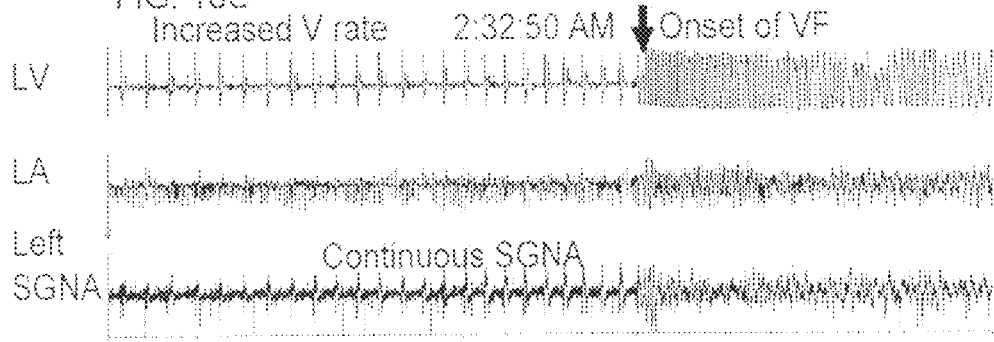
Fig. 16

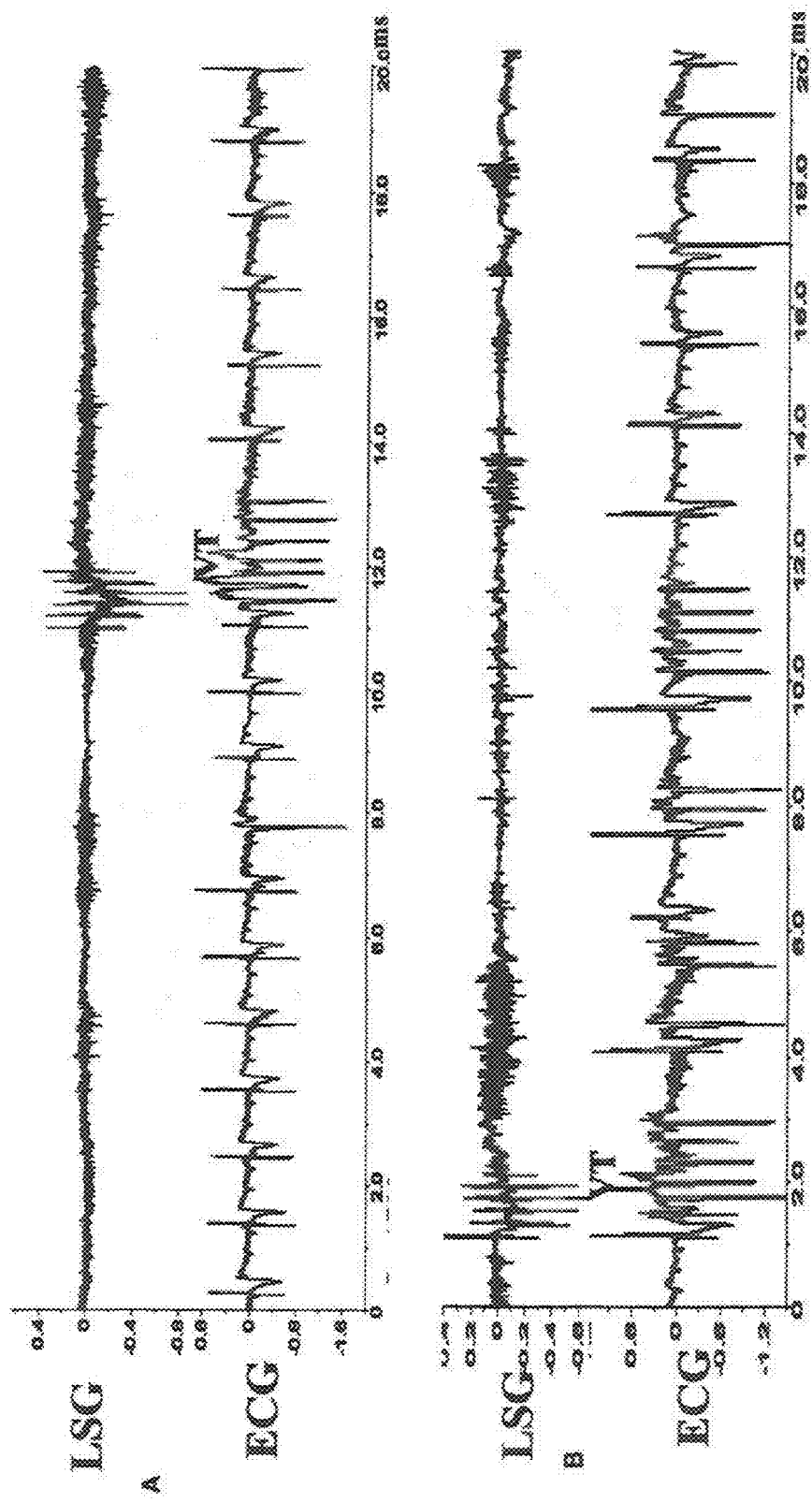
FIGURE 20 A-B

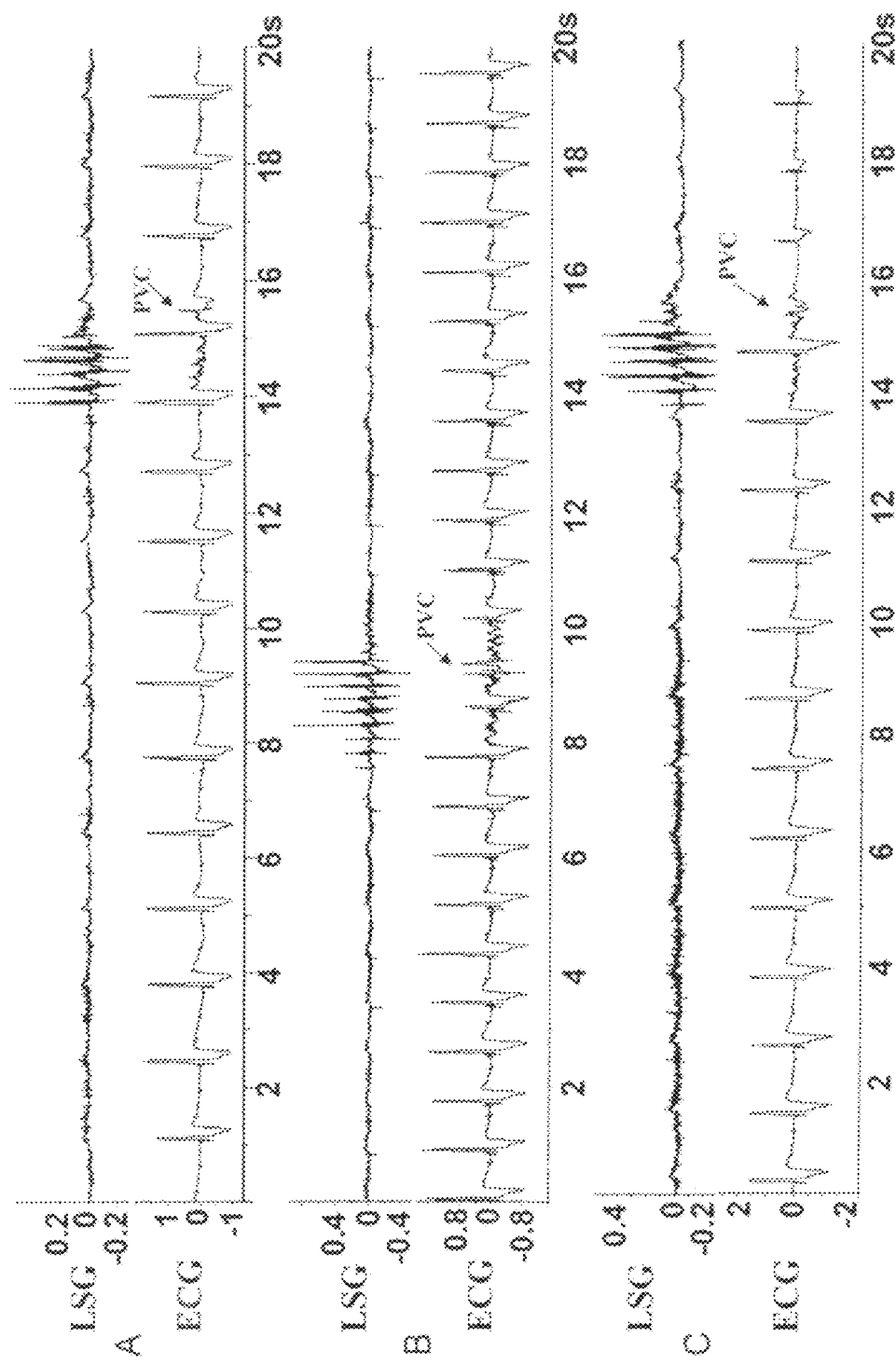
Fig. 21A-C

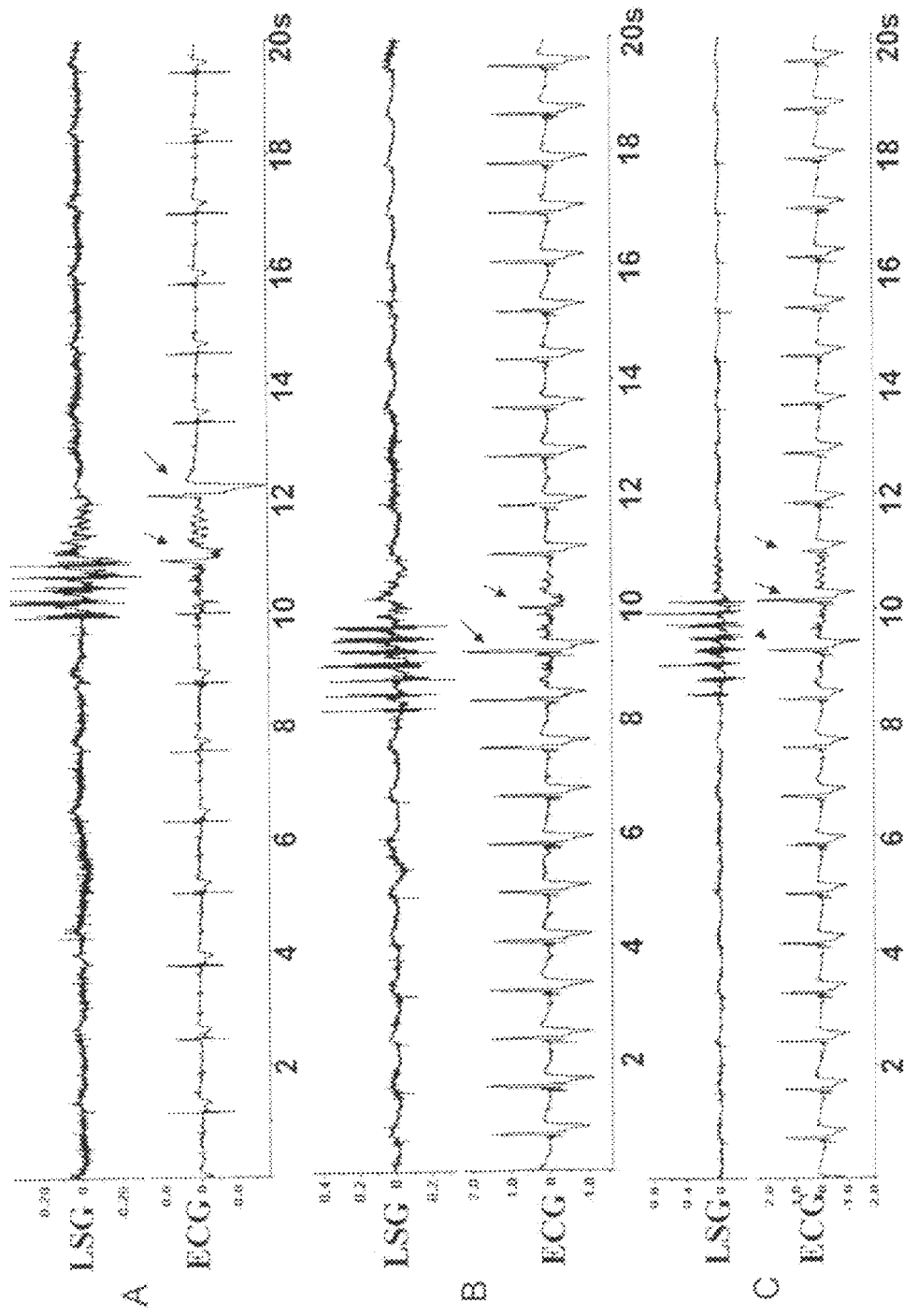
Fig. 22A-C

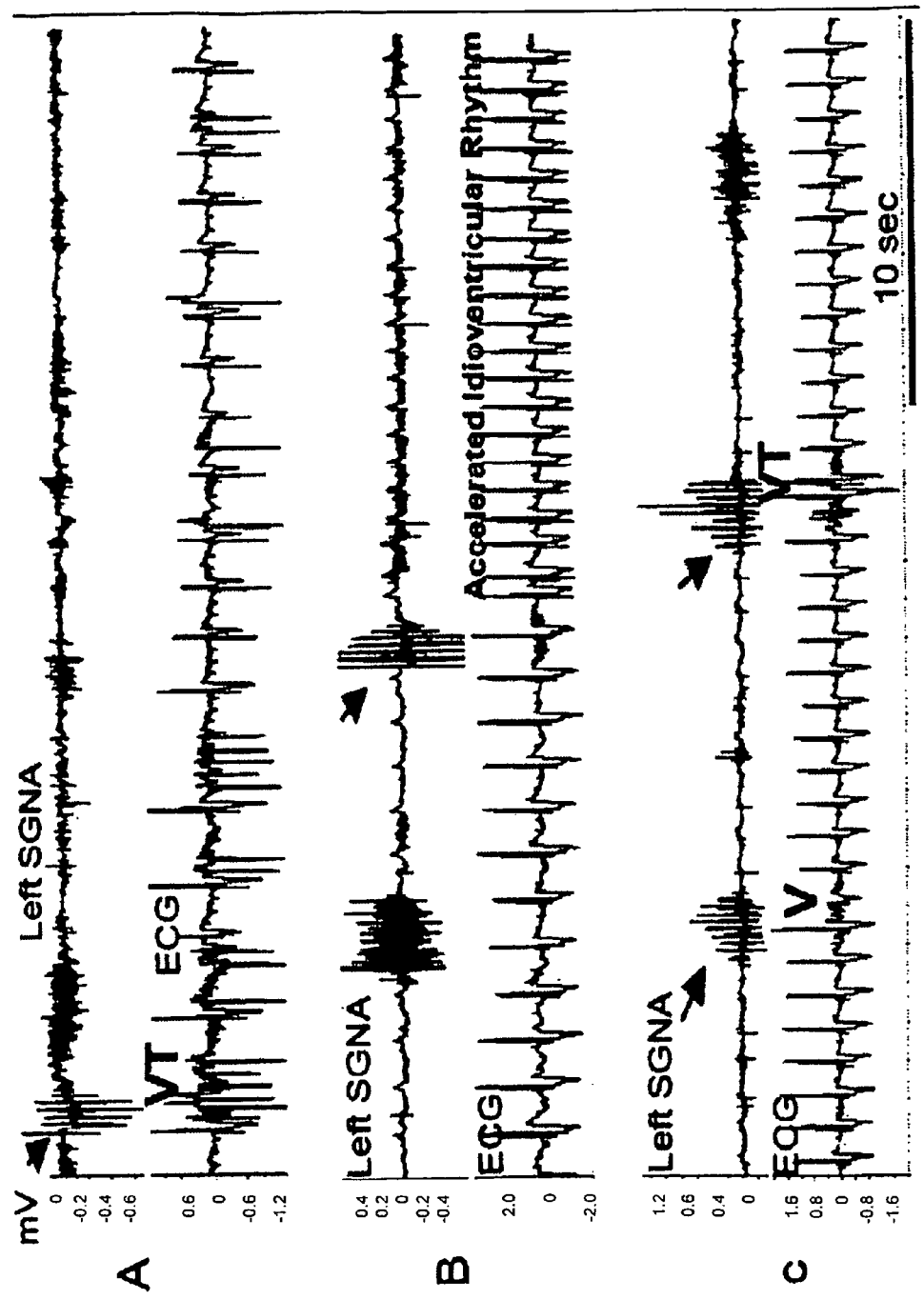
Fig. 23A-C

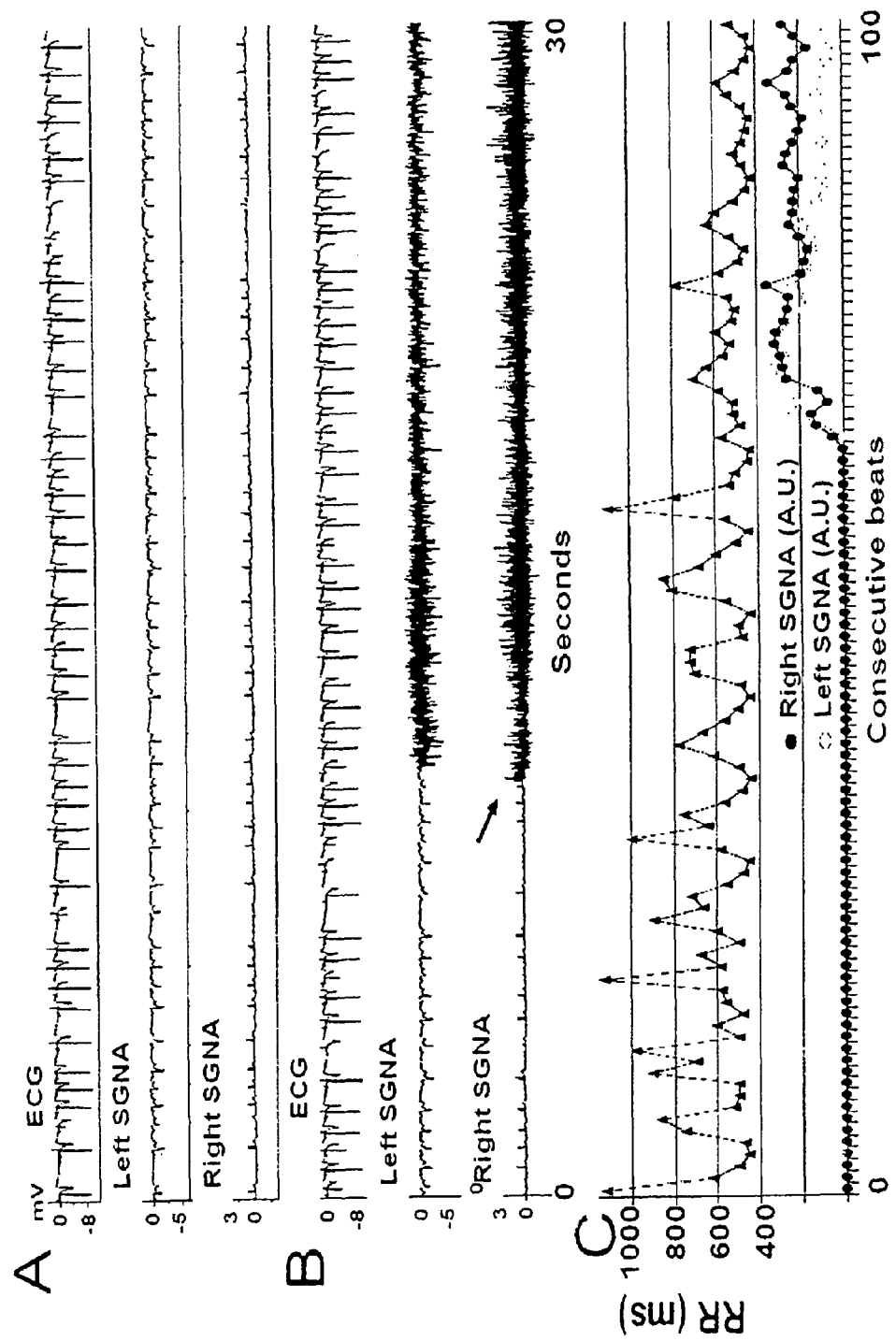
Fig. 24A-C

METHOD AND SYSTEM FOR THE PREDICTION OF CARDIAC ARRHYTHMIAS, MYOCARDIAL ISCHEMIA, AND OTHER DISEASED CONDITION OF THE HEART ASSOCIATED WITH ELEVATED SYMPATHETIC NEURAL DISCHARGES

CROSS-REFERENCE TO RELATED APPLICATIONS

This is a continuation of application Ser. No. 11/205,923, filed Aug. 16, 2005, now U.S. Pat. No. 7,725,178, which is a continuation-in-part application of application Ser. No. 11/069,753, filed Feb. 28, 2005, now U.S. Pat. No. 7,266,410, which is a continuation-in-part of application Ser. No. 10/882,645, filed Jun. 30, 2004, now abandoned, all of which are incorporated by reference herein in their entirety.

GOVERNMENT INTEREST

This invention was made in part with government support under Grant R01 HL66389, awarded by the National Institutes of Health. The government has certain rights to this invention.

FIELD OF THE INVENTION

The invention generally relates to a methods and systems for the prediction of cardiac arrhythmias of the type that can result in sudden cardiac death.

BACKGROUND OF THE INVENTION

Sudden cardiac death (SCD) is a major public health problem that accounts for more than half of all cardiovascular deaths. SCD takes the lives of approximately 450,000 people in the United States each year, more than lung cancer, breast cancer, stroke, and AIDS combined. Most cases of SCD are due to ventricular arrhythmias and there is often an element of underlying ischemic heart disease. Ventricular tachycardia (VT) and ventricular fibrillation (VF) are different types of ventricular arrhythmias. VT is an abnormally fast ventricular heart rhythm which is, by itself, typically not fatal. VF is a chaotic ventricular heart rhythm which produces little or no net blood flow from the heart, such that there is little or not net blood flow to the brain and other organs. VF, if not terminated, results in death. Patient groups most at risk of ventricular arrhythmias leading to SCD include those with an acute or chronic myocardial infarction. Accordingly, deaths from SCDs may be lowered by preventing the specific heart rhythm disturbances (ventricular arrhythmias) associated with it.

Different treatment options exist for SCD. The most common treatment includes implantable cardiac defibrillators (ICD) and drug therapy. ICDs have been available in the United States since the mid-1980s and have a well-documented success rate in decreasing the rate of death of patients at high risk for SCD. A major trial conducted by the U.S. National Institutes of Health (the Anti-arrhythmics Versus Implantable Defibrillator or AVID trial) compared therapy with the best available anti-arrhythmic drugs with ICD therapy for patients with spontaneous ventricular tachycardia or ventricular fibrillation. The overall death rate in the ICD patient group was found to be 39% lower than the death rate of patients treated with anti-arrhythmic drugs after only 18 months mean follow-up.

An ICD has two basic components: the ICD generator and the lead system for pacing and shock delivery to which it is connected. An ICD generator contains sensing circuits, memory storage, capacitors, voltage enhancers, a telemetry module, and a control microprocessor. Advances in miniaturization and complexity in all of these components have permitted a tremendous reduction in size of the generator itself despite increased functionality, such as added programming options, anti-tachycardia pacing, single- and dual-chamber rate-responsive pacing for bradycardia, biphasic defibrillation waveforms, enhanced arrhythmia detection features, and innovations in lead systems.

Current ICD technology, however, provides for the detection and recognition of an arrhythmia based on the sensed heart rate once it has already started. This leaves very little time to protect the individual from death resulting from SCD. Although there have been several attempts at developing new technology for predicting the onset of a cardiac arrhythmia, many of these methods and systems appear to rely primarily on events occurring within the heart, such as sensed heart rate and electrocardiography (ECG). For example, U.S. Pat. No. 6,308,094 discloses a method and device for predicting cardiac arrhythmias by gathering and processing electrocardiographic data, such as intervals between heart beats (RR-series) or other heart signals, to predict the occurrence of a cardiac arrhythmia. U.S. Pat. No. 6,516,219 discloses a method and apparatus for forecasting arrhythmia based on real-time intact intracardiac electrograms.

SUMMARY OF INVENTION

Methods and systems are provided for determining an increased likelihood of the occurrence of a cardiac arrhythmia, myocardial ischemia, and/or other diseased condition of the heart associated with elevated sympathetic nerve discharges in a patient. The methods and systems disclosed herein generally comprise monitoring the sympathetic neural discharges of a patient from the stellate ganglia, the thoracic ganglia, and/or any other sympathetic nerve identified as having an influence over the heart rate of a patient. Other sympathetic nerves suitable for use in connection with the prediction of cardiac arrhythmias may be generally determined by obtaining simultaneous recordings of neural discharges and heart rate in a test subject and determining whether there exists a correlation between an observed increase in the amplitude and/or frequency of the neural discharges and an increase in heart rate.

Elevated stellate ganglia nerve activity (SGNA) has been demonstrated to precede the onset of cardiac arrhythmias of the type leading to SCD and, additionally, myocardial ischemia. Myocardial ischemia may or may not cause chest pain (angina). When myocardial ischemia does not cause chest pain, it is known as "silent ischemia." It has been shown that stellate ganglion stimulation can cause ischemia, as shown by the ST segment elevation in FIG. 12C. The ST elevation suggest that significant myocardial ischemia, probably due to the combined effects of alpha-receptor induced coronary constriction and beta-receptor increase in oxygen consumption. The ability to continuously monitor SGNA will provide a method to predict the onset of silent ischemia.

In one embodiment, the sympathetic neural discharges may be monitored by a sensor or electrode that is implanted in the stellate ganglia to measure the stellate ganglia nerve activity (SGNA) of the patient from the left stellate ganglion (LSG), the right stellate ganglion (RSG), or both. For example, the electrode may directly sense electrical activity of the stellate ganglia and transmit this data to a processor. The processor may then analyze the data acquired from the electrode and, upon the determination that the SGNA has increased beyond a defined normal value, produce an output signal indicating the likely onset of an arrhythmia, myocardial ischemia, and/or other diseased condition of the heart associated with elevated sympathetic nerve discharges.

In another embodiment, an increase in the sympathetic neural discharge in the patient may be determined by comparing the parameters for the sensed and normal sympathetic neural discharges in the patient. In yet another embodiment, an increase in the sympathetic neural discharge may be determined by detecting increases in the amplitude and frequency of the sensed sympathetic neural discharge beyond defined normal values, such as the sensed electrical activity of the stellate ganglia and/or the thoracic ganglia. In yet another embodiment, the sensed electrical activity of the left stellate ganglion may be monitored for epileptiform-like discharges.

The defined normal value represents a value above or beyond which is indicative of an impending arrhythmic, ischemic or other diseased condition of the heart associated with elevated sympathetic nerve discharges and may be determined with reference to the normal baseline sympathetic neural discharge. For example, a two-fold or greater increase in the amplitude of the sensed sympathetic neural discharge from the normal baseline amplitude of sympathetic neural discharge may be used as a suitable defined normal value. A second defined normal value reflecting the frequency of the sympathetic neural discharge above or beyond which is indicative of an impeding arrhythmic condition of the heart may similarly be provided. The defined normal values may be preset or user-defined programmable values.

An output signal may be generated in response to a determined increase in the sympathetic neural discharge. In one embodiment, the output signal may be an audible sound, a radio-transmitted or radiofrequency signal, an electrical signal, or any other type of signal that would alert the patient or physician to the possibility of an impending arrhythmia. In another embodiment, the output signal may be an analog or digital command signal directing the delivery of therapy to the patient.

Suitable therapy for use in connection with the methods and systems are known in the art and may include any one or a combination of the following: delivering one or more pharmacological agents; stimulating myocardial hyperinnervation in the sinus node and right ventricle of the heart of the patient; and applying cardiac pacing, cardioversion or defibrillation shocks, to name a few.

Any one or more pharmacologic agent(s) may be used in connection with the delivery of therapy. Such pharmacologic agents may include those which are effective in treating cardiac arrhythmias, myocardial ischemia, congestive heart failure, and any other diseased condition of the heart that is associated with elevated sympathetic neural discharges. Pharmacologic agents which may be used in connection with the delivery of anti-arrhythmic therapy may include, but are not limited to, those which are known to exert anti-arrhythmic effect, such as sodium channel blockers, β-blockers, potassium channel blockers, such as amiodarone and solatol, and calcium channel blockers, such as verapamil and diltiazem. Pharmacologic agents suitable for the treatment of myocardial ischemia may include, but are not limited to, statins, angiotensin-converting enzyme (ACE) inhibitors, aspirin, beta blockers, calcium channel blockers, and nitrates. Other suitable pharmacologic agents may include anti-convulsant agents, including but not limited to phenytoin, carbamazepine, valproate, and phenobarbitone, to name a few, which are believed to have anti-arrhythmic effect.

The methods and systems described herein may be incorporated into any number of implantable medical devices including, but not limited to, implantable cardiac rhythm management systems such as pacemakers, cardioverters, defibrillators, and the like. The present methods and systems may also be incorporated in external unimplanted devices of the same sort, as well as in external monitors, programmers and recorders.

The above and other objects, features and advantages will become apparent to those skilled in the art from the following description of the preferred embodiments.

BRIEF DESCRIPTION OF THE DRAWINGS

FIG. 3A shows the bursts of renal sympathetic neural discharges and FIG. 3B shows suppression of renal sympathetic neural discharges by intravenous bolus dose of xylazine and ketamine.

FIG. 5A shows the onset of increased SGNA at time (a) which was followed by an increase in heart rate. FIG. 5B shows the increase in amplitude of the SGNA signals at (b) which is followed but further increases in heart rate. FIG. 5C shows burst increases in the amplitude of SGNA signals at (c), (d), (e), (f), (g), and (h), all of which were followed by short runs of increased atrial rate.

FIGS. 8A-C show the SGNA obtained from stainless steel wire electrodes implanted in the LSG and RSG of an ambulatory normal canine subject. FIG. 8A shows significant correlation between SGNA recorded from the nanoelectrode and from the stainless steel wire electrode from the LSG of an ambulatory normal canine subject. An example of the actual SGNA recordings from the nanoelectrode and wire electrode is shown at the bottom of the bar graph. FIGS. 8B and 8C show significant correlation between the SGNA obtained from a stainless steel wire electrode implanted in the LSG and the RSG in two ambulatory normal canine subjects. Each column in the bar graph and each dot in the corresponding X-Y graph show the average SGNA over a one-day period. The SGNA amplitude remained stable or slightly increased with time. These figures demonstrate that SGNA may be adequately recorded using either the nanoelectrode array or the stainless steel wire electrode.

FIG. 9A is the baseline recording showing no SGNA (from either LSG or RSG) and an ECG showing slow heart rate with significant sinus arrhythmia. FIG. 9B shows increased SGNA from the LSG and sporadic SGNA from the RSG during increased heart rate. FIG. 9C shows sporadic SGNA from the LSG and increased SGNA from the RSG during increased heart rate. FIG. 9D shows increased bilateral SGNA (from the LSG and RSG) associated with rapid heart rate. FIG. 9E shows the onset of bilateral SGNA (as indicated by the arrows) during rapid heart rate. A gradual heart rate deceleration is indicated by the asterisk. A stainless steel wire electrode was used to obtain the SGNA recordings.

FIGS. 10A-E show the relationship between the SGNA from the LSG and heart rate and blood pressure. FIGS. 10A-C are continuous recordings obtained from an ambulatory normal canine subject fifteen (15) days after implantation of the stainless steel wire electrode. In FIG. 10A, the increase in SGNA at (a) was followed by an increase in heart rate. In FIG. 10B, further increases in SGNA at (b) resulted in further increases in heart rate. In FIGS. 10C-D, brief bursts of SGNA at (c) were followed by immediate acceleration in heart rate. The arrows point to possible motion artifacts. FIG. 10E show the relationship between SGNA and blood pressure at baseline (d), unilateral increase in SGNA from the RSG at (e) and bilateral increase in SGNA from both the LSG and RSG at (f). Again, a stainless steel wire electrode was used to obtain the SGNA recordings.

FIGS. 11A-B show average heart rate and normalized SGNA, respectively, over a 24 hour period. The SNGA was normalized to a midnight value.

FIGS. 12A-C show the effect of electrical stimulation of the LSG and RSG in an ambulatory normal canine subject. FIGS. 12A and B show the effect of electrical stimulation on the LSG and RSG, respectively and FIG. 12C shows baseline ST elevation immediately after electrical stimulation of the RSG.

FIG. 14A shows persistent SGNA (as indicated by the horizontal line over the SGNA) from the LSG followed by the onset of ventricular tachycardia (VT). FIG. 14B shows intermittent increases in SGNA from the LSG (as indicated by the arrows) also followed by VT. The asterisk shows signal drop probably due to movement of the canine subject.

FIGS. 16A-C show bipolar LV and LA electrograms and SGNA obtained by a stainless steel wire electrode implanted in the LSG of a canine SCD model. FIG. 16A shows pacemaker non-capture, resulting in the conversion of intermittent SGNA into continuous SGNA in FIG. 16B. The SGNA continued uninterrupted for 6 minutes, resulting in accelerated ventricular escape rhythm followed by ventricular fibrillation, as shown in FIG. 16C. FIGS. 16A-B are continuous tracings.

FIGS. 20A-B show that the high amplitude, epileptiform-like spikes precede ventricular tachycardia (VT).

FIGS. 21A-C show that the epileptiform-like discharges induce premature ventricular contraction (PVC).

FIGS. 22A-C show that the epileptiform-like discharges induce morphology changes of QRST.

FIGS. 23A-C show the epileptiform-like discharges within the left stellate ganglion (upper panels in A-C) and the simultaneously recorded ECG (lower panels). Spikes (arrows) induced nonsustained polymorphic ventricular tachycardia (panel A), and fast accelerated idioventricular rhythm (panel B). In panel C, the spikes induced premature ventricular contraction (V) and nonsustained ventricular tachycardia.

FIGS. 24A-C shows that SGNA reduces heart rate variability. The onset of SGNA (arrow) was followed by accelerated heart rate and reduced heart rate variability. Arrow in B points to the onset of right SGNA, which slightly preceded the onset of the left SGNA. Panel C shows analyses of beat to beat RR interval (interval between the consecutive R waves) and the beat-to-beat SGNA of the same 60 sec of data, which contains 101 consecutive beats and 100 RR intervals. A.U., arbitrary units.

DESCRIPTION OF THE PREFERRED EMBODIMENTS

Figure 1:
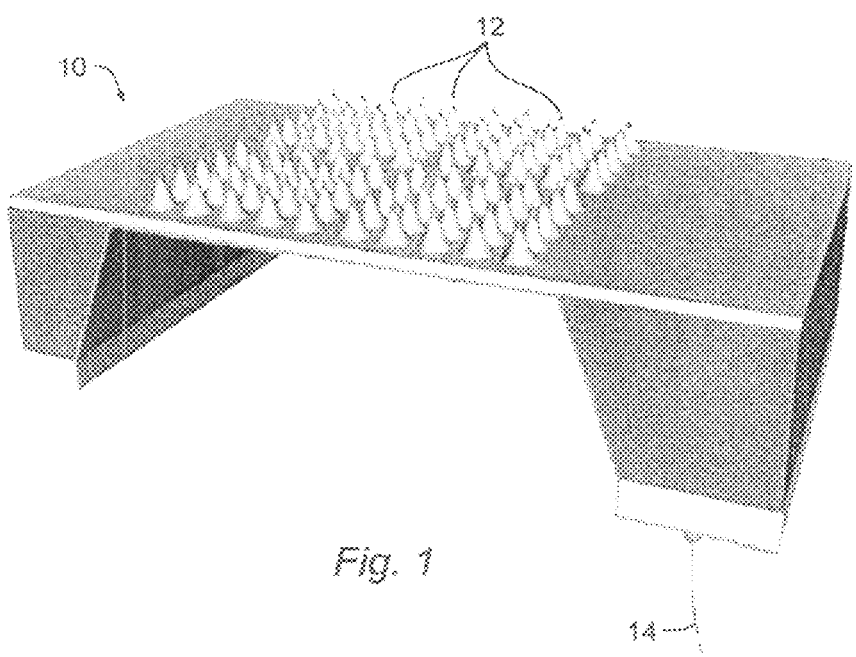
FIG. 1 is a perspective view of a nanoelectrode array.

Methods and systems are disclosed for determining an increased likelihood of the occurrence of a cardiac arrhythmia, myocardial ischemia, congestive heart failure, and any other diseased condition of the heart in a patient that is associated with elevated sympathetic neural discharges. The methods and systems disclosed herein comprise monitoring the sympathetic neural discharges of a patient; determining an increase in the sympathetic neural discharges in the patient beyond defined normal values; and producing an output signal upon a determined increase in the sympathetic neural discharges in the patient. In one embodiment, the output signal may be an audible sound, a radio-transmitted or radiofrequency signal, an electrical signal, or any other type of signal that would alert the patient or physician to the possibility of an impending arrhythmia or other diseased conditions of the heart. In another embodiment, the output signal may be a command signal directing the delivery of suitable therapy.

The sympathetic neural discharges of a patient may be monitored by a sensor or electrode that is implanted in the stellate ganglia, the thoracic ganglia, and/or any other sympathetic nerve for which the rate of neural discharge influences the heart rate in a patient. The sensor or electrode may directly sense electrical activity of the stellate ganglia, the thoracic ganglia or other suitable sympathetic nerve of the patient and transmit this data to a processor for immediate processing or to a memory for storage.

In a preferred embodiment, sympathetic nerve recordings are obtained from the stellate ganglia, the thoracic ganglia, or both. In yet another preferred embodiment, the left stellate ganglia are monitored for epileptiform-like discharges, by which are meant high-amplitude spikes, such as those represented in FIGS. 18-23. It has surprisingly been discovered that such epileptiform-like discharges precede the onset of cardiac arrhythmias, including ventricular fibrillation, and may thus be used as a highly sensitive and specific marker for ventricular arrhythmias and sudden death syndrome.

Increased neural discharges from the stellate ganglia have been observed to precede the onset of cardiac arrhythmias. Consistent with this observation, partial or complete ablation of the LSG, together with the thoracic ganglia T2 to T4, was demonstrated to be effective in reducing the incidence of SCD in patients after a first myocardial infarction. Schwartz P J, et al. Left cardiac sympathetic denervation in the management of high-risk patients affected by the long-QT syndrome. *Circulation*. 2004; 109:1926-1833. These findings suggest that the LSG and the thoracic ganglia are important for ventricular arrhythmogenesis and SCD among high risk patients.

Indeed, it has previously been found that stimulation of the LSG has been found to result in a significant increase in incidence of ventricular arrhythmias and SCD in canine subjects. In contrast, stimulation of the RSG has been shown to be anti-arrhythmic. A method for inducing ventricular arrhythmias in an animal model is disclosed in U.S. Pat. No. 6,351,668, which is incorporated herein in its entirety. Such an animal model is useful in collecting data pertinent to predictors of heart arrhythmias and for testing techniques intended to predict the onset of heart arrhythmias, the disclosures for which are provided in U.S. Pat. Nos. 6,353,757 and 6,398,800, which are incorporated herein in their entirety.

Previous studies have demonstrated heterogeneous sympathetic hyperinnervation in the left ventricle in canine models for sudden cardiac death. Cao J-M, Chen L S, KenKnight B H et al. Nerve sprouting and sudden cardiac death. Circ. Res. 2000; 86:816-21. The electrical heterogeneity does not have significant clinical consequences in normal hearts. However, when the ion channels in the heart are altered by either genetic mutations or electrical remodeling after a myocardial infarction and atrioventricular block, this heterogeneity may be amplified and cause arrhythmia. Accordingly, different sympathetic nerves may exert very different effects on the heart rate.

For example, increased neural discharges from the LSG exert a pro-arrhythmic effect, whereas increased neural discharges from the RSG are believed to be anti-arrhythmic. It has been demonstrated that electrical stimulation of the left stellate ganglia in canine subjects induce high magnitude cardiac nerve sprouting and increased ventricular sympathetic nerve density. If the canine subjects also have complete atrioventricular block and myocardial infarction, sub-threshold electrical stimulation of left stellate ganglia resulted in a high yield canine model of sudden cardiac death. In contrast, sub-threshold electrical stimulation of the right stellate ganglia may induce nerve sprouting from the right stellate ganglia and thereby reduce the risk of SCD in canine subjects with augmented nerve sprouting, myocardial infarction and complete atrioventricular block.

Sub-threshold electrical stimulation to the left stellate ganglia was administered in six (6) normal canine subjects and six (6) canine subjects with myocardial infarction and complete atrioventricular block. The threshold current is the minimum amount of current needed to induce increases in blood pressure and heart rate. All twelve (12) canine subjects were monitored with either an ICD or with a DSI transmitter implanted in a sub-muscular chest pocket for continuous recording with a sampling rate of 1,000 per second. The hearts were harvested a month later. All hearts showed significant hypertrophy, nerve sprouting and sympathetic hyperinnervation. The canine subjects with myocardial infarction and complete atrioventricular block demonstrated frequent ventricular tachycardia and a high incidence of sudden cardiac death. These results show that sub-threshold electrical stimulation to the LSG induces cardiac nerve sprouting and sympathetic hyperinnervation, and facilitates the development of a high-yield canine model of ventricular arrhythmia and sudden cardiac death.

Figure 18:
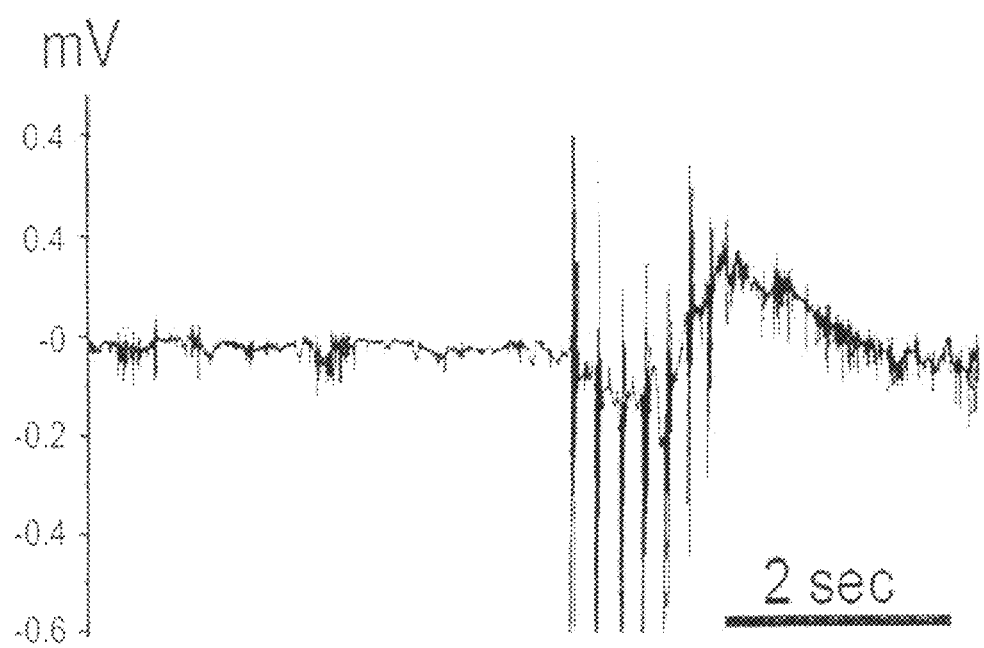
FIG. 18 shows an example of the high amplitude spikes observed to precede the onset of arrhythmia, recorded from the left stellate ganglion in a canine model of sudden cardiac death.

Stellate ganglion nerve activity (SGNA) from dogs with myocardial infarction, complete atrioventricular block and nerve growth factor infusion to the left stellate ganglion (sudden death model) was successfully recorded. Surprisingly, high amplitude (epileptiform-like) spikes in the SGNA recordings were observed in all dogs. FIG. 18 shows a typical example of the type of high amplitude spikes newly observed. Further investigation revealed that these epileptiform-like spikes precede the onset of ventricular tachycardia (VT). Repeated measurements revealed that the frequency of these spikes is about 6.6±0.77 HZ and their amplitude is about 0.91±0.16 mV.

Further investigation revealed that these epileptiform-like discharges induced premature ventricular contraction (PVC), as shown in FIG. 21, and that they are able to induce morphology changes of QRST, as shown in FIG. 22. FIG. 23 demonstrates that these epileptiform-like spikes precede the onset of ventricular tachycardia (VT) or premature ventricular contractions (PVCs). These unusual spikes induced non-sustained polymorphic ventricular tachycardia, fast accelerated idioventricular rhythm, premature ventricular contractions and nonsustained ventricular tachycardia.

These novel spikes are similar to the epileptiform discharges seen on electroencephalogram recordings in patients with seizure disorders. While epileptiform-like discharges are well known and characterized in the field of electroencephalography for the measurement of CNS activity, they have never heretofore been observed in electrocardiography. Significantly, while these high frequency spikes were seen in all dogs in the sudden death model group, they were rarely seen in any of the normal control dogs. These results show that abnormal SGNA is present in the stellate ganglion and that there is a causal relationship between abnormal SGNA and ventricular arrhythmias.

The SGNA recorded in the sudden death model was further analyzed. Of the dogs monitored, almost half died suddenly during follow-up. All dogs had phase-1 ventricular tachycardia (VT that occurred immediately post-infarct period) and phase-2 ventricular tachycardia (VT that occurred 10 days after myocardial infarction). Data Sciences International (DSI) monitoring showed that there were 1.4±1.1 phase-2 ventricular tachycardia episodes/day. Randomly selected phase-2 ventricular tachycardia episodes (N=205) from 4 dogs were analyzed. The results showed that 177 of 205 ventricular tachycardia episodes (86.3%) were preceded by elevated SGNA. The elevated SGNA was either high frequency activation or in the form of epileptiform-like discharges, demonstrating that the measurement of electrical activity can be used to predict the onset of arrhythmias.

In one embodiment, the sensor or electrode may be a nanoelectrode array. As shown in FIG. 1, the nanoelectrode array (10) comprising a plurality of nanoelectrodes (12). The signals from the sympathetic neural discharges are received by each of the nanoelectrodes, combined before digitization and transmitted by a single electrical wire (14). In a preferred embodiment, each individual nanoelectrode has a sharp tip of approximately 10 to 50 nm in diameter and is configured to penetrate the epineurium or the connective tissue sheath that surrounds the sympathetic nerve bundle without damaging the nerves and surrounding blood vessels. Akingba A G, Wang D, Chen P-S, Neves H, Montemagno C: Application of nanoelectrodes in recording biopotentials. Nanotechnology, 2003. *IEEE-NANO* 2003; 2:870-874

Figure 2:
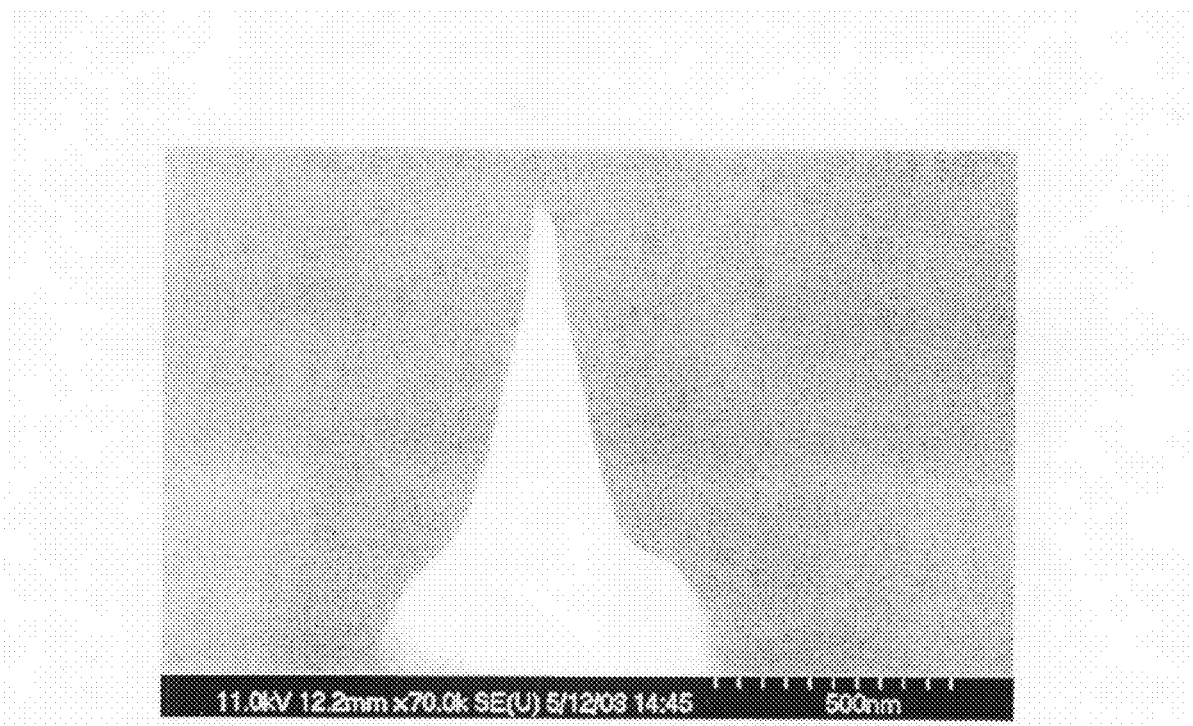
FIG. 2 is a magnified view of an individual tip from a nanoelectrode array.

FIG. 2 depicts an individual nanoelectrode from the nanoelectrode array having a diameter of approximately 50 nm. The tips of the nanoelectrode are placed directly on the LSG to record the sympathetic neural discharges. A nanoelectrode array provides the benefit of providing increased surface contact with the nervous tissue and improved signal-to-noise ratio.

Data acquired from the sensor or electrode may be filtered to produce optimal signal-to-noise ratio. The amplitude of a signal from a sympathetic nerve is typically −35 to +35 µV and the electrode noise is on average 10 µV for an ideal electrode resistance between 100 kΩ and 10 MΩ at 37° C. for a bandwidth of 1 kHz. Much of the noise during in vivo recording results from the interfacial effects between the neuron, epineurium, electrolyte and the electrode, which is dominated by the charge transfer resistance and the coupling resistance. Cross-talk from parasitic capacitances may also result in the generation of unwanted signals when using conventional electrodes to record sympathetic neural discharges.

Wide band pass filter (1 to 3000 Hz) allows recording of sympathetic neural discharges but also allows for a significant amount of noise generated by cardiac and respiratory related movement artifacts. A greater high pass filter setting (30 to 100 Hz) removes some of the noise and achieves a more stable baseline of the recorded sympathetic neural discharge signals.

The data acquired from the sensor or nanoelectrode may be continuously monitored to detect increases in the sympathetic neural discharges. In one embodiment, an increase in the sympathetic neural discharges in the patient may be determined by detecting an increase in the amplitude and frequency of the sensed sympathetic neural discharges beyond defined normal values. In another embodiment, an increase in the sympathetic neural discharges in the patient may be determined by comparing the parameters for the sensed sympathetic neural discharges in the patient with the parameters defined for normal sympathetic neural discharges. In yet another preferred embodiment, the electrical activity of the left stellate ganglion is monitored for epileptiform-like discharges. Due to the surprising discovery that these epileptiform-like discharges, which include the high-amplitude spikes represented in FIGS. 18-23, it is now possible to build a device that can record and diagnose these discharges. Such a device, for example an ICD, will be designed to include the function of the epileptiform-like discharge detection as part of its operation. In one embodiment, the device will have an extra connecting port to an electrode wire that records nerve activity from the left stellate ganglion. In this manner, the device will diagnose and quantitate the frequency and magnitude of the epileptiform-like discharges.

In an alternative embodiment, a wire electrode may be used to obtain SGNA recordings. SGNA recordings have been successfully obtained from the LSG, RSG, and vagal nerves implanting the stainless steel wires connected to the transmitter directly under the fascia of the stellate ganglia. A high degree of concordance between SGNA signals registered by the nanoelectrode array and by the stainless steel wires has been demonstrated. FIG. 8 depicts the correlation between SGNA recorded by nanoelectrode and the wire electrode from the LSG of a canine subject. An example of the actual left SGNA recordings from the nanoelectrode and the wire electrode is shown at the bottom of the bar graph. FIG. 8 demonstrates that SGNA may be adequately recorded using either the nanoelectrode array or the stainless steel wire electrode.

The defined normal value represents a value above and beyond which is indicative of an impending arrhythmic condition of the heart and may be determined with reference to the normal baseline sympathetic neural discharge. For example, a two-fold or greater increase in the amplitude of the sensed sympathetic neural discharge from the normal baseline amplitude of sympathetic neural discharge may be used as a suitable defined normal value. A second defined normal value with respect to the frequency of the sympathetic neural discharge may be similarly provided. The defined normal values may be a preset or user-defined programmable value.

Once an increase in the sympathetic neural discharges, such as epileptiform-like high amplitude spikes, has been detected, an output signal may be generated. In one embodiment, the output signal may be an audible sound, a radio-transmitted or radio-frequency signal, an electrical signal, or any other type of signal that would alert the patient or physician to the possibility of an impending arrhythmia or other diseased condition of the heart associated with elevated sympathetic neural discharge. Upon the generation of the output signal, the patient or physician may then take precautionary or therapeutic measures to avoid or reduce the likelihood of an impending cardiac arrhythmia or other diseased condition of the heart. Alternatively, the device may transmit the detection of the epileptiform-like discharges from the left stellate ganglion via telephone or the internet to the physician's office. The physician can then adjust the drug dosage according to the information transmitted by the device and thus prevent ischemia or sudden death.

In another embodiment, the output signal may be a command signal directing the delivery of suitable therapy. Suitable therapy for use in connection with the methods and systems are known in the art and may include any one or a combination of the following: delivering one or more pharmacological agents; stimulating myocardial hyperinnervation in the sinus node and right ventricle of the heart of the patient; and cardiac pacing, cardioversion, or defibrillation shocks. A suitable drug delivery system for an implantable cardiac device is disclosed in U.S. Pat. No. 6,361,522, which is incorporated herein in its entirety. Thus, the device can be used to trigger an implantable drug delivery device which automatically delivers anti-arrhythmic medications according to the frequency and magnitude of the epileptiform-like discharges. In another preferred embodiment, the device is used to trigger the delivery of stimulation signals to the right stellate ganglion in order to suppress the epileptiform discharge, as the right stellate ganglion is believed to exert an anti-arrhythmic effect.

Pharmacologic agents may include those which are known to exert an anti-arrhythmic effect, such as sodium channel blockers, β-blockers, potassium channel blockers, such as amiodarone and solatol, and calcium channel blockers, such as verapamil and diltiazem.

Other suitable anti-arrhythmic pharmacologic agents include anti-convulsant agents, such as phenytoin, carbamazepine, valproate, and phenobarbitone. The LSG is capable of high frequency neuronal discharges and these discharges directly increase heart rate. Anti-convulsants work by selectively suppressing high frequency neuronal discharges in the central and peripheral nervous system. Anti-convulsants are also known to suppress cardiac sympathetic nerve discharges. Because of the importance of the autonomic nervous system in arrhythmogenesis, drugs that prevent the release of adrenergic neurotransmitters may thereby decrease the sympathetic outflow are useful for controlling cardiac arrhythmia.

It has been shown, for example, that phenytoin can also be used to suppress cardiac arrhythmia induced by digitalis toxicity. The action of phenytoin is related to use- and frequency-dependent selective suppression of high-frequency neuronal activity. The molecular mechanism for this is a voltage-dependent blockade of membrane sodium channels responsible for the action potential. Through this action, phenytoin obstructs the positive feedback that underlies the development of maximal seizure activity.

Anti-convulsants may block the sympathetic nerve discharges through two actions. One is frequency-dependent block of sodium currents and the second is a block of calcium currents. A combined channel blockade may account for the effects of anticonvulsant drugs. In addition to epilepsy, anti-convulsants, such as phenytoin and carbamazepine, are also useful in treating neuropathic pain, which is characterized by abnormal spontaneous and increased evoked activity from damaged areas of the peripheral nervous system.

Other suitable pharmacologic agents may also be used for the treatment of myocardial ischemia and may include, but are not limited to, statins, angiotensin-converting enzyme (ACE) inhibitors, aspirin, beta blockers, calcium channel blockers, and nitrates. Any other suitable pharmacologic agent, that is known to treat a diseased condition of the heart associated with elevated sympathetic neural discharges, may be used in combination with any other pharmacologic agent and/or therapy.

Anti-arrhythmic therapy may also be administered by stimulating myocardial hyperinnervation in the sinus node and right ventricle of the heart of the patient by applying electrical stimulation to the RSG of the patient or by applying Nerve Growth Factor or other neurotropic substances to the RSG, as disclosed in U.S. Pat. No. 6,487,450, which is incorporated herein in its entirety.

The methods disclosed herein may be carried out by a programmable implantable or external device, including, but not limited to, implantable cardiac rhythm management systems such as pacemakers, cardioverters, ICDs, and the like. In one embodiment, the system may comprise a microprocessor, memory, bi-directional data bus, a sympathetic nerve activity (SNA) sensing unit, an output unit and a telemetry interface.

The microprocessor may communicate with the memory through the data bus and execute the program stored in the memory. The microprocessor may include a comparator, such as a summing amplifier, operation amplifier, or other methods of comparing the levels of analog voltage signals. Furthermore, if the sensors or the electrodes produce digital values reflecting the sympathetic neural discharges, then numerous methods known to one of skill in the art may be utilized to digitally compare the respective sympathetic neural discharges.

The memory may comprise any suitable combination of read-only memory (ROM) containing the device operating software, random access memory (RAM) for data storage, and on-board or off-board cache memory associated with the microprocessor. The data bus permits communication between the microprocessor, memory, SNA sensing unit, output unit and the telemetry interface. The telemetry interface may be used for downloading stored data to an external programmer and for receiving telemetry from the programmer to modify programmable parameters and/or change the device operating software.

The SNA sensing unit may comprise one or more electrodes or sensors coupled to sympathetic nerves of the patient, such as the LSG, and interface circuits that receive and process the sensed signals from the electrodes. Accordingly, the SNA sensing unit may receive electrical signals from the sympathetic nerves of the patient, filter those signals, and convert them into digital data or otherwise make the data available to the microprocessor.

Accordingly, in one embodiment, the microprocessor may instruct the SNA sensing unit to collect data from the sympathetic nerve, which is then transmitted over bus to the microprocessor for immediate processing or to the memory for storage and subsequent processing as appropriate. The microprocessor may then execute the programming resident in memory to identify increases in the sympathetic neural discharges of the patient and command the output unit to produce an output signal in response thereto.

The methods and systems illustrated with reference to the drawings and described herein are merely illustrative of the principles of the invention which may be implemented in alternative embodiments to achieve other ends than those specifically described herein. Accordingly, the following examples are set forth for the purpose of illustration only and are not construed as limitations on the method disclosed herein.

EXAMPLE 1

Rabbit Renal Sympathetic Nerve Recordings

A standard wire electrode and a nanoelectrode array was implanted on the renal sympathetic nerve of a New Zealand white rabbit. Simultaneous recordings of the ECG and renal sympathetic neural discharges were obtained. The renal sympathetic neural discharges was recorded with both a standard wire electrode and a nanoelectrode array and amplifier. The signals were digitized with a band pass filter of 30 to 500 Hz and a digitization rate of 1 K/sec.

Figure 3:
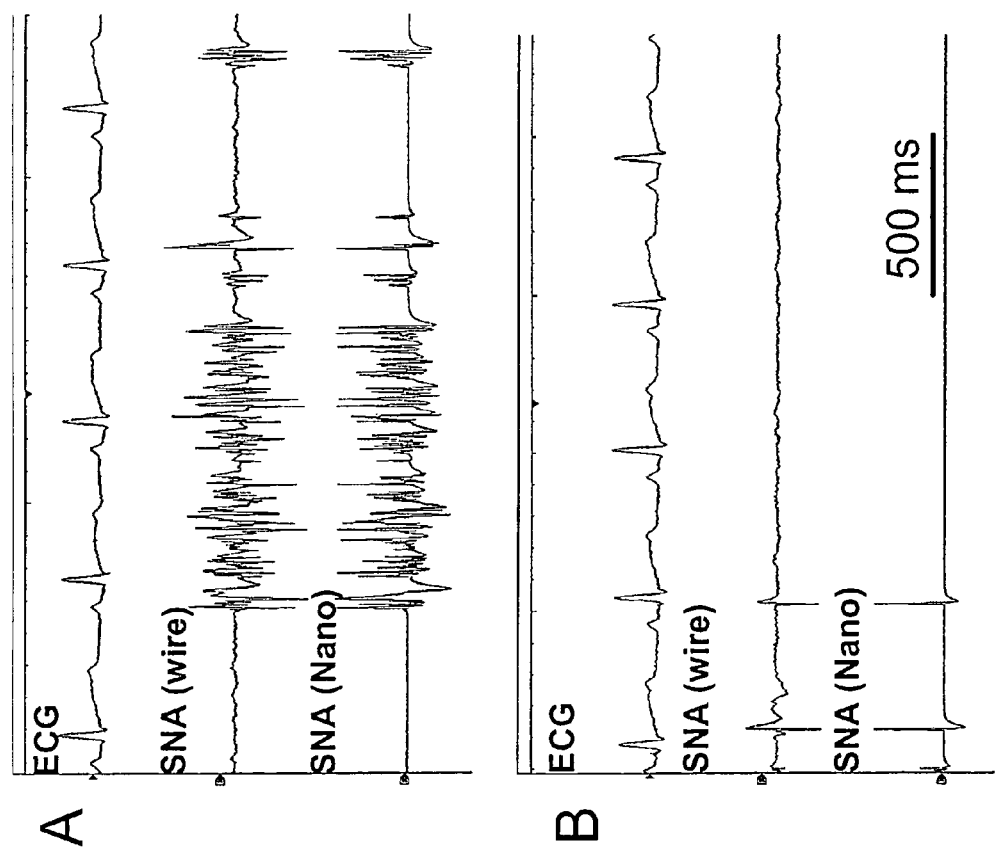
FIG. 3 depicts simultaneous recordings of (a) renal sympathetic neural discharges obtained from a wire electrode and a nanoelectrode and (b) electrocardiograph (ECG) recordings obtained from a rabbit subject over a time span of 2 seconds.

FIG. 3 shows the ECG and renal sympathetic neural discharge recordings obtained from the rabbit. The nanoelectrode recordings provided a lower baseline noise than the wire electrode and therefore a higher signal-to-noise ratio. FIG. 3A shows bursts of renal sympathetic neural discharges, which did not correlate with changes in the heart rate. FIG. 3B shows the suppression of renal sympathetic neural discharges by intravenous bolus dose of xylazine and ketamine.

EXAMPLE 2

Sympathetic Neural Discharges of the Left Stellate Ganglion and Heart Rate Control The relationship between the SGNA of the LSG and the heart rate was investigated in a normal canine subject. A normal canine subject was anesthetized with isoflurane and the chest was opened at the third intercostal space. The LSG was identified and a nanoelectrode was implanted under the fibrous capsule. The fibrous capsule was then closed with a 4-0 silk suture and additional sutures were placed on the wire to secure the nanoelectrodes. The nanoelectrodes were then connected to a DSI transmitter (DSI TL 10M3-D70-EEE, Data Sciences, International) with a low pass filter of 250 Hz and a digitization rate of 1 K/sec. An additional bipolar channel of the DSI transmitter was used for ECG recordings between the right and left chest. All recordings shared a common ground.

Figure 4:
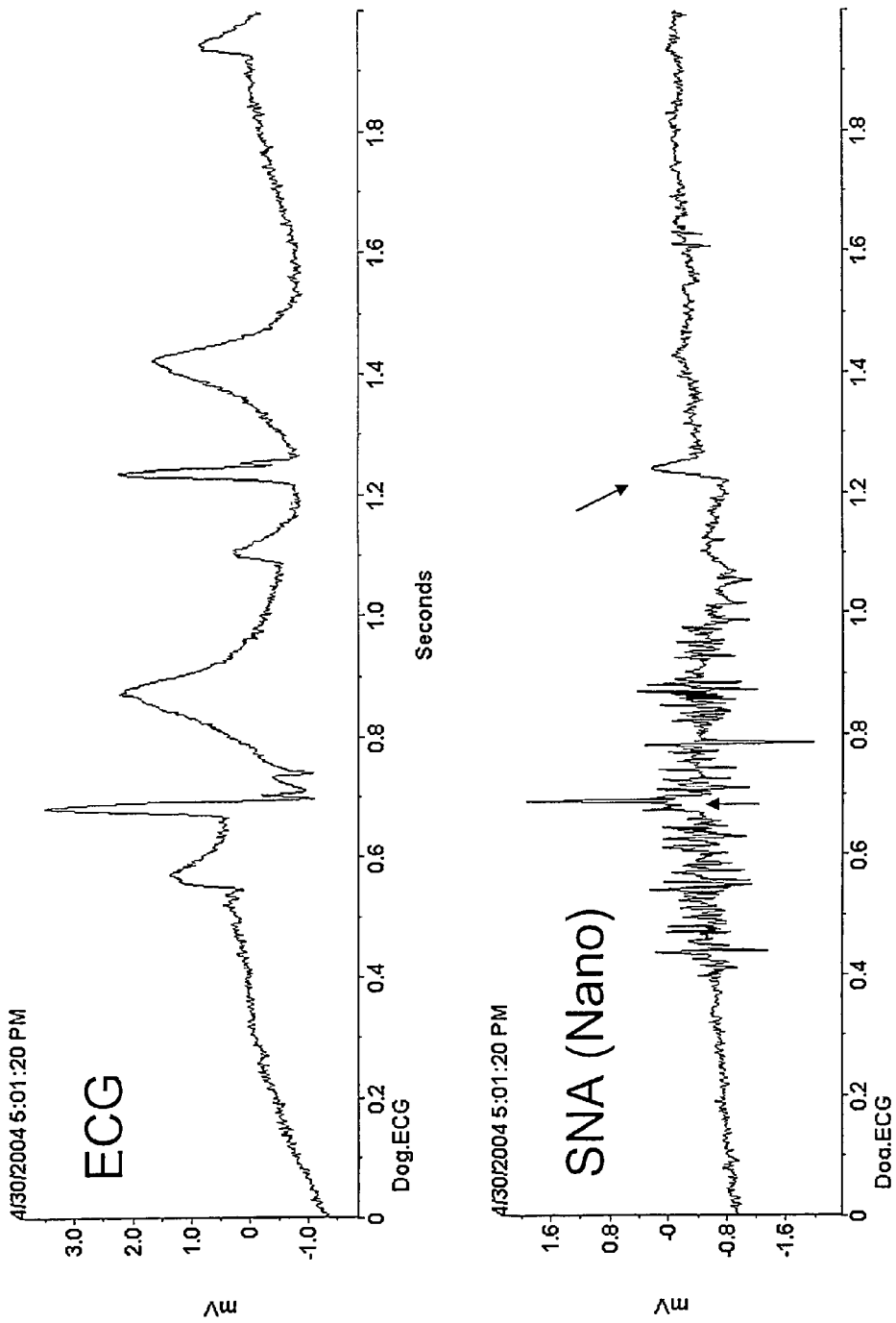
FIG. 4 depicts simultaneous recordings of ECG and SGNA from the LSG of an ambulatory normal canine subject two weeks after implantation of the nanoelectrode to the LSG. A burst of SGNA preceded the onset of accelerated atrial rate by approximately 0.2 seconds. The arrow indicate cross-talk from the surface ECG, which shared the same ground as the nanoelectrode.

FIG. 4 shows the relationship between the SGNA of the LSG and heart rate in an ambulatory normal canine subject two weeks after implantation of the nanoelectrode in the LSG. Bursts of SGNA preceded the onset of accelerated atrial rate by approximately 200 ms (0.2 seconds). The arrow points to cross-talk from the surface ECG, which shared the same ground as the nanoelectrode.

Figure 5A:
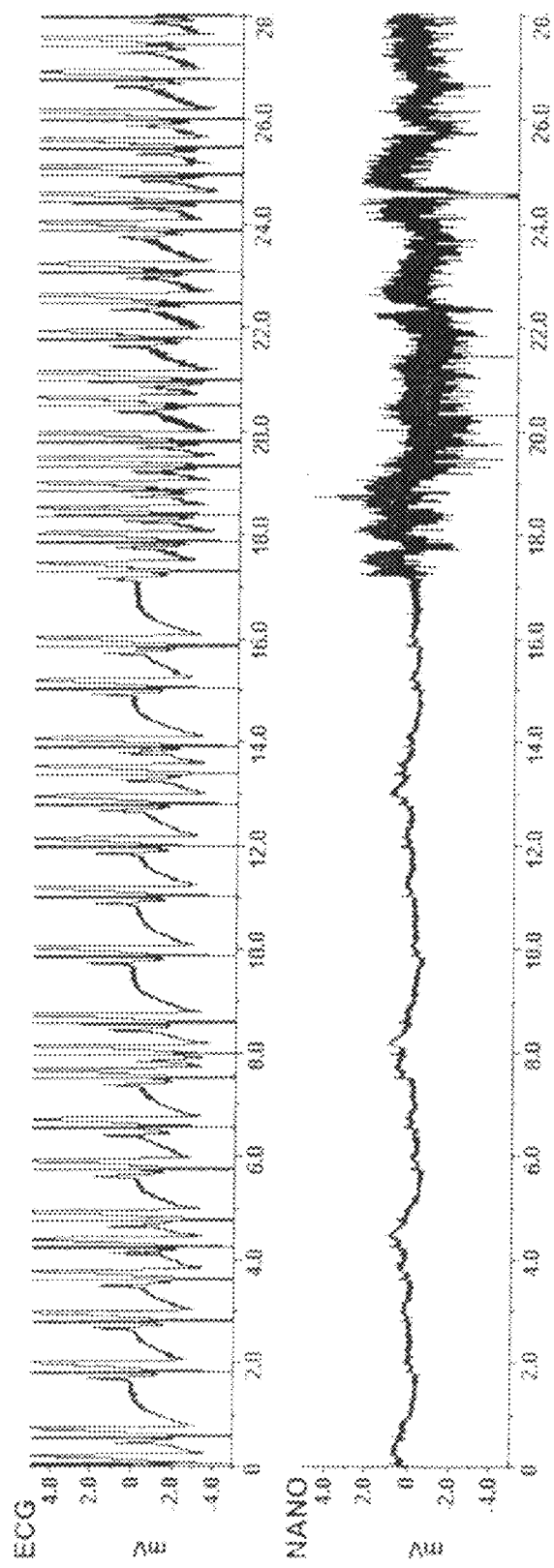
FIGS. 5A-C depict three separate simultaneous recordings of ECG and SGNA recorded from a nanoelectrode implanted at the LSG of an ambulatory normal canine subject over a time span of 28 seconds. The onset of increased SGNA (as designated by (a) through (h)) is followed by increased heart rate.
Figure 5B:
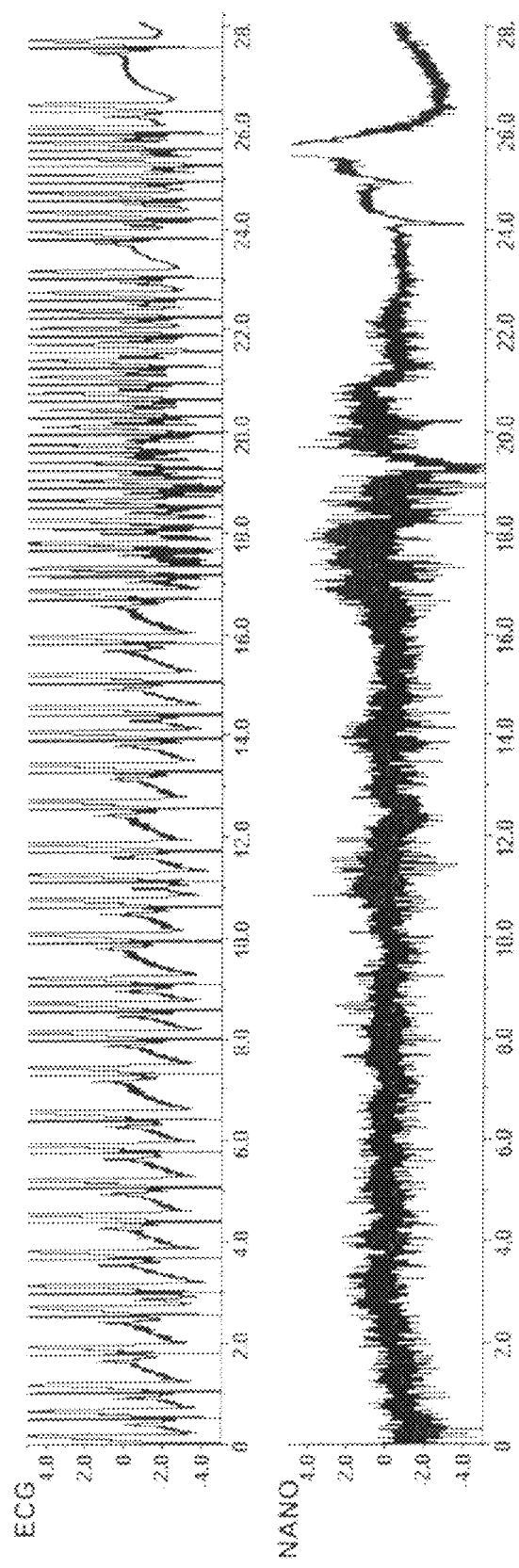
Figure 5C:
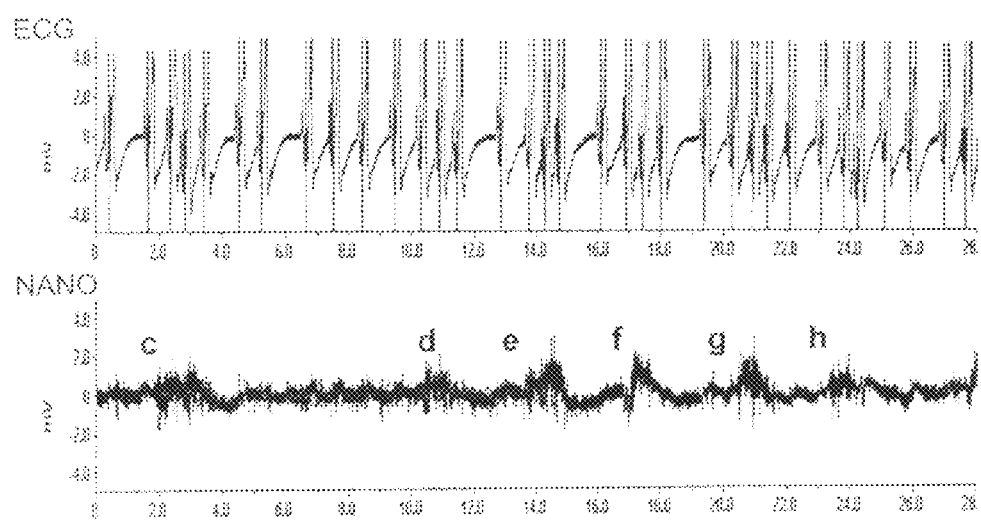

FIGS. 5A-C depict three separate simultaneous recordings of ECG and SGNA recorded from a nanoelectrode implanted at the LSG of an ambulatory normal canine subject over a time span of 28 seconds. The onset of increased SGNA (as designated by (a) through (h)) is followed by increased heart rate. FIG. 5A shows the onset of increased SGNA at time (a) which was followed by an increase in heart rate. FIG. 5B shows the increase in amplitude of the SGNA signals at (b) which is followed but further increases in heart rate. FIG. 5C shows burst increases in the amplitude of SGNA signals at (c), (d), (e), (f), (g), and (h), all of which were followed by short runs of increased atrial rate. This demonstrates that increased SGNA is causally related to increased heart rate.

Figure 6:
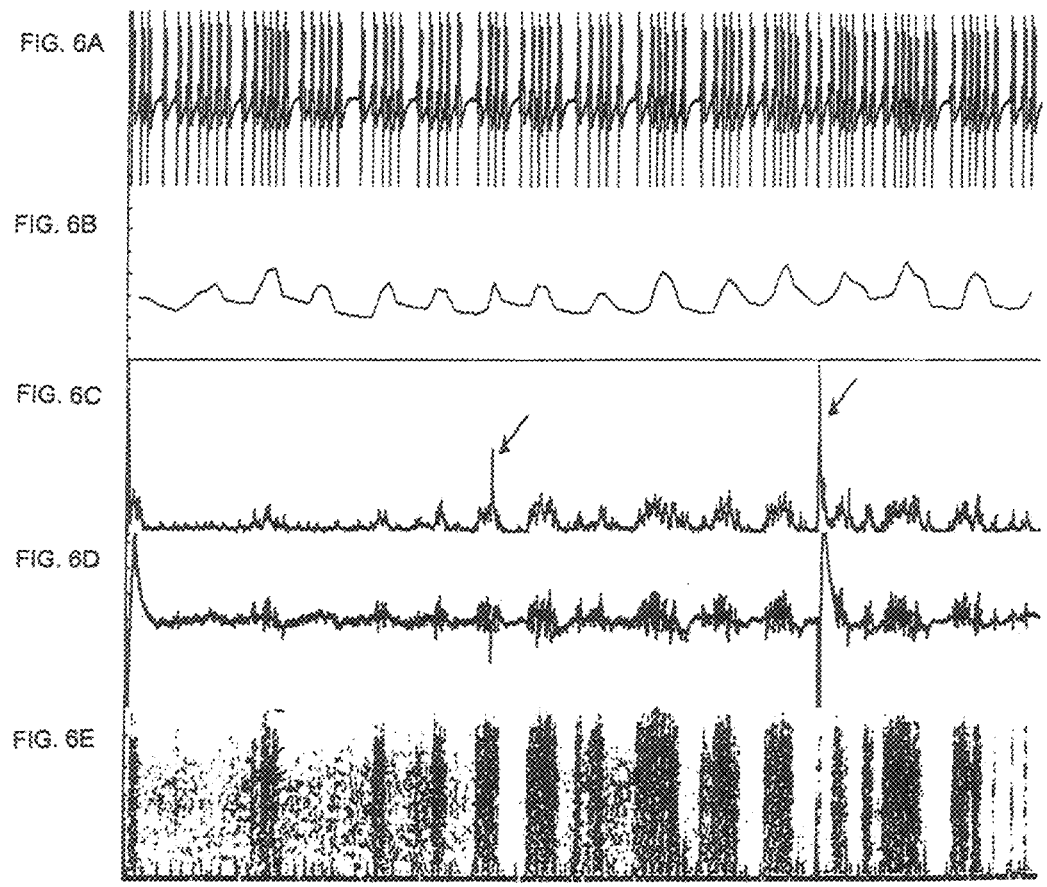
FIGS. 6A-E show the simultaneous 60 second recordings of (A) ECG, (B) the heart rate in beats per second, (C) the integrated SGNA, (D) the raw SGNA signals and (E) the sonogram (frequency in the Y-axis and power in shades of grey) obtained from an ambulatory normal canine subject.

FIGS. 6A-E shows a correlation between heart rate and the integrated SGNA. FIG. 6A depicts the ECG recording; FIG. 6B depicts the heart rate in beats per minute; FIG. 6C depicts the integrated nerve recording and FIG. 6D depicts the raw nerve signal and panel FIG. 6E depicts the sonogram. The frequency of the sonogram in panel FIG. 6E is provided in the Y axis and the power is indicated by the gray shading. A correlation is observed between the heart rate and integrated SGNA signal and between the heart rate and the sonogram.

Figure 7:
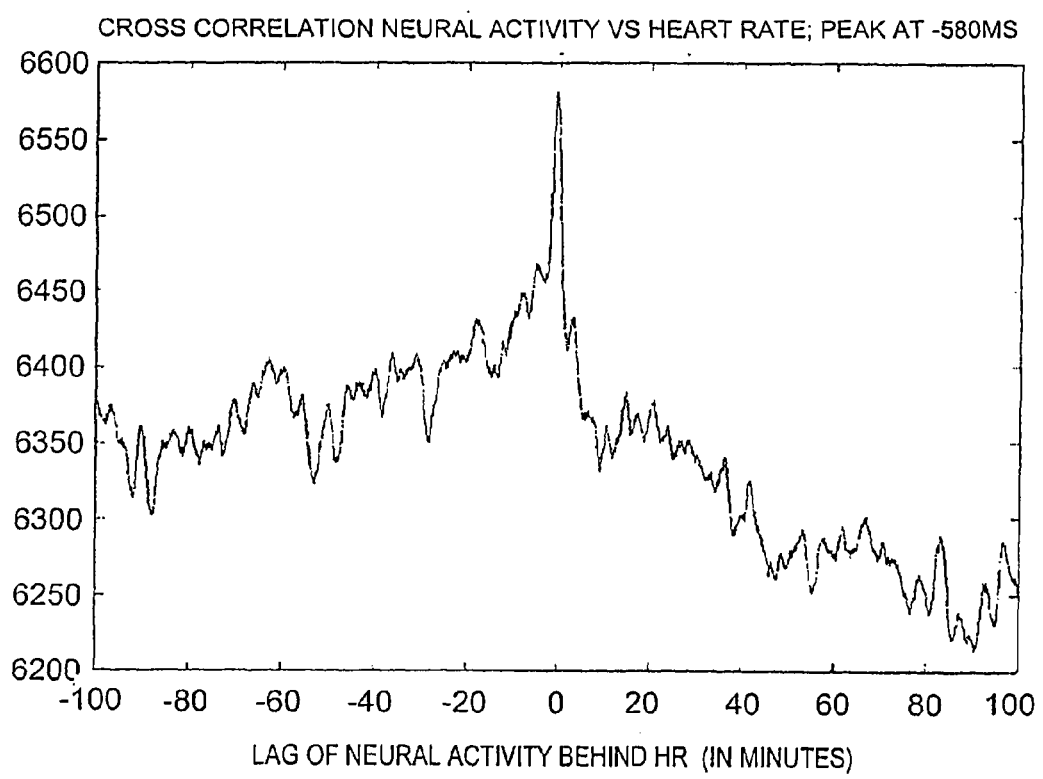
FIG. 7 shows the cross-correlation between SGNA and heart rate over a one hour period.

FIG. 7 depicts the cross-correlation between the SGNA and the heart rate over an hour. The onset of heart rate changes were defined by the S wave of the QRS complex. The peak correlation occurred at −580 ms, indicating that the increased sympathetic neural discharges is followed within 580 ms by an increased heart rate. The P waves occurred approximately 180 ms before the S wave on the QRS complex. Therefore, the increase in the SGNA occurred approximately 400 ms before the onset of the P wave.

EXAMPLE 3

Relationship Between Sympathetic Neural Discharges and Heart Rate and Blood Pressure in Normal Canine Subjects Stellate ganglion nerve activity (SGNA) of six (6) purpose bred class-A adult mongrel dogs (18-25 kg) was monitored used to study the relationship between SGNA and heart rate and blood pressure; the circadian variations of SGNA; and the effects of electrical stimulation of the stellate ganglia.

Sterile surgery was performed under general anesthesia. A DSI transmitter was used to record a total of 3 channels of electrograms. The sampling rate was 1,000/s and each of the biopontential channels had a bandwidth of 1-100 Hz and shared the same ground wires implanted in the subcutaneous pocket near the transmitter.

The DSI transmitter model D70-EEE was used for five of the canine subjects to record one channel of SGNA from the LSG, one channel of SGNA from the RSG and one channel of ECG. The recording electrodes were implanted under the fascia of the stellate ganglia and connected to a subcutaneous DSI transmitter to obtain continuous SGNA recordings. One pair of widely spaced bipolar wires was implanted to the subcutaneous tissues to record electrocardiogram. In one of the canine subjects, a nanoelectrode array was implanted under the fascia of the LSG for SGNA recordings and the nanoelectrode array was soldered to the stainless steel wires connected to the DSI transmitter. In the remaining canine subjects, the SGNA from the LSG and RSG were recorded using the bare wires that came with the DSI transmitter. FIG. 8A shows the strong correlation between the SGNA signals obtained from the LSG of a normal canine subject by nanoelectrode array and by stainless steel wire. An example of the actual SGNA recordings from the nanoelectrode and wire electrode is further depicted at the bottom of the bar graph. FIG. 8 demonstrates that SGNA may be adequately recorded using either the nanoelectrode array or the stainless steel wire electrode.

The DSI transmitter model D70-CCP was used for one canine subject to record one channel of SGNA from the LSG, one channel of ECG and one channel of blood pressure. In this canine subject, a blood pressure transducer was implanted into the descending aorta through a puncture hole in the left subclavian artery and the hole was then closed with a purse-string suture.

Manual and automated methods were used to examine the data obtained from the DSI transmitter. Manual analyses were used for short (up to 10 minute) segments of unprocessed raw data to correlate the sympathetic discharges with changes in blood pressure and heart rate. Automated analyses were performed using custom written software. During offline analysis, the sampled SGNA signal was digitally filtered between 25 and 150 Hz with an 8th order elliptical band-pass filter implemented in MATLAB (Mathworks, Natick, Mass.). The resulting signal was then full-wave rectified. A scalar value representing the average level of the SGNA was derived from the average value of this rectified and filtered signal.

Figure 9:
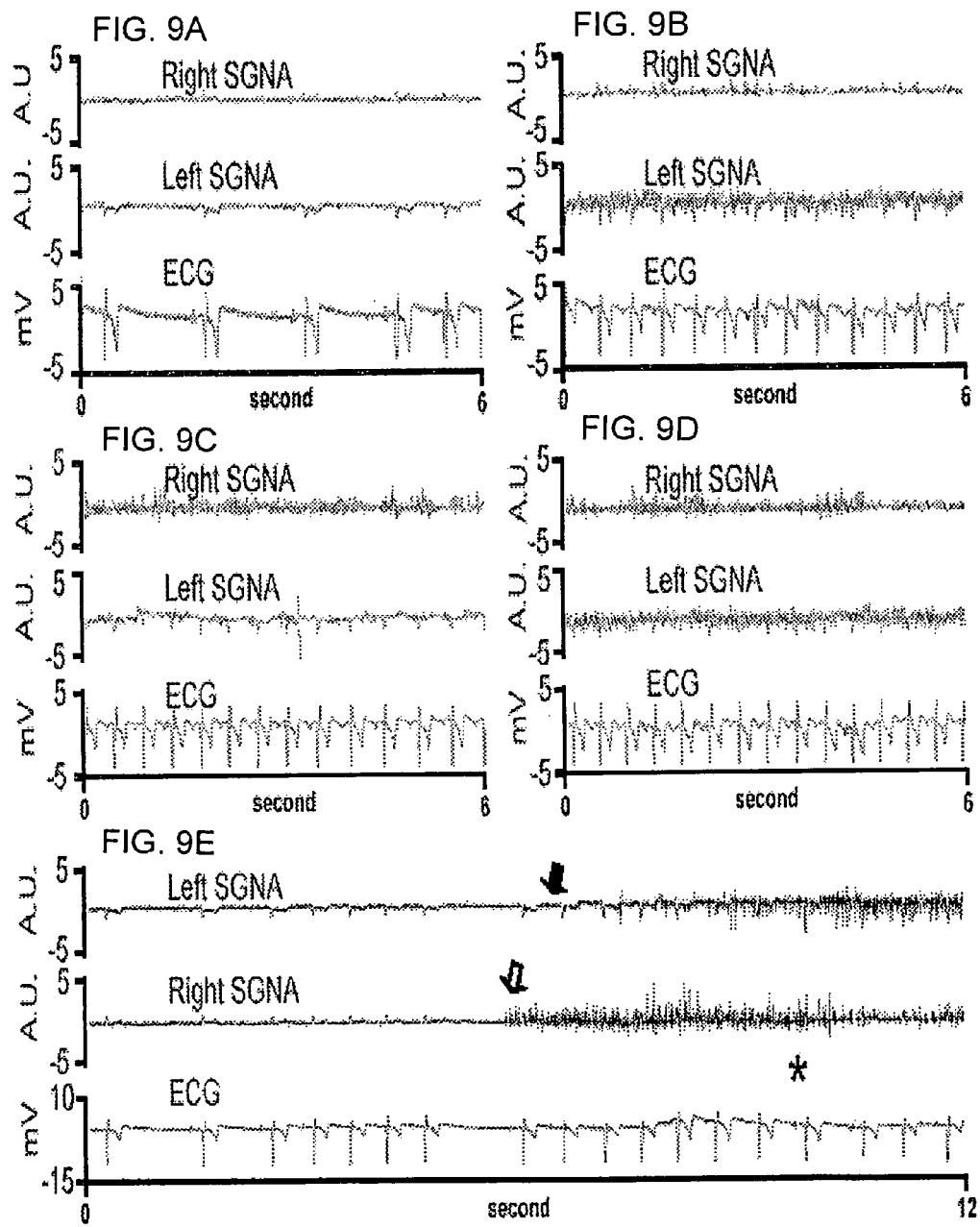
FIGS. 9A-E show the relationship between the SGNA (as a function of time and artificial units A.U.) and heart rate (as a function of time and mV) in an ambulatory normal canine subject.

The successful recording of SGNA is confirmed by a strong relationship between the signals registered from the stellate ganglia and the heart rate responses in all canine subjects studied. FIGS. 9A-E show continuous tracings of SGNA recordings from the RSG and the LSG and the concurrent electrocardiogram (ECG) from a normal canine subject. FIG. 9A show the baseline SGNA recording, which shows the absence of SGNA from the RSG and LSG, and the concurrent ECG, which shows a slow heart rate with significant sinus arrhythmia. FIGS. 9B-D show the increased SGNA recordings during rapid heart rate. Specifically, rapid heart rate is associated with increased left SGNA and sporadic right SGNA (FIG. 9B), increased right SGNA and sporadic left SGNA (FIG. 9C) and increased bilateral (left and right) SGNA (FIG. 9D).

FIG. 9E shows the onset of bilateral SGNA, followed by an increase in the heart rate. As further observed in FIG. 9E, the onset of the right SGNA preceded the onset of the left SGNA (as indicated by the arrows) and gradual deceleration and significant irregularity were observed in the heart rate (as indicated by the asterisk) in spite of continued bilateral SGNA. Similar results were demonstrated in one hundred randomly selected episodes of SGNA onset from three normal canine subjects with bilateral SGNA recordings, in which 90% were bilateral SGNA episodes where the right SGNA preceded the left SGNA by 300-900 ms and 10% were unilateral SGNA episodes.

The relationship between SGNA from the LSG and the heart rate are further demonstrated in the continuous recordings of heart rate, blood pressure and SGNA from the LSG in a normal canine subject, as shown in FIGS. 10A-E. FIGS. 10A-C are continuous recordings obtained from an ambulatory normal canine subject fifteen (15) days after implantation of the stainless steel wire electrode. In FIG. 10A, the increase in SGNA at (a) was followed by an increase in heart rate. In FIG. 10B, further increases in SGNA at (b) resulted in further increases in heart rate. In FIGS. 10C-D, brief bursts of SGNA at (c) were followed by immediate acceleration in heart rate. The arrows point to possible motion artifacts. FIG. 10E show the relationship between SGNA and blood pressure at baseline (d), unilateral increase in SGNA from the RSG at (e) and bilateral increase in SGNA from both the LSG and RSG at (f). Again, a stainless steel wire electrode was used to obtain the SGNA recordings.

EXAMPLE 4

Circadian Variations in SGNA and Heart Rate in Normal Canine Subjects

There is a circadian variation of the incidence of sudden cardiac death. One possible explanation for this circadian variation may be the pattern of sympathetic activity. High sympathetic tone in the daytime may trigger the onset of ventricular arrhythmia. This is supported by the finding that circadian variation of sudden cardiac death or fatal myocardial infarction is substantially eliminated by administering propanolol in patients with heart disease and complex ventricular arrhythmia. Aronow W S, et al.: Circadian variation of sudden cardiac death or fatal myocardial infarction is abolished by propanolol in patients with heart disease and complex ventricular arrhythmias. Am. J. Cardiol. 1994; 74:816-821.

Circadian variations of SGNA were studied by analyzing the SGNA recordings from the LSG and RSG of normal ambulatory canine subjects. The SGNA recordings obtained from the canine subjects were filtered to eliminate artifacts and far field ECG signals. The filtered SGNA signals were then subjected to automated analyses to determine the SGNA amplitude. Data from one week of continuous SGNA recordings were pooled together and averaged for each hour of the day. The SGNA recordings were then normalized to the SGNA recording at hour 0 (midnight).

FIGS. 11A-B shows the averaged hourly heart rate and SGNA (as a ratio to the SGNA at hour 0), respectively, at baseline plotted over a 24 hour period in six normal canine subjects. A statistically significant circadian variation was present during the 24 hours for both heart rate and SGNA recordings. ANOVA showed a significant difference during the 24 hour period for both heart rate and SGNA. The orthogonal polynomials were then computed. The natural polynomial for a simple circadian pattern is quadratic. For the heart rate variable, the quadratic term accounted for 79% of the between time sum of squares and the quadratic term for the SGNA accounted for 70% of the between time sum of squares.

EXAMPLE 5

Effect of Electrical Stimulation of the Stellate Ganglia in Normal Canine Subjects Upon completion of the drug tests, the canine subjects were anesthetized with isofluorane. The subcutaneous pocket was opened and the electrical wires leading to the stellate ganglion were cut. These wires were used for electrical stimulation and for recording SGNA using a Prucka Cardiolab system. The signals were acquired at 979 samples per second. The high pass and low pass filter settings were 30 and 500 Hz, respectively. A catheter in the femoral artery was used for monitoring blood pressure. After baseline SGNA, surface ECG and femoral blood pressure was measured simultaneously for a 30 minute period, electrical stimulation (5-50 mA, 5 ms pulse width at 20 Hz) was applied for 30 seconds through the implanted wires to the stellate ganglia.

Electrical stimulation of the stellate ganglia resulted in abrupt increases in heart rate and blood pressure in all normal canine subjects. FIG. 12 shows the effects of electrical stimulation in one canine subject. No spontaneous SGNA was observed before commencement of electrical stimulation. LSG and RSG stimulation resulted in significantly increased blood pressure which persisted after electrical stimulation. As shown in FIG. 12A, a 50 mA current administered to the LSG resulted in an immediate increase in blood pressure, whereas in FIG. 12B, a 50 mA current administered to the RSG resulted in an increase in blood pressure within about 5 seconds.

At the end of the electrical stimulation, the stimulated stellate ganglion showed no electrical activity, but the contralateral stellate ganglion showed continuous discharges associated with persistently elevated blood pressure and heart rate. These discharges may persist from 3 to 20 minutes and suggest that the LSG and RSG communicate with each other through synapses in the spinal cord. These findings are also consistent with the observation that the SGNA from the LSG and RSG usually occur together, although the SGNA from the RSG may precede earlier than the SGNA from the LSG in most cases.

As shown in FIG. 12C, transient ST segment elevation in the recorded ECG was also observed during electrical stimulation, indicating significant myocardial ischemia, probably as a combined result of alpha-receptor induced coronary constriction and beta-receptor mediated increase in oxygen consumption.

In two of the three canine subjects with bilateral SGNA recordings, electrical stimulation of the stellate ganglion on one side resulted in persistent SGNA of the contralateral stellate ganglion. In other words, electrical stimulation of the stellate ganglion on one side resulted in persistent SGNA of the contraleteral stellate ganglion.

EXAMPLE 6

Effect of Drug Perturbations on SGNA in Normal Canine Subjects

Beta-blocker (nadolol) therapy was administered to all six normal canine subjects. The results showed that the averaged heart rate reduced from 99+8 bpm at baseline to 88+9 bpm during nadolol therapy (n=6, p=0.001). Heart rate reduction was observed in all six canine subjects studied. However, the averaged SGNA from the1 LSG during nadolol therapy as a ratio of baseline SGNA was 0.96+0.09 (n=6, p=0.07).

Nitroprusside was also administered to the canine subjects via intravenous line infusion and resulted in transient reduction in blood pressure and a modest increase in SGNA. Phenylephrine infusion was observed to increase blood pressure and decrease SGNA. Thus, SGNA was higher during nitroprusside infusion as compared to during phenylephrine infusion.

EXAMPLE 7

Relationship Between SNGA and VT, VF and SCD in Canine Models for SCD

Continuous sympathetic nerve recordings were also obtained from four (4) canine models for sudden cardiac death. A canine model for sudden cardiac death is disclosed in U.S. Pat. No. 6,351,668, which is incorporated herein by reference. The circumstances under which sudden cardiac death occurs in canine subjects are similar to circumstances under which sudden cardiac death occurs in human patients. Accordingly, a canine SCD model may be used to analyze and identify conditions within the heart leading up to a ventricular tachycardia or ventricular fibrillation of the type leading to sudden cardiac death, as disclosed in U.S. Pat. No. 6,353,757, which is incorporated herein by reference. A canine SCD model may also be used to develop and test the effectiveness of new techniques for preventing a ventricular tachycardia, ventricular fibrillation or sudden cardiac death from occurring, as disclosed in U.S. Pat. No. 6,398,800 and pending U.S. application Ser. No. 10/033,400, filed Dec. 12, 2001, which are incorporated herein by reference.

The canine SCD model is created by inducing myocardial hyperinnervation within the LSG in combination with creating a complete atrioventricular (AV) block and inducing a relatively mild myocardial infarction (MI). The AV block is typically created by ablating the AV node of the heart using an ablation catheter and the MI is induced by ligating the left anterior descending portion of the coronary artery. Myocardial hyperinnervation is stimulated by application of nerve growth factor (NGF) or other neurotrophic vectors to the LSG. Alternatively, electrical stimulation signals may be applied to the LSG.

By creating an AV block and by inducing an MI within the heart of an adult canine test subject, and then by stimulating nerve growth within the LSG of the subject using NGF, a significant increase in the likelihood of SCD arising from phase two ventricular arrhythmias has been observed. Thus, the method permits SCD to be induced within test animals in a manner facilitating the collection of data pertinent to conditions within the heart arising prior to SCD and for testing techniques intended to prevent phase two VT and VF within patients subject to a previous MI.

In the SCD model canine subjects, SGNA recordings from the LSG were obtained from the stainless steel wires of the DSI model D70-EEE transmitter implanted under the fascia of the LSG. ECG recordings were obtained by connecting two biopotential channels of the DSI transmitter to local left ventricle and left atrial recordings, respectively.

Figure 13:
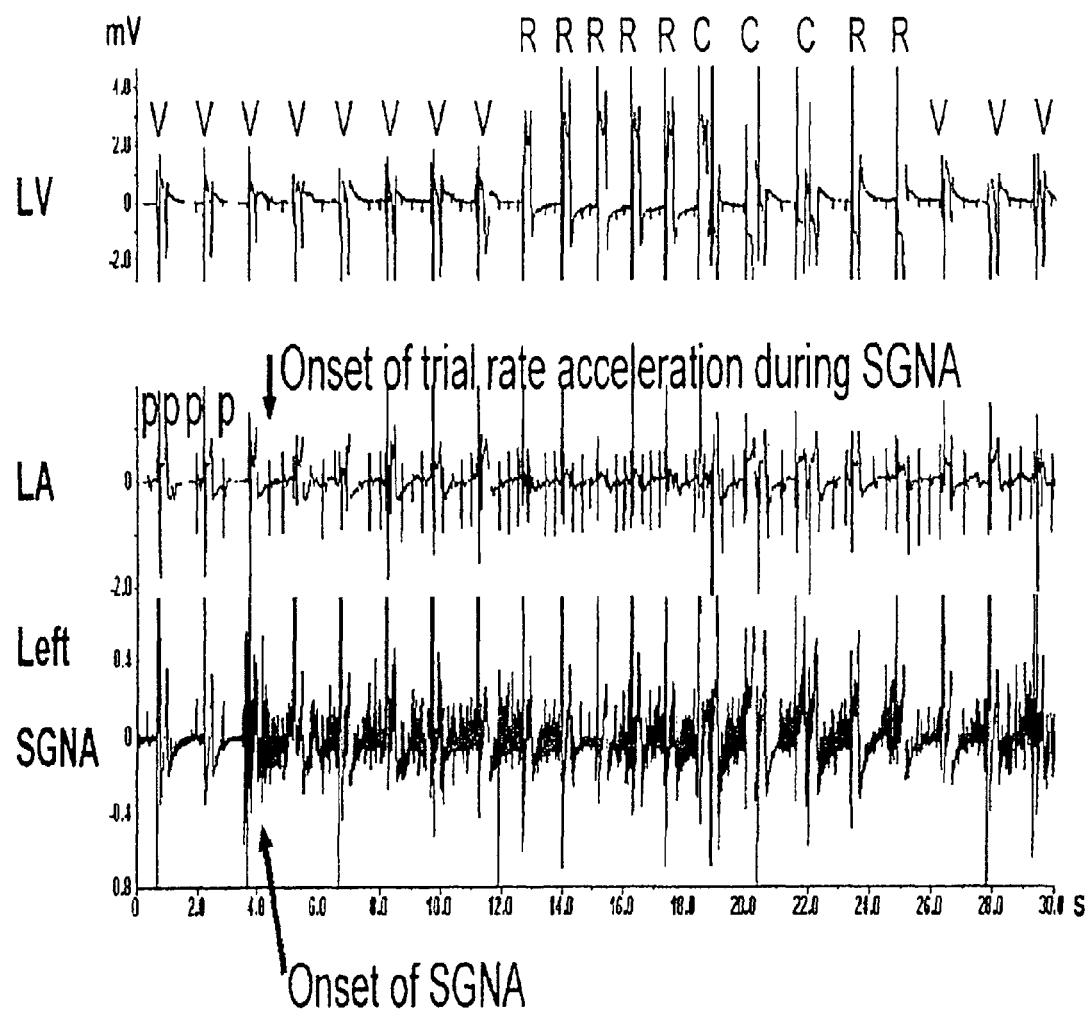
FIG. 13 is a 30 second simultaneous bipolar left ventricle (LV) and left atrial (LA) electrogram and SGNA using a stainless steel wire electrode implanted in the LSG of a canine SCD model (complete atrioventricular block, myocardial infarction and nerve growth factor infusion to the LSG) taken four weeks after surgery. Before the onset of increased SGNA, the ventricles were paced at 40 bpm (V) while there was dissociated sinus rhythm (P). The onset of increased SGNA was followed by abrupt increase in atrial rate and the development of ventricular escape rhythm (R) and 3 couplets (C).

FIG. 13 is a 30 second recording of SGNA from the LSG in a SCD canine model. This recording was taken four weeks after the first surgery. Bipolar left ventricle (LV) and left atrial (LA) electrograms were recorded simultaneously with left SGNA. Before the onset of left SGNA, the ventricles were paced at 40 bpm (V) while there was dissociated sinus rhythm (P). The onset of left SGNA was followed by an abrupt increase of atrial rate and the development of a ventricular escape rhythm (R) and three couplets (C).

Figure 14A:
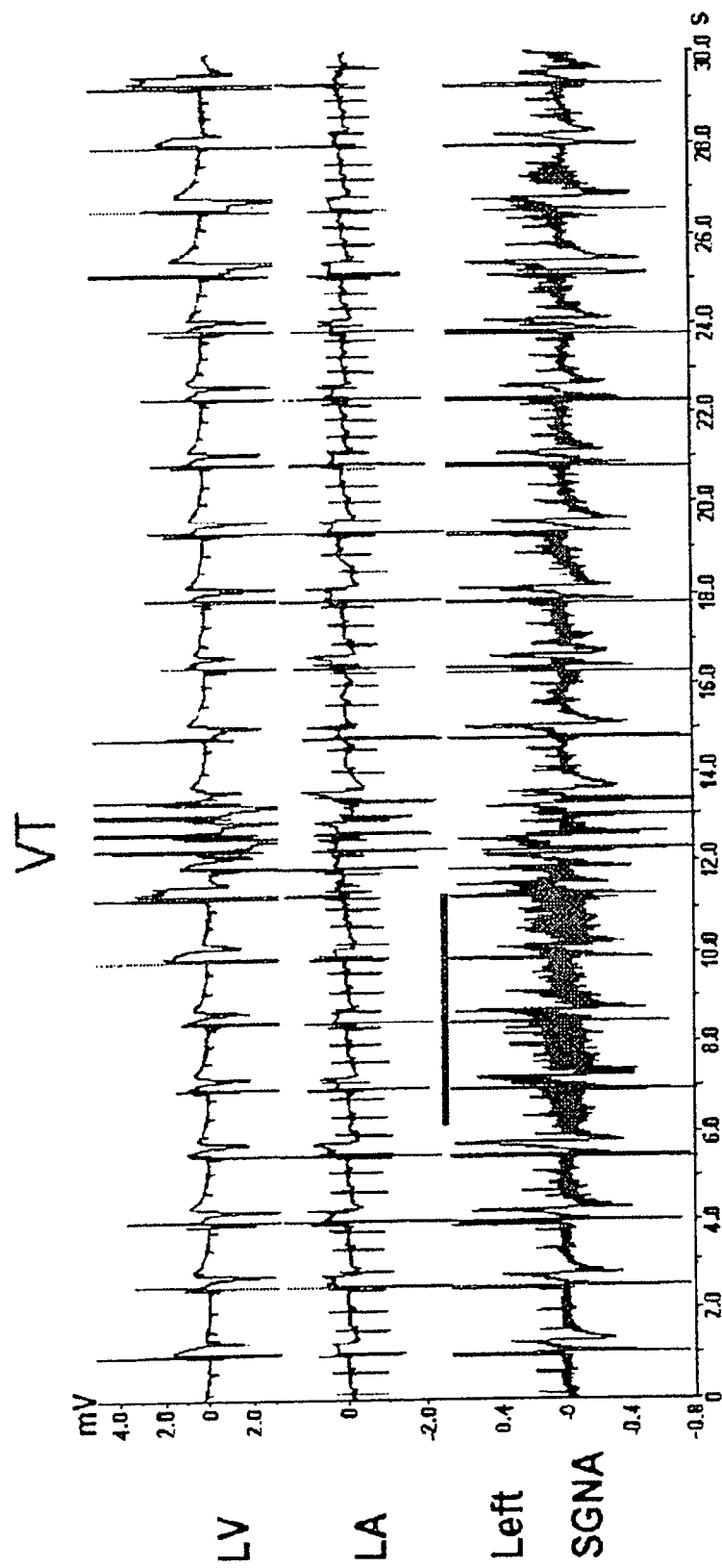
FIGS. 14A-B show two separate 30 second bipolar LV and LA electrograms and SGNA obtained by a stainless steel wire electrode implanted in the LSG of an ambulatory canine SCD model taken four weeks after surgery.
Figure 14B:
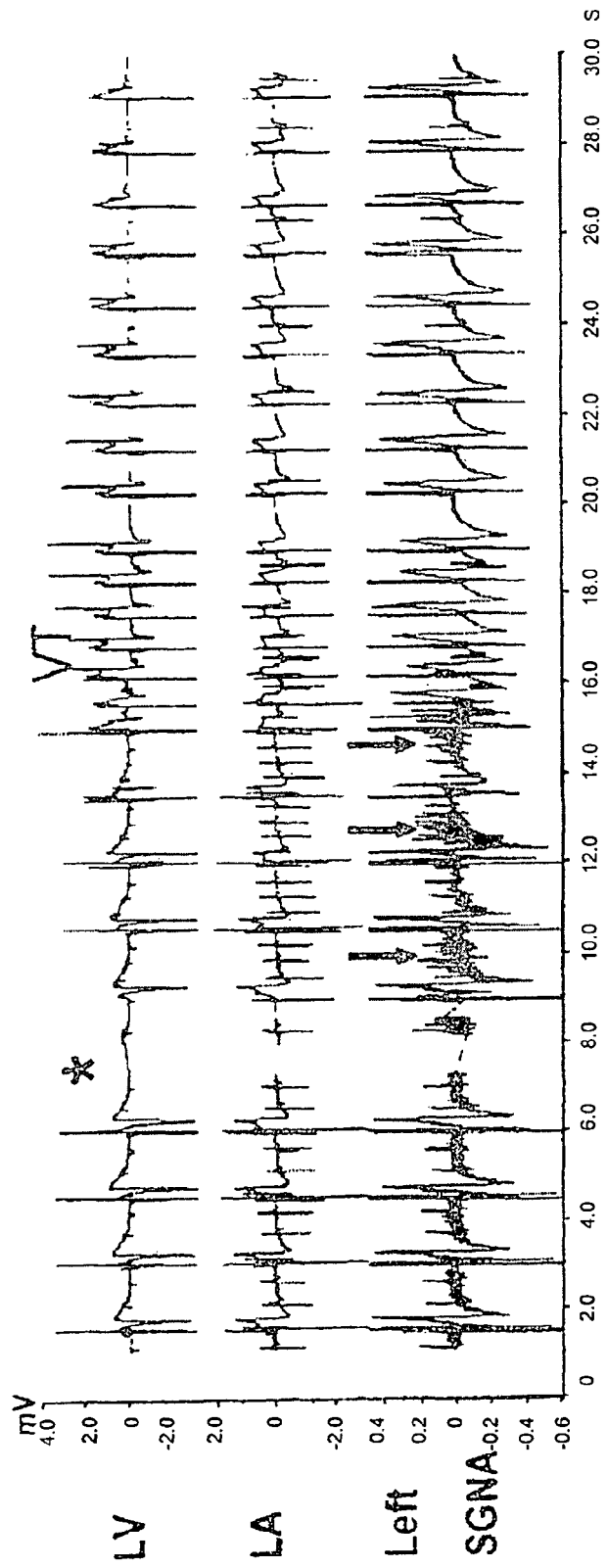

An increase in SGNA from the LSG was observed to precede the onset of ventricular tachycardia, ventricular fibrillation and sudden cardiac death. FIGS. 14A-B are simultaneous 30 second recordings of SGNA from the LSG and ECG in a canine SCD model taken four weeks after the first surgery. FIG. 14A shows the onset of ventricular tachycardia following either persistent SGNA, as indicated by the horizontal line above the SGNA recordings. The onset of ventricular tachycardia also induced by intermittent SGNA, as indicated by the arrows in FIG. 14B. Increased SGNA from the LSG induced VT after a 6 second latency. The asterisk in FIG. 14B shows a signal drop, likely due to the movement of the SCD canine subject.

Figure 15:
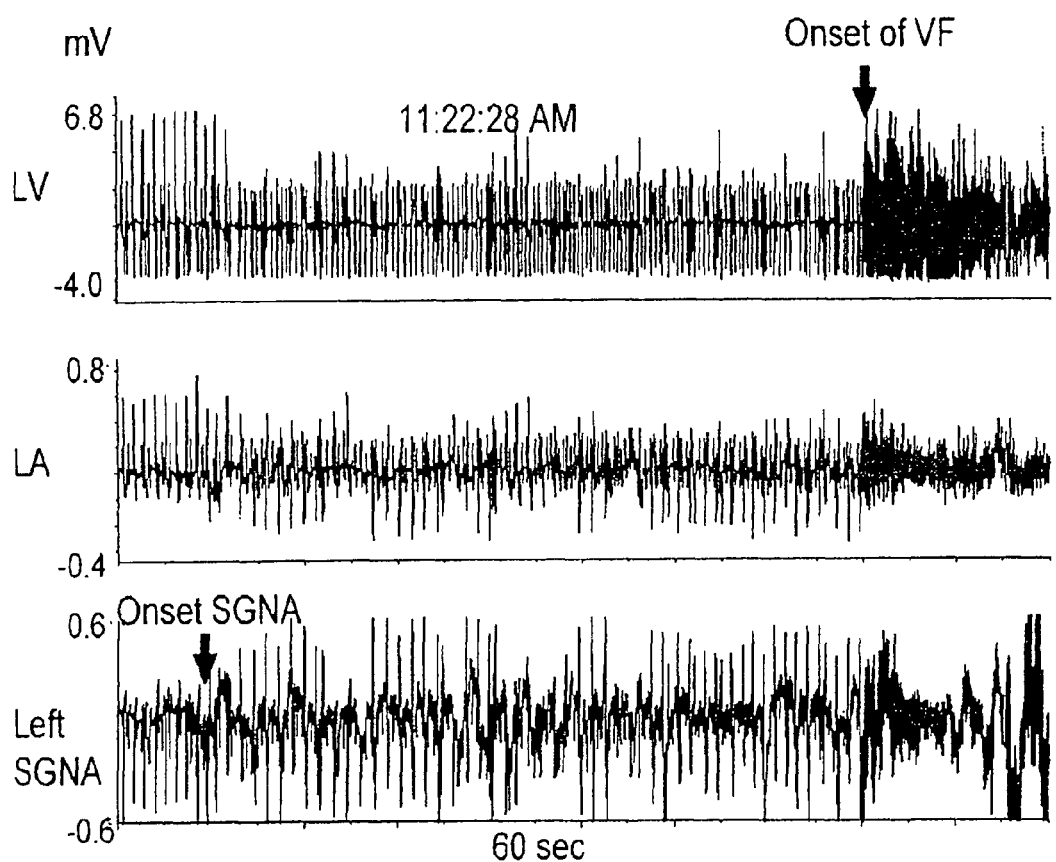
FIG. 15 shows a 60 second bipolar LV and LA electrograms and SGNA obtained by a stainless steel wire electrode implanted in the LSG of a canine SCD model. The LV recording showed accelerated escape rate and reduced electrogram amplitude soon after the onset of SGNA. The onset of increased SGNA (as indicated by the arrow) was followed by ventricular fibrillation after approximately 40 seconds.

The relationship between elevated SGNA from the LSG and heart rate is depicted in FIG. 15, which shows a 60 second bipolar LV and LA electrograms and SGNA obtained by a stainless steel wire electrode implanted in the LSG of a canine SCD model. The LV recording showed accelerated escape rate and reduced electrogram amplitude soon after the onset of SGNA. The onset of increased SGNA (as indicated by the arrow) was followed by ventricular fibrillation after approximately 40 seconds.

FIGS. 16A-C show bipolar LV and LA electrograms and SGNA obtained by a stainless steel wire electrode implanted in the LSG of a canine SCD model. FIG. 16A shows pacemaker non-capture, resulting in the conversion of intermittent SGNA into continuous SGNA in FIG. 166. The SGNA continued uninterrupted for 6 minutes, resulting in accelerated ventricular escape rhythm followed by ventricular fibrillation, as shown in FIG. 16C. FIGS. 16A-B are continuous tracings.

Figure 17:
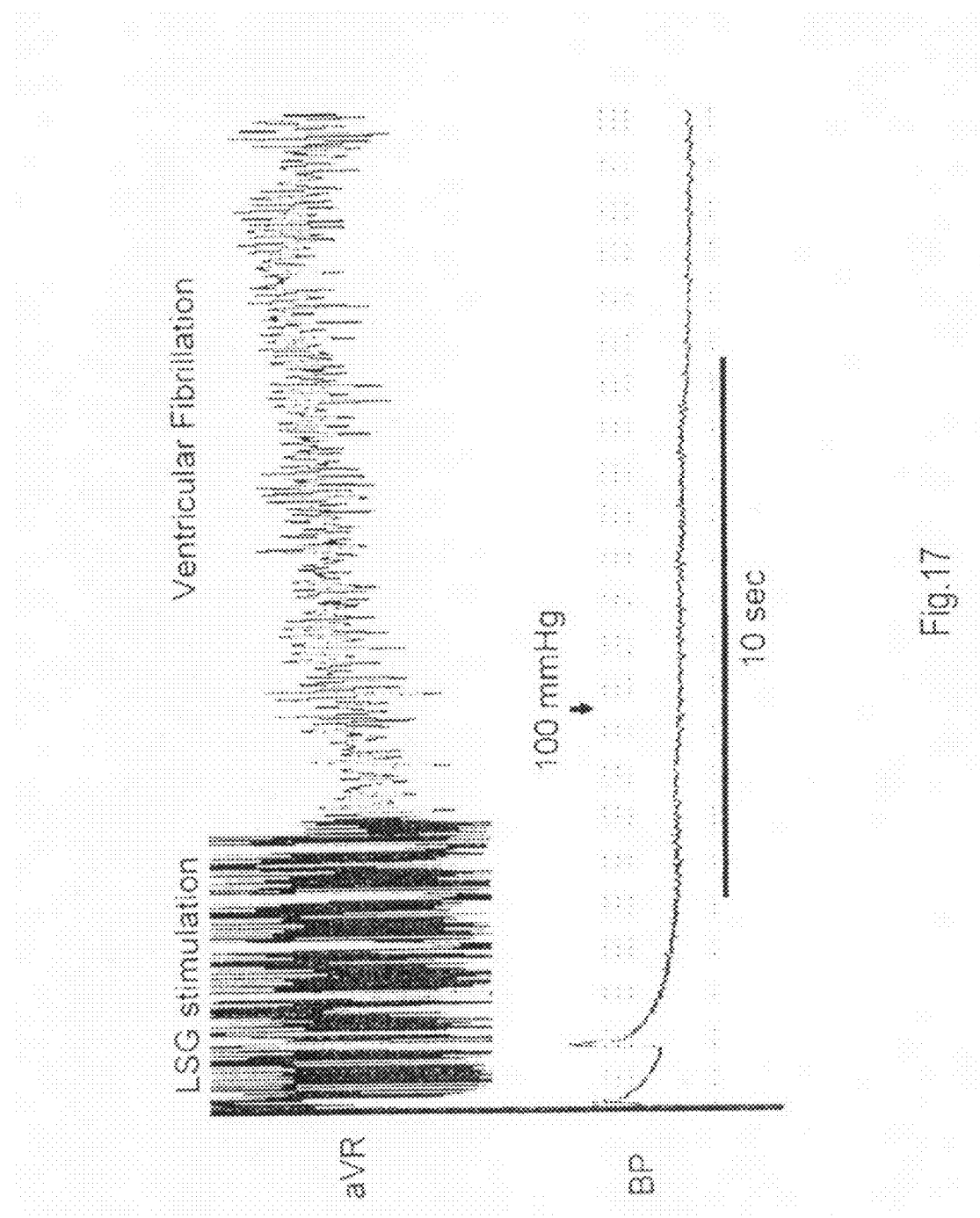
FIG. 17 shows the effect of LSG stimulation on arrhythmia. The canine SCD model with complete AV block, MI and NGF infusion to the LSG was subjected to electrical stimulation of the LSG (5 ms pulse width, 50 mA, 20 Hz, total duration 10 s). Ventricular fibrillation occurred after >6 seconds of stimulation.

FIG. 17 shows the effect of LSG stimulation on arrhythmia. The canine SCD model with complete AV block, MI and NGF infusion to the LSG was subjected to electrical stimulation of the LSG (5 ms pulse width, 50 mA, 20 Hz, total duration 10 s). Ventricular fibrillation occurred after >6 seconds of stimulation.

EXAMPLE 8

Figure 19:
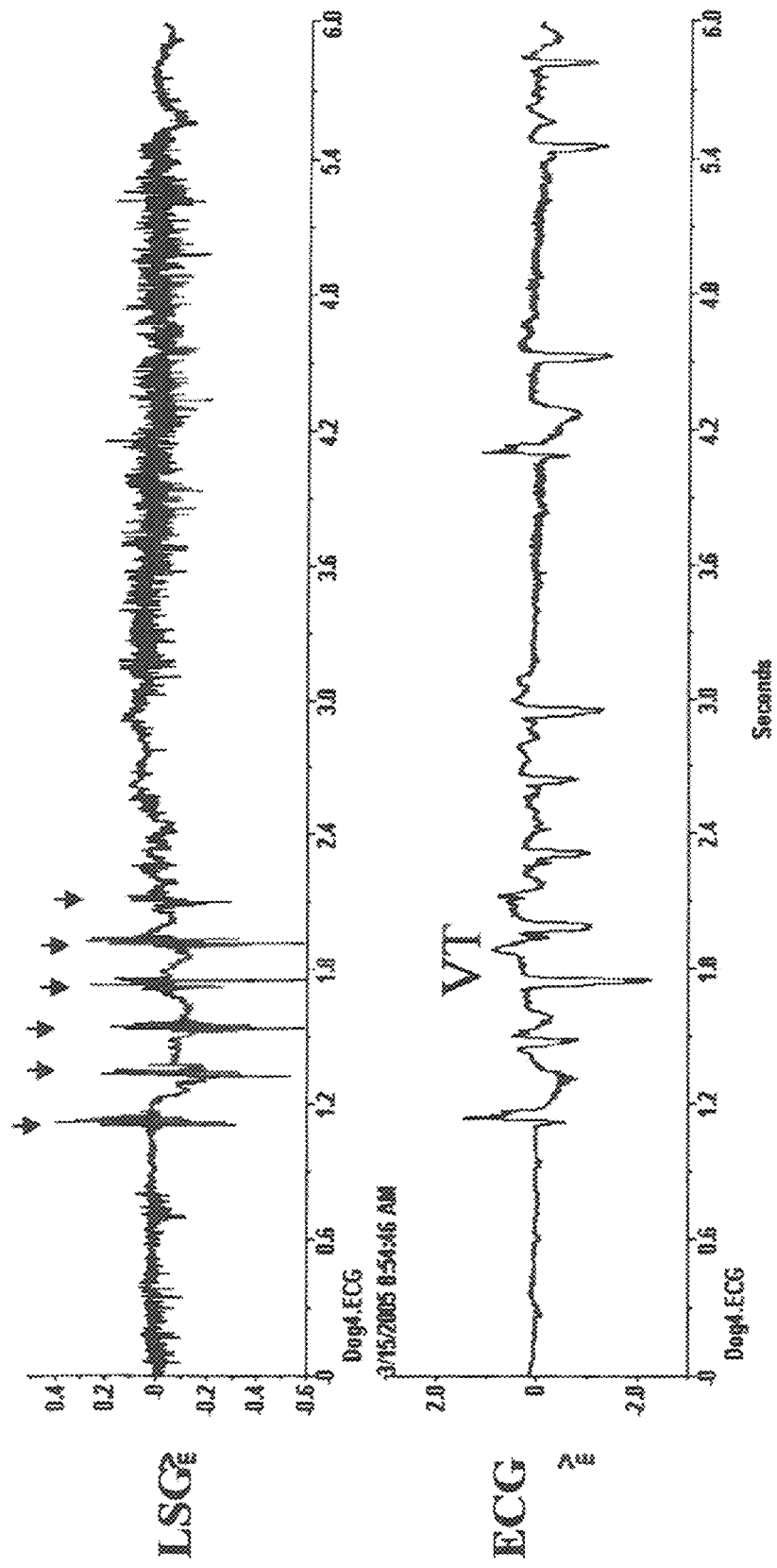
FIG. 19 shows the characteristic high amplitude spikes (arrows) preceding the onset of ventricular tachycardia (VT) in the SCD model.

Epileptiform-like Spike Discharges from the Stellate Ganglion Precede Arrhythmias Stellate ganglion nerve activity (SGNA) from 7 dogs with myocardial infarction, complete atrioventricular block and nerve growth factor (NGF) infusion to the left stellate ganglion (sudden death model) was successfully recorded. In addition to the high frequency SGNA examples shown in FIGS. 13 and 14, interesting high amplitude (epileptiform-like) spikes in the SGNA recordings (FIG. 18) were observed in all 7 dogs. FIG. 18 shows a typical example of the high amplitude spikes newly observed from the left stellate ganglion in a canine model of sudden cardiac death. The baseline wondering is similar to the "paroxysmal depolarization shift" that accompanies spike discharges, which are the neurophysiological hall marks of seizures. The spike frequency is about 6 Hz in this example. Repeated measurements have shown that the frequency of these spikes is about $6.6 \pm 0.77$ HZ and their amplitude is about $0.91 \pm 0.16$ mV. FIGS. 19 and 20 show that these epileptiform-like spikes (arrows in FIG. 19, panel A) precede the onset of ventricular tachycardia (VT). The upper tracings show left SGNA and the lower tracings show the simultaneously recorded ECG.

FIG. 21 further shows that the epileptiform-like discharges induce premature ventricular contraction (PVC), while FIG. 22 shows that the epileptiform-like discharges induce morphology changes of QRST (arrows). FIG. 23 shows that these epileptiform-like spikes precede the onset of ventricular tachycardia (VT) or premature ventricular contractions (PVCs). The upper tracing shows left SGNA and the lower tracing shows the simultaneously recorded ECG. Panels A and B were made 4 wks after first surgery. Spikes (arrows) induced nonsustained polymorphic ventricular tachycardia (VT—panel A), and fast accelerated idioventricular rhythm (panel B). Panel C was recorded 3 weeks after first surgery.

Note that the spikes (arrows) induced premature ventricular contractions (V) and nonsustained ventricular tachycardia (panel B). All tracings are 30-sec long. These tracings are discontinuous.

These novel spikes are similar to the epileptiform discharges seen on electroencephalogram recordings in patients with seizure disorders. Significantly, while these high frequency spikes were seen in all 7 dogs in the sudden death model group, they were not seen in any of the 6 normal control dogs. These results show that abnormal SGNA is present in the stellate ganglion in this canine model of sudden cardiac death, and that there is a causal relationship between abnormal SGNA and ventricular arrhythmias.

EXAMPLE 9

Stellate Ganglion Nerve Activity and the Onset of Spontaneous VT

The SGNA recorded in the sudden death model was partially analyzed (N=7). These dogs were monitored for an average of 55±43 days per dog. Among them, 3 dogs died suddenly during follow-up. All 7 dogs had phase-1 ventricular tachycardia (VT that occurred immediately post-infarct period) and phase-2 ventricular tachycardia (VT that occurred 10 days after myocardial infarction). Data Sciences International (DSI) monitoring showed that there were 1.4±1.1 phase-2 ventricular tachycardia episodes/day. Randomly selected phase-2 ventricular tachycardia episodes (N=205) from 4 dogs were analyzed. The results showed that 177 of 205 ventricular tachycardia episodes (86.3%) were preceded by elevated SGNA. The elevated SGNA can be either high frequency activation, such as that shown in FIGS. 13 and 14, or in the form of epileptiform discharges (FIGS. 18 and 19).

EXAMPLE 9

Quantitative Analyses of Nerve Recordings

A new software was developed to analyze the nerve activity. FIG. 24 shows an example of selected one-minute recording of ECG, left SGNA and right SGNA from dog #4 of the study that included 6 normal dogs. Panels A and B are continuous tracings. Note that the onset of SGNA (arrow) is associated with a shortened activation cycle length and decreased heart rate variability. Panel C shows RR interval and SGNA plotted against consecutive beats (QRS complexes). The SGNA signals were first filtered to eliminate the low frequency motion noise and the superimposed ECG complexes. They were then analyzed based on a dV/dt threshold criterion. In this tracing, all events that exceeded 0.25 V/s were selected as nerve activity. The amplitude of the nerve activity in each RR interval was summed and plotted against time. Note that the RR interval plot shows significant periodic baseline variations that ranged from 400 ms to 1100 ms even before the onset of SGNA shown in the lower two lines in Panel C. Onset of right SGNA was immediately followed by the onset of left SGNA, and was associated with reduced RR interval and RR interval variability. While the right SGNA remained at a high level after its onset, the left SGNA reached its peak within 10 heart beats before gradually declining. The onset of SGNA shortened the activation cycle length from 760±136 ms to 577±73 ms (p=0.0021) and decreased the standard deviation of all N-N intervals (SDNN) from 236±93 ms to 121±51 ms (p=0.007) on average in the 6 studied normal dogs. The ratio of SDNN and mean NN (SDNN/mean NN) also reduced significantly from 0.30±0.08 at baseline to 0.20±0.06 during SGNA (p=0.015). The preliminary results shown in FIG. 24 support the feasibility of the SDNN analyses used in the research study design. The results show that sympathetic nerve activity reduces heart rate variability.

EXAMPLE 10

Effects of Anti-convulsants on SGNA

Anti-convulsant drugs may exert an anti-arrhythmic effect by suppressing the high frequency SGNA from the LSG. Phenytoin (Dilantin®) is one of the most commonly used anti-convulsants and has been shown to suppress the SGNA in ambulatory canine subjects within the therapeutic range of 10-20 mg/L.

After confirming the successful recording of SGNA from the canine subject, 400 mg (approximately 18 mg/kg) of phenytoin was administered intravenously to the canine subject. Phenytoin was injected at 9:45 a.m. and the tracings following that time show the effects of phenytoin injection on the heart rate and the SGNA of the canine subject.

The serum concentration of the canine subject two hours after the initial injection was 12.9 mg/L, which was within the therapeutic range of 10-20 mg/L. The results showed that SGNA appeared to decrease significantly 3-12 hours after the initial injection. There was an increase in the SGNA observed roughly 20 hours after the initial injection, which may represent a rebound sympathetic neural discharges hyper-activation.

An oral dose of phenytoin was also administered to the canine subject (800 mg single dose, or roughly 30 mg/kg) after serum levels from the initial injection of phenytoin dropped to zero. The serum level 2 hours after the oral dose was 2.2 mg/L, which is sub-therapeutic. At this dose, there were little changes in the SGNA. These data show that a therapeutic dose of phenytoin can suppress SGNA from the LSG and that a sub-therapeutic dose has little effect. The data also suggest that a dose-response relationship may be present.

The invention claimed is:

1. A method for determining an increased likelihood of the occurrence of a cardiac arrhythmia, myocardial ischemia, congestive heart failure and other diseased condition of the heart associated with elevated sympathetic neural discharges in a patient, the method comprising:
monitoring the left stellate ganglia nerve activity of the patient for epileptiform-like discharges;
detecting an increase in the stellate ganglia nerve activity; and
producing an output signal in response to a detected increase in the stellate ganglia nerve activity.

2. The method of claim 1 wherein the step of monitoring the stellate ganglia nerve activity comprises implanting an electrode on the left stellate ganglion in the patient, wherein the electrode senses the electrical activity of the left stellate ganglion.

3. The method of claim 2 wherein the increase in the stellate ganglia nerve activity is determined by a two-fold increase in the amplitude and/or frequency of the sensed electrical activity beyond defined normal values.

4. The method of claim 2 wherein the increase in the stellate ganglia nerve activity is determined by comparing the sensed electrical activity and the normal electrical activity of the patient.

5. The method of claim 1 wherein the output signal is an audible sound.

6. The method of claim 1 wherein the output signal is a radio-transmitted command signal.

7. The method of claim 1, wherein the output is a radiofrequency signal or an electrical signal.

8. The method of claim 7 further comprising the step of delivering therapy in response to the command signal, the therapy selected from any one or more of the group consisting of:
  delivering one or more pharmacological agents;
  stimulating myocardial hyperinnervation in the sinus node and right ventricle of the heart of the patient; and
  applying cardiac pacing, cardioversion or defibrillation shocks.

9. The method of claim 8 wherein the one or more pharmacological agents is an anti-convulsant agent.

10. The method of claim 9 wherein the anti-convulsant agent is selected from the group consisting of: phenytoin, carbamazepine, valproate, and phenobarbitone.

11. The method of claim 8 wherein the one or more pharmacologic agent is suitable for the treatment of myocardial ischemia and is selected from the group consisting of: statins, angiotensin-converting enzyme (ACE) inhibitors, aspirin, beta blockers, calcium channel blockers, and nitrates.

12. A system for determining an increased likelihood of the occurrence of a cardiac arrhythmia, myocardial ischemia, congestive heart failure and other diseased condition of the heart associated with elevated sympathetic neural discharges in a patient, the system comprising:
  an electrode that senses the electrical activity of the left stellate ganglion for acquiring data relating to epileptiform-like sympathetic neural discharges of a patient from the left stellate ganglia or the thoracic ganglia;
  a processor for receiving the data acquired from the sensor, wherein the processor analyzes the data and determines if there is an increase in the sympathetic neural discharge; and
  an output unit for generating an output signal in response to a determined increase in the sympathetic neural discharge.

13. The system of claim 12 wherein the processor determines that an increase in the sympathetic neural discharge has occurred by a two-fold increase in the amplitude or frequency of the sensed electrical activity beyond defined normal values.

14. The system of claim 12 wherein the processor determines that an increase in the sympathetic neural discharge has occurred by comparing the sensed electrical activity and the normal electrical activity of the left stellate ganglion.

15. The system of claim 12 wherein the output signal is an audible sound.

16. The system of claim 12 wherein the output signal is a command signal.

17. The system of claim 12, wherein the output is a radiofrequency signal or an electrical signal.

18. The system of claim 12 further comprising an anti-arrhythmia delivery module for delivering therapy in response to the command signal, the therapy selected from any one or more of the group consisting of:
  delivering one or more pharmacological agents;
  stimulating myocardial hyperinnervation in the sinus node and right ventricle of the heart of the patient; and
  applying cardiac pacing, and cardioversion or defibrillation shocks.

19. The system of claim 18 wherein the one or more pharmacological agents is an anti-convulsant agent.

20. The system of claim 19 wherein the anti-convulsant agent is selected from the group consisting of: phenytoin, carbamazepine, valproate, and phenobarbitone.

21. The system of claim 19 wherein the one or more pharmacologic agent is suitable for the treatment of myocardial ischemia and is selected from the group consisting of: statins, angiotensin-converting enzyme (ACE) inhibitors, aspirin, beta blockers, calcium channel blockers, and nitrates.

22. A system for determining an increased likelihood of the occurrence of a cardiac arrhythmia, myocardial ischemia, congestive heart failure and other diseased condition of the heart associated with elevated sympathetic neural discharges in a patient, the system comprising:
  means for monitoring epileptiform-like sympathetic neural discharges of a patient from the stellate ganglia or the thoracic ganglia comprising sensing the electrical activity of the left stellate ganglion;
  means for determining an increase in the sympathetic neural discharge comprising comparing the sensed electrical activity of the left stellate ganglion and the normal electrical activity of the left stellate ganglion; and
  means for producing an output signal in response to a determined increase in the sympathetic neural discharge.

23. The system of claim 22 wherein the increase in the sympathetic neural discharge is determined by detecting an increase in the amplitude or frequency of the sensed electrical activity beyond defined normal values.

24. The system of claim 22 wherein the output signal is an audible sound.

25. The system of claim 22 wherein the output signal is a command signal.

26. The system of claim 22, wherein the output is a radiofrequency signal or an electrical signal.

27. The system of claim 26 further comprising means for delivering anti-arrhythmic therapy in response to the command signal, the anti-arrhythmic therapy selected from any one or more of the group consisting of:
  delivering one or more pharmacological agents;
  stimulating myocardial hyperinnervation in the sinus node and right ventricle of the heart of the patient; and
  applying cardiac pacing, cardioversion or defibrillation shocks.

28. The system of claim 27 wherein the one or more pharmacological agents is an anti-convulsant agent.

29. The system of claim 27 wherein the anti-convulsant agent is selected from the group consisting of: phenytoin, carbamazepine, valproate, and phenobarbitone.

30. The system of claim 27 wherein the one or more pharmacologic agent is suitable for the treatment of myocardial ischemia and is selected from the group consisting of: statins, angiotensin-converting enzyme (ACE) inhibitors, aspirin, beta blockers, calcium channel blockers, and nitrates.

* * * * *